US012577303B2

(12) United States Patent
Liu

(10) Patent No.: US 12,577,303 B2
(45) Date of Patent: Mar. 17, 2026

(54) SIRPα-TARGETING ANTIBODY OR ANTIGEN BINDING FRAGMENT THEREOF, AND PREPARATION AND APPLICATION THEREOF

(71) Applicant: L&L Bio Co., Ltd., Ningbo, China, Zhejiang (CN)

(72) Inventor: Jiajian Liu, Shanghai (CN)

(73) Assignee: L&L Bio Co., Ltd., Ningbo, China, Zhejiang (CN)

( * ) Notice: Subject to any disclaimer, the term of this patent is extended or adjusted under 35 U.S.C. 154(b) by 645 days.

(21) Appl. No.: 17/910,040

(22) PCT Filed: Mar. 17, 2021

(86) PCT No.: PCT/CN2021/081272
§ 371 (c)(1),
(2) Date: Sep. 8, 2022

(87) PCT Pub. No.: WO2021/185273
PCT Pub. Date: Sep. 23, 2021

(65) Prior Publication Data
US 2023/0106247 A1     Apr. 6, 2023

(30) Foreign Application Priority Data
Mar. 20, 2020     (CN) ......................... 202010204130.2

(51) Int. Cl.
| | |
|---|---|
| *C07K 16/28* | (2006.01) |
| *A61K 39/00* | (2006.01) |
| *A61K 39/395* | (2006.01) |
| *A61P 35/00* | (2006.01) |

(52) U.S. Cl.
CPC ...... *C07K 16/2803* (2013.01); *A61K 39/3955* (2013.01); *A61P 35/00* (2018.01); *A61K 39/00* (2013.01); *A61K 2039/507* (2013.01); *C07K 2317/20* (2013.01); *C07K 2317/24* (2013.01); *C07K 2317/31* (2013.01); *C07K 2317/92* (2013.01)

(58) Field of Classification Search
None
See application file for complete search history.

(56) References Cited

U.S. PATENT DOCUMENTS

| | | |
|---|---|---|
| 2014/0242095 A1 | 8/2014 | Wang et al. |
| 2019/0275150 A1 | 9/2019 | Pincetic et al. |
| 2022/0119520 A1 | 4/2022 | Wang et al. |

FOREIGN PATENT DOCUMENTS

| | | |
|---|---|---|
| CN | 111635458 A | 9/2020 |
| WO | 2017178653 A2 | 10/2017 |
| WO | 2019175218 A1 | 9/2019 |

OTHER PUBLICATIONS

Koenig "Mutational landscape of antibody variable domains reveals a switch modulating the interdomain conformational dynamics and antigen binding" PNAS E486-E495 (Year: 2017).*
Kussie "A Single Engineered Amino Acid Substitution Changes Antibody Fine Specificity" J immunol 152(1):146-52 (Year: 1994).*
Evitria "Types of monoclonal antibodies" accessed from www.evitria.com on May 20, 2025 (Year: 2025).*
MSK "Cancer vaccines: the types, how they work, and which cancers they treat" accessed from mskcc.org on May 20, 2025 (Year: 2025).*
Jun. 1, 2021 International Search Report issued in International Patent Application No. PCT/CN2021/081272.
Jun. 1, 2021 Written Opinion of the International Searching Authority issued in International Patent Application No. PCT/CN2021/081272.
May 29, 2025 Chinese First Office Action issued in Chinese Patent Application No. 2020102041302.
May 29, 2025 Chinese First Search Report issued in Chinese Patent Application No. 2020102041302.

* cited by examiner

*Primary Examiner* — Adam Weidner
(74) *Attorney, Agent, or Firm* — Houston Beshining Law Office PLLC; Liangang Ye

(57) ABSTRACT

Disclosed is a SIRPα-targeting antibody or an antigen-binding fragment thereof, comprising a light chain variable region and/or a heavy chain variable region. The antibody or the antigen-binding fragment thereof binds to human SIRPα-V1 and human SIRPα-V2, but weakly or does not bind to human SIRPβ and SIRPγ, does not bind to human T cells, and has the function of blocking the binding of SIRPα to CD47. Further disclosed are a bispecific antibody comprising same, a method for preparing the antibody or the antigen-binding fragment thereof and an application thereof. The unique properties of the disclosed antibody or the antigen-binding fragment thereof enable same to be more suitable for the development of drugs for an antibody or antigen-binding fragment against a human SIRPα target. As a candidate drug, same can be administered alone or in combination, providing a new or even better choice for the combined immunotherapy of tumors.

19 Claims, 6 Drawing Sheets
Specification includes a Sequence Listing.

Fluorescence intensity

Fluorescence intensity

SEQUENCE LISTING

<160> NUMBER OF SEQ ID NOS: 69

<210> SEQ ID NO 1
<211> LENGTH: 47
<212> TYPE: DNA
<213> ORGANISM: Artificial Sequence
<220> FEATURE:
<223> OTHER INFORMATION: PCR primer SI-2F

<400> SEQUENCE: 1
taaacggatc tctagcgaat tcatggagcc cgccggcccg gcccccg                47

<210> SEQ ID NO 2
<211> LENGTH: 49
<212> TYPE: DNA
<213> ORGANISM: Artificial Sequence
<220> FEATURE:
<223> OTHER INFORMATION: PCR primer SI-2R

<400> SEQUENCE: 2
cggccttgcc ggcctcgagc ggccgctgtc tgattcggac gaggtagag                49

<210> SEQ ID NO 3
<211> LENGTH: 340
<212> TYPE: PRT
<213> ORGANISM: Artificial Sequence
<220> FEATURE:
<223> OTHER INFORMATION: Cyno Sirpalpha protein RB3-3 sequence

<400> SEQUENCE: 3

Glu Glu Glu Leu Gln Val Ile Gln Pro Glu Lys Ser Val Ser Val Ala
1               5                   10                  15

Ala Gly Asp Ser Ala Thr Leu Asn Cys Thr Val Thr Ser Leu Ile Pro
            20                  25                  30

Val Gly Pro Ile Gln Trp Phe Arg Gly Ala Gly Pro Gly Arg Glu Leu
        35                  40                  45

Ile Tyr His Gln Lys Glu Gly His Phe Pro Arg Val Thr Ser Val Ser
    50                  55                  60

Glu Ser Thr Lys Arg Asn Asn Met Asp Phe Ser Ile His Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Val Lys Ser Gly Ala Gly Thr Glu Leu Ser

-continued

```
              100               105                110

Val Arg Ala Lys Pro Ser Ala Pro Val Val Ser Gly Pro Ala Val Arg
          115                 120                 125

Ala Thr Ala Glu His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Phe Gln Thr Asn Val Asp Pro Ala Gly Lys Ser Val Ser Tyr
              165                 170                 175

Ser Ile Arg Ser Thr Ala Arg Val Val Leu Thr Arg Arg Asp Val His
              180                 185                 190

Ser Gln Val Ile Cys Glu Val Ala His Val Thr Leu Gln Gly Asp Pro
              195                 200                 205

Leu Arg Gly Thr Ala Asn Leu Ser Glu Ala Ile Arg Val Pro Pro Phe
    210                 215                 220

Leu Glu Val Thr Gln Gln Ser Met Arg Ala Asp Asn Gln Val Asn Val
225                 230                 235                 240

Thr Cys Gln Val Thr Lys Phe Tyr Pro Gln Arg Leu Gln Leu Thr Trp
              245                 250                 255

Leu Glu Asn Gly Asn Val Ser Arg Thr Glu Met Ala Ser Ala Leu Pro
              260                 265                 270

Glu Asn Lys Asp Gly Thr Tyr Asn Trp Thr Ser Trp Leu Leu Val Asn
              275                 280                 285

Val Ser Ala His Arg Asp Asp Val Lys Leu Thr Cys Gln Val Glu His
    290                 295                 300

Asp Gly Gln Pro Ala Val Asn Lys Ser Phe Ser Val Lys Val Ser Ala
305                 310                 315                 320

His Pro Lys Glu Gln Gly Ser Asn Thr Ala Ala Glu Asn Thr Gly Thr
              325                 330                 335

Asn Glu Arg Asn
          340

<210> SEQ ID NO 4
<211> LENGTH: 340
<212> TYPE: PRT
<213> ORGANISM: Artificial Sequence
<220> FEATURE:
<223> OTHER INFORMATION: Cyno Sirpalpha protein RB3-5 sequence

<400> SEQUENCE: 4

Glu Glu Glu Leu Gln Val Ile Gln Pro Glu Lys Ser Val Ser Val Ala
1               5                 10                 15

Ala Gly Asp Ser Ala Thr Leu Asn Cys Thr Val Ser Ser Leu Ile Pro
          20                 25                 30

Val Gly Pro Ile Gln Trp Phe Arg Gly Ala Gly Pro Gly Arg Glu Leu
          35                 40                 45

Ile Tyr Asn Leu Lys Glu Gly His Phe Pro Arg Val Thr Pro Val Ser
    50                 55                 60

Asp Pro Thr Lys Arg Asn Asn Met Asp Phe Ser Ile Arg Ile Ser Asn
65                 70                 75                 80

Ile Thr Pro Ala Asp Ala Gly Thr Tyr Tyr Cys Val Lys Phe Arg Lys
              85                 90                 95

Gly Ser Pro Asp Val Glu Leu Lys Ser Gly Ala Gly Thr Glu Leu Ser
          100                 105                 110

Val Arg Ala Lys Pro Ser Ala Pro Val Val Ser Gly Pro Ala Val Arg
```

-continued

```
                115                 120                 125

Ala Thr Ala Glu His Thr Val Ser Phe Thr Cys Glu Ser His Gly Phe
    130                 135                 140

Ser Pro Arg Asp Ile Thr Leu Lys Trp Phe Lys Asn Gly Asn Glu Leu
145                 150                 155                 160

Ser Asp Val Gln Thr Asn Val Asp Pro Ala Gly Lys Ser Val Ser Tyr
                165                 170                 175

Ser Ile Arg Ser Thr Ala Arg Val Leu Leu Thr Arg Arg Asp Val His
                180                 185                 190

Ser Gln Val Ile Cys Glu Val Ala His Val Thr Leu Gln Gly Asp Pro
                195                 200                 205

Leu Arg Gly Thr Ala Asn Leu Ser Glu Ala Ile Arg Val Pro Pro Phe
    210                 215                 220

Leu Glu Val Thr Gln Gln Ser Met Arg Ala Asp Asn Gln Val Asn Val
225                 230                 235                 240

Thr Cys Gln Val Thr Lys Phe Tyr Pro Gln Arg Leu Gln Leu Thr Trp
                245                 250                 255

Leu Glu Asn Gly Asn Val Ser Arg Thr Glu Met Ala Ser Ala Leu Pro
                260                 265                 270

Glu Asn Lys Asp Gly Thr Tyr Asn Trp Thr Ser Trp Leu Leu Val Asn
    275                 280                 285

Val Ser Ala His Arg Asp Asp Val Lys Leu Thr Cys Gln Val Glu His
    290                 295                 300

Asp Gly Gln Pro Ala Val Asn Lys Ser Phe Ser Val Lys Val Ser Ala
305                 310                 315                 320

His Pro Lys Glu Gln Gly Ser Asn Thr Ala Ala Glu Asn Thr Gly Thr
                325                 330                 335

Asn Glu Arg Asn
            340
```

```
<210> SEQ ID NO 5
<211> LENGTH: 340
<212> TYPE: PRT
<213> ORGANISM: Artificial Sequence
<220> FEATURE:
<223> OTHER INFORMATION: Cyno Sirpalpha protein RB6-1 sequence

<400> SEQUENCE: 5
```

```
Glu Glu Glu Leu Gln Val Ile Gln Pro Glu Lys Ser Val Ser Val Ala
1                 5                   10                  15

Ala Gly Glu Ser Ala Thr Leu Asn Cys Thr Ala Thr Ser Leu Ile Pro
                20                  25                  30

Val Gly Pro Ile Gln Trp Phe Arg Gly Val Gly Pro Gly Arg Glu Leu
            35                  40                  45

Ile Tyr His Gln Lys Glu Gly His Phe Pro Arg Val Thr Pro Val Ser
    50                  55                  60

Asp Pro Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Leu Lys Ser Gly Ala Gly Thr Glu Leu Ser
                100                 105                 110

Val Arg Ala Lys Pro Ser Ala Pro Val Val Ser Gly Pro Ala Val Arg
            115                 120                 125

Ala Thr Ala Glu His Thr Val Ser Phe Thr Cys Glu Ser His Gly Phe
```

-continued

```
            130             135             140

Ser Pro Arg Asp Ile Thr Leu Lys Trp Phe Lys Asn Gly Asn Glu Leu
145             150             155             160

Ser Asp Phe Gln Thr Asn Val Asp Pro Ala Gly Lys Ser Val Ser Tyr
                165             170             175

Ser Ile Arg Ser Thr Ala Arg Val Val Leu Thr Arg Arg Asp Val His
                180             185             190

Ser Gln Val Ile Cys Glu Val Ala His Val Thr Leu Gln Gly Asp Pro
            195             200             205

Leu Arg Gly Thr Ala Asn Leu Ser Glu Ala Ile Arg Val Pro Pro Phe
        210             215             220

Leu Glu Val Thr Gln Gln Ser Met Arg Ala Asp Asn Gln Val Asn Val
225             230             235             240

Thr Cys Gln Val Met Lys Phe Tyr Pro Gln Arg Leu Gln Leu Thr Trp
                245             250             255

Leu Glu Asn Gly Asn Val Ser Arg Thr Glu Met Ala Ser Ala Leu Pro
            260             265             270

Glu Asn Lys Asp Gly Thr Tyr Asn Trp Thr Ser Trp Leu Leu Val Asn
        275             280             285

Val Ser Ala His Arg Asp Asp Val Lys Leu Thr Cys Gln Val Glu His
    290             295             300

Asp Gly Gln Pro Ala Val Asn Lys Ser Phe Ser Val Lys Val Ser Ala
305             310             315             320

His Pro Lys Glu Gln Gly Ser Asn Thr Ala Ala Glu Asn Thr Gly Thr
                325             330             335

Asn Glu Arg Asn
                340

<210> SEQ ID NO 6
<211> LENGTH: 340
<212> TYPE: PRT
<213> ORGANISM: Artificial Sequence
<220> FEATURE:
<223> OTHER INFORMATION: Cyno Sirpalpha protein RB6-2 sequence

<400> SEQUENCE: 6

Glu Glu Glu Leu Gln Val Ile Gln Pro Glu Lys Ser Val Ser Val Ala
1               5               10              15

Ala Gly Glu Ser Ala Thr Leu Asn Cys Thr Ala Thr Ser Leu Ile Pro
                20              25              30

Val Gly Pro Ile Gln Trp Phe Arg Gly Val Gly Pro Gly Arg Glu Leu
            35              40              45

Ile Tyr Ser Gln Lys Glu Gly His Phe Pro Arg Val Thr Pro Val Ser
        50              55              60

Asp Pro Thr Lys Arg Asn Asn Met Asp Phe Ser Ile Arg Ile Ser Asn
65              70              75              80

Ile Thr Pro Ala Asp Ala Gly Thr Tyr Tyr Cys Val Lys Phe Arg Lys
                85              90              95

Gly Ser Pro Asp Val Glu Leu Lys Ser Gly Ala Gly Thr Glu Leu Ser
            100             105             110

Val Arg Ala Lys Pro Ser Ala Pro Val Val Ser Gly Pro Ala Val Arg
        115             120             125

Ala Thr Ala Glu His Thr Val Ser Phe Thr Cys Glu Ser His Gly Phe
    130             135             140

Ser Pro Arg Asp Ile Thr Leu Lys Trp Phe Lys Asn Gly Asn Glu Leu
```

```
145             150             155             160

Ser Asp Phe Gln Thr Asn Val Asp Pro Ala Gly Lys Ser Val Ser Tyr
                165             170             175

Ser Ile Arg Ser Thr Ala Arg Val Val Leu Thr Arg Arg Asp Val His
                180             185             190

Ser Gln Val Ile Cys Glu Val Ala His Val Thr Leu Gln Gly Asp Pro
                195             200             205

Leu Arg Gly Thr Ala Asn Leu Ser Glu Ala Ile Arg Val Pro Pro Phe
    210             215             220

Leu Glu Val Thr Gln Gln Ser Met Arg Ala Asp Asn Gln Val Asn Val
225             230             235             240

Thr Cys Gln Val Thr Lys Phe Tyr Pro Gln Arg Leu Gln Leu Thr Trp
                245             250             255

Leu Glu Asn Gly Asn Val Ser Arg Thr Glu Met Ala Ser Ala Leu Pro
                260             265             270

Glu Asn Lys Asp Gly Thr Tyr Asn Trp Thr Ser Trp Leu Leu Val Asn
                275             280             285

Val Ser Ala His Arg Asp Asp Val Lys Leu Thr Cys Gln Val Glu His
    290             295             300

Asp Gly Gln Pro Ala Val Asn Lys Ser Phe Ser Val Lys Val Ser Ala
305             310             315             320

His Pro Lys Glu Gln Gly Ser Asn Thr Ala Ala Glu Asn Thr Gly Thr
                325             330             335

Asn Glu Arg Asn
                340

<210> SEQ ID NO 7
<211> LENGTH: 501
<212> TYPE: DNA
<213> ORGANISM: Artificial Sequence
<220> FEATURE:
<223> OTHER INFORMATION: Base sequence of light chain variable region of
      murine monoclonal antibody mab14

<400> SEQUENCE: 7
taatggtgtc cctcagctca gttccttggt ctcctgttgc tctgttttca aggtaccaga      60
tgtgatatcc agatgacaca gactacatcc tccctgtctg cctctctggg agacagagtc     120
accatcagtt gcagggcaag tcaggacatt aggaattatt taaactggta tcagcagaag     180
ccagatggaa ctgttaaact cctgatctac ttcacatcaa cattacactc aggagtccca     240
tcaaggttca gtggcagtgg gtctgggaaca gattattctc tcaccattag caacctggaa     300
caagaagata ttgccactta cttttgccaa cagggtaata cgcttccgtg gacgttcggt     360
ggaggcacca agctggaaat caaacgggct gatgctgcac caactgtatc catcttccca     420
ccatccagtg agcagttaac atctggaggt gcctcagtcg tgtgcttctg aacaactcta     480
ccccaaagac atcaggacc t                                               501

<210> SEQ ID NO 8
<211> LENGTH: 550
<212> TYPE: DNA
<213> ORGANISM: Artificial Sequence
<220> FEATURE:
<223> OTHER INFORMATION: Base sequence of heavy chain variable region of
      murine monoclonal antibody mab14

<400> SEQUENCE: 8
tcatgggatg gagctgtatc atgttctttt tggtagccgc agctacaggt gtccactccc      60
```

-continued

```
aggtccatct gcagcagcct ggggctgagc ttgtgaagcc tggggcttca gtgaagttgt    120
cctgcaaggc ttctggctac aatttcaaca tctactggat aaattgggtg aagcagaggc    180
ctggacaagg ccttgagtgg attggaaata tttatcctag tagtattagt actaactaca    240
atgagaagtt caagacgaag gccacactga ctgtagacaa atcctccaac acagtctaca    300
tgcagttcag cagcctgaca tctgaggact ctgcggtcta ttattgtgcg cgatcggagg    360
gaacttacta tggtggtcgc tacgaggggg actggtttgg ttactggggc caagggactc    420
tggtcactgt ctctgcagcc aaaacaacac ccccatcagt ctatccactg gcccctgggt    480
gtggagatac aactggttcc tccgtgactc tgggatgcct ggtcaaggggc tactgccgag    540 tcgaagttcc                                                         550
```

<210> SEQ ID NO 9
<211> LENGTH: 107
<212> TYPE: PRT
<213> ORGANISM: Artificial Sequence
<220> FEATURE:
<223> OTHER INFORMATION: Amino acid sequence of light chain variable
      region of murine monoclonal antibody mab14

<400> SEQUENCE: 9

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 10
<211> LENGTH: 126
<212> TYPE: PRT
<213> ORGANISM: Artificial Sequence
<220> FEATURE:
<223> OTHER INFORMATION: Amino acid sequence of heavy chain variable
      region of murine monoclonal antibody mab14

<400> SEQUENCE: 10

```
Gln Val His Leu Gln Gln Pro Gly Ala Glu Leu Val Lys Pro Gly Ala
1               5                   10                  15

Ser Val Lys Leu Ser Cys Lys Ala Ser Gly Tyr Asn Phe Asn Ile Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Ser Ile Ser Thr Asn Tyr Asn Glu Lys Phe
    50                  55                  60

Lys Thr Lys Ala Thr Leu Thr Val Asp Lys Ser Ser Asn Thr Val Tyr
65                  70                  75                  80

Met Gln Phe Ser Ser Leu Thr Ser Glu Asp Ser Ala Val Tyr Tyr Cys
                85                  90                  95
```

```
Ala Arg Ser Glu Gly Thr Tyr Tyr Gly Gly Arg Tyr Glu Gly Asp Trp
            100                 105                 110

Phe Gly Tyr Trp Gly Gln Gly Thr Leu Val Thr Val Ser Ala
        115                 120                 125

<210> SEQ ID NO 11
<211> LENGTH: 11
<212> TYPE: PRT
<213> ORGANISM: Artificial Sequence
<220> FEATURE:
<223> OTHER INFORMATION: Light chain CDR1 defined by CCG

<400> SEQUENCE: 11

Arg Ala Ser Gln Asp Ile Arg Asn Tyr Leu Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Light chain CDR2 defined by CCG

<400> SEQUENCE: 12

Phe Thr Ser Thr Leu His Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Light chain CDR3 defined by CCG

<400> SEQUENCE: 13

Gln Gln Gly Asn Thr Leu Pro Trp Thr
1               5

<210> SEQ ID NO 14
<211> LENGTH: 10
<212> TYPE: PRT
<213> ORGANISM: Artificial Sequence
<220> FEATURE:
<223> OTHER INFORMATION: Heavy chain CDR1 defined by CCG

<400> SEQUENCE: 14

Gly Tyr Asn Phe Asn Ile Tyr Trp Ile Asn
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Heavy chain CDR2 defined by CCG

<400> SEQUENCE: 15

Asn Ile Tyr Pro Ser Ser Ile Ser Thr Asn Tyr Asn Glu Lys Phe Lys
1               5                   10                  15

Thr

<210> SEQ ID NO 16
<211> LENGTH: 17
<212> TYPE: PRT
<213> ORGANISM: Artificial Sequence
```

-continued

```
<220> FEATURE:
<223> OTHER INFORMATION: Heavy chain CDR3 defined by CCG

<400> SEQUENCE: 16

Ser Glu Gly Thr Tyr Tyr Gly Gly Arg Tyr Glu Gly Asp Trp Phe Gly
1               5                   10                  15

Tyr

<210> SEQ ID NO 17
<211> LENGTH: 5
<212> TYPE: PRT
<213> ORGANISM: Artificial Sequence
<220> FEATURE:
<223> OTHER INFORMATION: Heavy chain CDR1 defined by Kabat

<400> SEQUENCE: 17

Ile Tyr Trp Ile Asn
1               5

<210> SEQ ID NO 18
<211> LENGTH: 9
<212> TYPE: PRT
<213> ORGANISM: Artificial Sequence
<220> FEATURE:
<223> OTHER INFORMATION: Heavy chain CDR2 defined by AbM

<400> SEQUENCE: 18

Asn Ile Tyr Pro Ser Ser Ile Ser Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Heavy chain CDR1 defined by Chothia

<400> SEQUENCE: 19

Gly Tyr Asn Phe Asn Ile Tyr
1               5

<210> SEQ ID NO 20
<211> LENGTH: 5
<212> TYPE: PRT
<213> ORGANISM: Artificial Sequence
<220> FEATURE:
<223> OTHER INFORMATION: Heavy chain CDR2 defined by Chothia

<400> SEQUENCE: 20

Tyr Pro Ser Ser Ile
1               5

<210> SEQ ID NO 21
<211> LENGTH: 7
<212> TYPE: PRT
<213> ORGANISM: Artificial Sequence
<220> FEATURE:
<223> OTHER INFORMATION: Light chain CDR1 defined by Contact

<400> SEQUENCE: 21

Arg Asn Tyr Leu Asn Trp Tyr
1               5

<210> SEQ ID NO 22
<211> LENGTH: 11
<212> TYPE: PRT
```

```
<213> ORGANISM: Artificial Sequence
<220> FEATURE:
<223> OTHER INFORMATION: Light chain CDR2 defined by Contact

<400> SEQUENCE: 22

Lys Leu Leu Ile Tyr Phe Thr Ser Thr Leu His
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Light chain CDR3 defined by Contact

<400> SEQUENCE: 23

Gln Gln Gly Asn Thr Leu Pro Trp
1               5

<210> SEQ ID NO 24
<211> LENGTH: 6
<212> TYPE: PRT
<213> ORGANISM: Artificial Sequence
<220> FEATURE:
<223> OTHER INFORMATION: Heavy chain CDR1 defined by Contact

<400> SEQUENCE: 24

Asn Ile Tyr Trp Ile Asn
1               5

<210> SEQ ID NO 25
<211> LENGTH: 12
<212> TYPE: PRT
<213> ORGANISM: Artificial Sequence
<220> FEATURE:
<223> OTHER INFORMATION: Heavy chain CDR2 defined by Contact

<400> SEQUENCE: 25

Trp Ile Gly Asn Ile Tyr Pro Ser Ser Ile Ser Thr
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Heavy chain CDR3 defined by Contact

<400> SEQUENCE: 26

Ala Arg Ser Glu Gly Thr Tyr Tyr Gly Gly Arg Tyr Glu Gly Asp Trp
1               5                   10                  15

Phe Gly

<210> SEQ ID NO 27
<211> LENGTH: 107
<212> TYPE: PRT
<213> ORGANISM: Artificial Sequence
<220> FEATURE:
<223> OTHER INFORMATION: chain in light chain constant region of human
      antibody

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30
```

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

<210> SEQ ID NO 28
<211> LENGTH: 327
<212> TYPE: PRT
<213> ORGANISM: Artificial Sequence
<220> FEATURE:
<223> OTHER INFORMATION: Heavy chain constant region of human IgG4

<400> SEQUENCE: 28

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285
```

-continued

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 29
<211> LENGTH: 107
<212> TYPE: PRT
<213> ORGANISM: Artificial Sequence
<220> FEATURE:
<223> OTHER INFORMATION: mab14-hL1, the humanized light chain variable
      region of antibody mab14

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105
```

```
<210> SEQ ID NO 30
<211> LENGTH: 107
<212> TYPE: PRT
<213> ORGANISM: Artificial Sequence
<220> FEATURE:
<223> OTHER INFORMATION: mab14-hL2, the humanized light chain variable
      region of antibody mab14

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Gly Thr Val Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105
```

```
<210> SEQ ID NO 31
<211> LENGTH: 107
<212> TYPE: PRT
<213> ORGANISM: Artificial Sequence
```

```
<220> FEATURE:
<223> OTHER INFORMATION: mab14-hL3, the humanized light chain variable
      region of antibody mab14

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Gly Thr Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: mab14-hL4, the humanized light chain variable
      region of antibody mab14

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Gly Ala Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 33
<211> LENGTH: 107
<212> TYPE: PRT
<213> ORGANISM: Artificial Sequence
<220> FEATURE:
<223> OTHER INFORMATION: mab14-hL5, the humanized light chain variable
      region of antibody mab14

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Gly Thr Pro Lys Leu Leu Ile
        35                  40                  45
```

-continued

```
Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: mab14-hL6, the humanized light chain variable
      region of antibody mab14

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Thr Pro Lys Leu Leu Ile
            35                  40                  45

Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 35
<211> LENGTH: 126
<212> TYPE: PRT
<213> ORGANISM: Artificial Sequence
<220> FEATURE:
<223> OTHER INFORMATION: mab14-hH1, the humanized heavy chain variable
      region of antibody mab14

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
                20                  25                  30

Trp Ile Asn Trp Val Arg Gln Ala Pro Gly Gln Gly Leu Glu Trp Met
            35                  40                  45

Gly Asn Ile Tyr Pro Ser Ser Ile Ser Thr Asn Tyr Asn Glu Lys Phe
    50                  55                  60

Lys Thr Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
            100                 105                 110

Phe Gly Tyr Trp Gly Gln Gly Thr Leu Val Thr Val Ser Ser
            115                 120                 125
```

-continued

<210> SEQ ID NO 36
<211> LENGTH: 126
<212> TYPE: PRT
<213> ORGANISM: Artificial Sequence
<220> FEATURE:
<223> OTHER INFORMATION: mab14-hH2, the humanized heavy chain variable
      region of antibody mab14

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
                20                  25                  30

Trp Ile Asn Trp Val Lys Gln Ala Pro Gly Gln Gly Leu Glu Trp Ile
            35                  40                  45

Gly Asn Ile Tyr Pro Ser Ser Ile Ser Thr Asn Tyr Asn Glu Lys Phe
        50                  55                  60

Lys Thr Lys Ala Thr Leu Thr Val Asp Lys Ser Thr Ser Thr Val Tyr
65                  70                  75                  80

Met Glu Phe Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
            100                 105                 110

Phe Gly Tyr Trp Gly Gln Gly Thr Leu Val Thr Val Ser Ser
        115                 120                 125

<210> SEQ ID NO 37
<211> LENGTH: 126
<212> TYPE: PRT
<213> ORGANISM: Artificial Sequence
<220> FEATURE:
<223> OTHER INFORMATION: mab14-hH3, the humanized heavy chain variable
      region of antibody mab14

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
                20                  25                  30

Trp Ile Asn Trp Val Arg Gln Ala Pro Gly Gln Gly Leu Glu Trp Met
            35                  40                  45

Gly Asn Ile Tyr Pro Ser Ser Ile Ser Thr Asn Tyr Asn Glu Lys Phe
        50                  55                  60

Lys Thr Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
            100                 105                 110

Phe Gly Tyr Trp Gly Gln Gly Thr Leu Val Thr Val Ser Ser
        115                 120                 125

<210> SEQ ID NO 38
<211> LENGTH: 126
<212> TYPE: PRT
<213> ORGANISM: Artificial Sequence
<220> FEATURE:
<223> OTHER INFORMATION: mab14-hH4, the humanized heavy chain variable
      region of antibody mab14

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Ser Ile Ser Thr Asn Tyr Asn Glu Lys Phe
    50                  55                  60

Lys Thr Arg Ala Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
                100                 105                 110

Phe Gly Tyr Trp Gly Gln Gly Thr Leu Val Thr Val Ser Ser
        115                 120                 125
```

<210> SEQ ID NO 39
<211> LENGTH: 126
<212> TYPE: PRT
<213> ORGANISM: Artificial Sequence
<220> FEATURE:
<223> OTHER INFORMATION: mab14-hH5, the humanized heavy chain variable
      region of antibody mab14

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Ser Ile Ser Thr Asn Tyr Asn Glu Lys Phe
    50                  55                  60

Lys Thr Arg Ala Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
                100                 105                 110

Phe Gly Tyr Trp Gly Gln Gly Thr Leu Val Thr Val Ser Ser
        115                 120                 125
```

<210> SEQ ID NO 40
<211> LENGTH: 126
<212> TYPE: PRT
<213> ORGANISM: Artificial Sequence
<220> FEATURE:
<223> OTHER INFORMATION: mab14-hH6, the humanized heavy chain variable
      region of antibody mab14

<400> SEQUENCE: 40

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
            20                  25                  30

Trp Ile Asn Trp Val Lys Gln Ala Pro Gly Gln Gly Leu Glu Trp Ile
```

-continued

```
            35                    40                    45

Gly Asn Ile Tyr Pro Ser Ser Ile Ser Thr Asn Tyr Asn Glu Lys Phe
    50                    55                    60

Lys Thr Arg Ala Thr Leu Thr Val Asp Thr Ser Thr Ser Thr Val Tyr
65                    70                    75                    80

Met Glu Leu Ser Ser Leu Arg Ser Glu Asp Thr Ala Val Tyr Tyr Cys
                  85                    90                    95

Ala Arg Ser Glu Gly Thr Tyr Tyr Gly Gly Arg Tyr Glu Gly Asp Trp
              100                   105                   110

Phe Gly Tyr Trp Gly Gln Gly Thr Leu Val Thr Val Ser Ser
        115                   120                   125
```

```
<210> SEQ ID NO 41
<211> LENGTH: 126
<212> TYPE: PRT
<213> ORGANISM: Artificial Sequence
<220> FEATURE:
<223> OTHER INFORMATION: mab14-hH7, the humanized heavy chain variable
      region of antibody mab14

<400> SEQUENCE: 41

Gln Val Gln Leu Val Gln Ser Gly Ala Glu Val Lys Lys Pro Gly Ala
1                   5                     10                    15

Ser Val Lys Val Ser Cys Lys Ala Ser Gly Tyr Asn Phe Asn Ile Tyr
                  20                    25                    30

Trp Ile Asn Trp Val Lys Gln Ala Pro Gly Gln Gly Leu Glu Trp Ile
              35                    40                    45

Gly Asn Ile Tyr Pro Ser Ser Ile Ser Thr Asn Tyr Asn Glu Lys Phe
    50                    55                    60

Lys Thr Lys Ala Thr Leu Thr Val Asp Thr Ser Thr Ser Thr Val Tyr
65                    70                    75                    80

Met Glu Leu Ser Ser Leu Arg Ser Glu Asp Thr Ala Val Tyr Tyr Cys
                  85                    90                    95

Ala Arg Ser Glu Gly Thr Tyr Tyr Gly Gly Arg Tyr Glu Gly Asp Trp
              100                   105                   110

Phe Gly Tyr Trp Gly Gln Gly Thr Leu Val Thr Val Ser Ser
        115                   120                   125
```

```
<210> SEQ ID NO 42
<211> LENGTH: 214
<212> TYPE: PRT
<213> ORGANISM: Artificial Sequence
<220> FEATURE:
<223> OTHER INFORMATION: Light chain of amino acid sequence of humanized
      mab14-h5 antibody

<400> SEQUENCE: 42

Asp Ile Gln Met Thr Gln Ser Pro Ser Ser Leu Ser Ala Ser Val Gly
1                   5                     10                    15

Asp Arg Val Thr Ile Thr Cys Arg Ala Ser Gln Asp Ile Arg Asn Tyr
                  20                    25                    30

Leu Asn Trp Tyr Gln Gln Lys Pro Gly Gly Thr Val Lys Leu Leu Ile
              35                    40                    45

Tyr Phe Thr Ser Thr Leu His Ser Gly Val Pro Ser Arg Phe Ser Gly
    50                    55                    60

Ser Gly Ser Gly Thr Asp Tyr Thr Leu Thr Ile Ser Ser Leu Gln Pro
65                    70                    75                    80

Glu Asp Phe Ala Thr Tyr Tyr Cys Gln Gln Gly Asn Thr Leu Pro Trp
```

```
                    85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 43
<211> LENGTH: 453
<212> TYPE: PRT
<213> ORGANISM: Artificial Sequence
<220> FEATURE:
<223> OTHER INFORMATION: Heavy chain of amino acid sequence of humanized
      mab14-h5 antibody

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Asn Ile Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Ser Ile Ser Thr Asn Tyr Asn Glu Lys Phe
    50                  55                  60

Lys Thr Arg Ala Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Gly Thr Tyr Tyr Gly Gly Arg Tyr Glu Gly Asp Trp
            100                 105                 110

Phe Gly Tyr Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
    210                 215                 220
```

-continued

```
Glu Ser Lys Tyr Gly Pro Pro Cys Pro Pro Cys Pro Ala Pro Glu Phe
225             230             235             240

Leu Gly Gly Pro Ser Val Phe Leu Phe Pro Pro Lys Pro Lys Asp Thr
                245             250             255

Leu Met Ile Ser Arg Thr Pro Glu Val Thr Cys Val Val Val Asp Val
                260             265             270

Ser Gln Glu Asp Pro Glu Val Gln Phe Asn Trp Tyr Val Asp Gly Val
            275             280             285

Glu Val His Asn Ala Lys Thr Lys Pro Arg Glu Glu Gln Phe Asn Ser
            290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Gly Leu Pro Ser
                325             330             335

Ser Ile Glu Lys Thr Ile Ser Lys Ala Lys Gly Gln Pro Arg Glu Pro
                340             345             350

Gln Val Tyr Thr Leu Pro Pro Ser Gln Glu Glu Met Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Arg Leu
                405             410             415

Thr Val Asp Lys Ser Arg Trp Gln Glu Gly Asn Val Phe Ser Cys Ser
                420             425             430

Val Met His Glu Ala Leu His Asn His Tyr Thr Gln Lys Ser Leu Ser
        435             440             445

Leu Ser Leu Gly Lys
        450
```

```
<210> SEQ ID NO 44
<211> LENGTH: 214
<212> TYPE: PRT
<213> ORGANISM: Artificial Sequence
<220> FEATURE:
<223> OTHER INFORMATION: Light chain of amino acid sequence of humanized
      mab14-h12 antibody

<400> SEQUENCE: 44
```

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Ile Arg Asn Tyr
                20              25              30

Leu Asn Trp Tyr Gln Gln Lys Pro Gly Gly Thr Pro Lys Leu Leu Ile
        35              40              45

Tyr Phe Thr Ser Thr Leu His Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Gly Asn Thr Leu Pro Trp
                85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 45
<211> LENGTH: 214
<212> TYPE: PRT
<213> ORGANISM: Artificial Sequence
<220> FEATURE:
<223> OTHER INFORMATION: Light chain of amino acid sequence of humanized
      mab14-h13 antibody

<400> SEQUENCE: 45
```

```
Asp Ile Gln Met Thr Gln Ser Pro Ser Ser Leu Ser Ala Ser Val Gly
1                 5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Gly Ala Pro Lys Leu Leu Ile
            35                  40                  45

Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 46
<211> LENGTH: 214
<212> TYPE: PRT
<213> ORGANISM: Artificial Sequence
<220> FEATURE:
<223> OTHER INFORMATION: Light chain of amino acid sequence of humanized
```

-continued mab14-h14 antibody

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Gly Thr Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 214
<212> TYPE: PRT
<213> ORGANISM: Artificial Sequence
<220> FEATURE:
<223> OTHER INFORMATION: Light chain of amino acid sequence of humanized
      mab14-h15 antibody

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Thr Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

-continued

```
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 48
<211> LENGTH: 214
<212> TYPE: PRT
<213> ORGANISM: Artificial Sequence
<220> FEATURE:
<223> OTHER INFORMATION: Light chain of amino acid sequence of humanized
      mab14-h16 antibody

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Phe Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 49
<211> LENGTH: 21
<212> TYPE: DNA
<213> ORGANISM: Artificial Sequence
<220> FEATURE:
```

-continued

<223> OTHER INFORMATION: Sequencing primer p63a-SEQ

<400> SEQUENCE: 49
cacaggtgtc cactcccagg t                                                                  21

<210> SEQ ID NO 50
<211> LENGTH: 481
<212> TYPE: PRT
<213> ORGANISM: Artificial Sequence
<220> FEATURE:
<223> OTHER INFORMATION: antibody LB501 light chain sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Phe Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Val Gln
            115                 120                 125

Ser Gly Ala Glu Val Lys Lys Pro Gly Ala Ser Val Lys Val Ser Cys
        130                 135                 140

Lys Ala Ser Gly Tyr Asn Phe Asn Ile Tyr Trp Ile Asn Trp Val Arg
145                 150                 155                 160

Gln Ala Pro Gly Gln Gly Leu Glu Trp Ile Gly Asn Ile Tyr Pro Ser
                165                 170                 175

Ser Ile Ser Thr Asn Tyr Asn Glu Lys Phe Lys Thr Arg Ala Thr Leu
            180                 185                 190

Thr Val Asp Lys Ser Thr Ser Thr Val Tyr Met Glu Leu Ser Ser Leu
            195                 200                 205

Arg Ser Glu Asp Thr Ala Val Tyr Tyr Cys Ala Arg Ser Glu Gly Thr
        210                 215                 220

Tyr Tyr Gly Gly Arg Tyr Glu Gly Asp Trp Phe Gly Tyr Trp Gly Gln
225                 230                 235                 240

Gly Thr Leu Val Thr Val Ser Ser Gly Gly Gly Gly Ser Gly Gly Gly
            245                 250                 255

Gly Ser Gly Gly Gly Gly Ser Glu Ile Val Leu Thr Gln Ser Pro Ala
            260                 265                 270

Thr Leu Ser Leu Ser Pro Gly Glu Arg Ala Thr Leu Ser Cys Arg Ala
        275                 280                 285

Ser Lys Gly Val Ser Thr Ser Gly Tyr Ser Tyr Leu His Trp Tyr Gln
    290                 295                 300

Gln Lys Pro Gly Gln Ala Pro Arg Leu Leu Ile Tyr Leu Ala Ser Tyr
305                 310                 315                 320

Leu Glu Ser Gly Val Pro Ala Arg Phe Ser Gly Ser Gly Ser Gly Thr
                325                 330                 335

-continued

```
Asp Phe Thr Leu Thr Ile Ser Ser Leu Glu Pro Glu Asp Phe Ala Val
        340             345             350

Tyr Tyr Cys Gln His Ser Arg Asp Leu Pro Leu Thr Phe Gly Gly Gly
        355             360             365

Thr Lys Val Glu Ile Lys Arg Thr Val Ala Ala Pro Ser Val Phe Ile
        370             375             380

Phe Pro Pro Ser Asp Glu Gln Leu Lys Ser Gly Thr Ala Ser Val Val
385             390             395             400

Cys Leu Leu Asn Asn Phe Tyr Pro Arg Glu Ala Lys Val Gln Trp Lys
                405             410             415

Val Asp Asn Ala Leu Gln Ser Gly Asn Ser Gln Glu Ser Val Thr Glu
            420             425             430

Gln Asp Ser Lys Asp Ser Thr Tyr Ser Leu Ser Ser Thr Leu Thr Leu
        435             440             445

Ser Lys Ala Asp Tyr Glu Lys His Lys Val Tyr Ala Cys Glu Val Thr
    450             455             460

His Gln Gly Leu Ser Ser Pro Val Thr Lys Ser Phe Asn Arg Gly Glu
465             470             475             480

Cys
```

```
<210> SEQ ID NO 51
<211> LENGTH: 447
<212> TYPE: PRT
<213> ORGANISM: Artificial Sequence
<220> FEATURE:
<223> OTHER INFORMATION: antibody LB501 heavy chain sequence (Pem heavy
      chain)

<400> SEQUENCE: 51

Gln Val Gln Leu Val Gln Ser Gly Val Glu Val Lys Lys Pro Gly Ala
1               5               10              15

Ser Val Lys Val Ser Cys Lys Ala Ser Gly Tyr Thr Phe Thr Asn Tyr
            20              25              30

Tyr Met Tyr Trp Val Arg Gln Ala Pro Gly Gln Gly Leu Glu Trp Met
        35              40              45

Gly Gly Ile Asn Pro Ser Asn Gly Gly Thr Asn Phe Asn Glu Lys Phe
    50              55              60

Lys Asn Arg Val Thr Leu Thr Thr Asp Ser Ser Thr Thr Thr Ala Tyr
65              70              75              80

Met Glu Leu Lys Ser Leu Gln Phe Asp Asp Thr Ala Val Tyr Tyr Cys
                85              90              95

Ala Arg Arg Asp Tyr Arg Phe Asp Met Gly Phe Asp Tyr Trp Gly Gln
            100             105             110

Gly Thr Thr Val Thr Val Ser Ser Ala Ser Thr Lys Gly Pro Ser Val
        115             120             125

Phe Pro Leu Ala Pro Cys Ser Arg Ser Thr Ser Glu Ser Thr Ala Ala
        130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
                165             170             175

Leu Gln Ser Ser Gly Leu Tyr Ser Leu Ser Ser Val Val Thr Val Pro
            180             185             190

Ser Ser Ser Leu Gly Thr Lys Thr Tyr Thr Cys Asn Val Asp His Lys
        195             200             205
```

```
Pro Ser Asn Thr Lys Val Asp Lys Arg Val Glu Ser Lys Tyr Gly Pro
    210             215             220
```

```
Pro Cys Pro Pro Cys Pro Ala Pro Glu Phe Leu Gly Gly Pro Ser Val
225             230             235             240
```

```
Phe Leu Phe Pro Pro Lys Pro Lys Asp Thr Leu Met Ile Ser Arg Thr
            245             250             255
```

```
Pro Glu Val Thr Cys Val Val Val Asp Val Ser Gln Glu Asp Pro Glu
            260             265             270
```

```
Val Gln Phe Asn Trp Tyr Val Asp Gly Val Glu Val His Asn Ala Lys
            275             280             285
```

```
Thr Lys Pro Arg Glu Glu Gln Phe Asn Ser Thr Tyr Arg Val Val Ser
    290             295             300
```

```
Val Leu Thr Val Leu His Gln Asp Trp Leu Asn Gly Lys Glu Tyr Lys
305             310             315             320
```

```
Cys Lys Val Ser Asn Lys Gly Leu Pro Ser Ser Ile Glu Lys Thr Ile
            325             330             335
```

```
Ser Lys Ala Lys Gly Gln Pro Arg Glu Pro Gln Val Tyr Thr Leu Pro
            340             345             350
```

```
Pro Ser Gln Glu Glu Met Thr Lys Asn Gln Val Ser Leu Thr Cys Leu
            355             360             365
```

```
Val Lys Gly Phe Tyr Pro Ser Asp Ile Ala Val Glu Trp Glu Ser Asn
    370             375             380
```

```
Gly Gln Pro Glu Asn Asn Tyr Lys Thr Thr Pro Pro Val Leu Asp Ser
385             390             395             400
```

```
Asp Gly Ser Phe Phe Leu Tyr Ser Arg Leu Thr Val Asp Lys Ser Arg
            405             410             415
```

```
Trp Gln Glu Gly Asn Val Phe Ser Cys Ser Val Met His Glu Ala Leu
            420             425             430
```

```
His Asn His Tyr Thr Gln Lys Ser Leu Ser Leu Ser Leu Gly Lys
            435             440             445
```

<210> SEQ ID NO 52
<211> LENGTH: 218
<212> TYPE: PRT
<213> ORGANISM: Artificial Sequence
<220> FEATURE:
<223> OTHER INFORMATION: antibody LB502 light chain sequence (Pem light
      chain)

<400> SEQUENCE: 52

```
Glu Ile Val Leu Thr Gln Ser Pro Ala Thr Leu Ser Leu Ser Pro Gly
1               5               10              15
```

```
Glu Arg Ala Thr Leu Ser Cys Arg Ala Ser Lys Gly Val Ser Thr Ser
            20              25              30
```

```
Gly Tyr Ser Tyr Leu His Trp Tyr Gln Gln Lys Pro Gly Gln Ala Pro
            35              40              45
```

```
Arg Leu Leu Ile Tyr Leu Ala Ser Tyr Leu Glu Ser Gly Val Pro Ala
    50              55              60
```

```
Arg Phe Ser Gly Ser Gly Ser Gly Thr Asp Phe Thr Leu Thr Ile Ser
65              70              75              80
```

```
Ser Leu Glu Pro Glu Asp Phe Ala Val Tyr Tyr Cys Gln His Ser Arg
            85              90              95
```

```
Asp Leu Pro Leu Thr Phe Gly Gly Gly Thr Lys Val Glu Ile Lys Arg
            100             105             110
```

```
Thr Val Ala Ala Pro Ser Val Phe Ile Phe Pro Pro Ser Asp Glu Gln
            115             120             125
```

-continued

```
Leu Lys Ser Gly Thr Ala Ser Val Val Cys Leu Leu Asn Asn Phe Tyr
    130               135               140

Pro Arg Glu Ala Lys Val Gln Trp Lys Val Asp Asn Ala Leu Gln Ser
145               150               155               160

Gly Asn Ser Gln Glu Ser Val Thr Glu Gln Asp Ser Lys Asp Ser Thr
                165               170               175

Tyr Ser Leu Ser Ser Thr Leu Thr Leu Ser Lys Ala Asp Tyr Glu Lys
            180               185               190

His Lys Val Tyr Ala Cys Glu Val Thr His Gln Gly Leu Ser Ser Pro
            195               200               205

Val Thr Lys Ser Phe Asn Arg Gly Glu Cys
    210               215
```

```
<210> SEQ ID NO 53
<211> LENGTH: 710
<212> TYPE: PRT
<213> ORGANISM: Artificial Sequence
<220> FEATURE:
<223> OTHER INFORMATION: antibody LB502 heavy chain sequence

<400> SEQUENCE: 53
```

```
Asp Ile Gln Met Thr Gln Ser Pro Ser Ser Leu Ser Ala Ser Val Gly
1               5               10               15

Asp Arg Val Thr Ile Thr Cys Arg Ala Ser Gln Asp Ile Arg Asn Tyr
            20               25               30

Leu Asn Trp Tyr Gln Gln Lys Pro Gly Lys Ala Pro Lys Leu Leu Ile
        35               40               45

Tyr Phe Thr Ser Thr Leu His Ser Gly Val Pro Ser Arg Phe Ser Gly
    50               55               60

Ser Gly Ser Gly Thr Asp Phe Thr Leu Thr Ile Ser Ser Leu Gln Pro
65               70               75               80

Glu Asp Phe Ala Thr Tyr Tyr Cys Gln Gln Gly Asn Thr Leu Pro Trp
            85               90               95

Thr Phe Gly Gly Gly Thr Lys Val Glu Ile Lys Gly Gly Gly Gly Ser
            100               105               110

Gly Gly Gly Gly Ser Gly Gly Gly Gly Ser Gln Val Gln Leu Val Gln
        115               120               125

Ser Gly Ala Glu Val Lys Lys Pro Gly Ala Ser Val Lys Val Ser Cys
    130               135               140

Lys Ala Ser Gly Tyr Asn Phe Asn Ile Tyr Trp Ile Asn Trp Val Arg
145               150               155               160

Gln Ala Pro Gly Gln Gly Leu Glu Trp Ile Gly Asn Ile Tyr Pro Ser
            165               170               175

Ser Ile Ser Thr Asn Tyr Asn Glu Lys Phe Lys Thr Arg Ala Thr Leu
            180               185               190

Thr Val Asp Lys Ser Thr Ser Thr Val Tyr Met Glu Leu Ser Ser Leu
            195               200               205

Arg Ser Glu Asp Thr Ala Val Tyr Tyr Cys Ala Arg Ser Glu Gly Thr
    210               215               220

Tyr Tyr Gly Gly Arg Tyr Glu Gly Asp Trp Phe Gly Tyr Trp Gly Gln
225               230               235               240

Gly Thr Leu Val Thr Val Ser Ser Gly Gly Gly Ser Gly Gly Gly
            245               250               255

Gly Ser Gly Gly Gly Gly Ser Gln Val Gln Leu Val Gln Ser Gly Val
        260               265               270
```

```
Glu Val Lys Lys Pro Gly Ala Ser Val Lys Val Ser Cys Lys Ala Ser
    275             280             285

Gly Tyr Thr Phe Thr Asn Tyr Tyr Met Tyr Trp Val Arg Gln Ala Pro
    290             295             300

Gly Gln Gly Leu Glu Trp Met Gly Gly Ile Asn Pro Ser Asn Gly Gly
305             310             315             320

Thr Asn Phe Asn Glu Lys Phe Lys Asn Arg Val Thr Leu Thr Thr Asp
                325             330             335

Ser Ser Thr Thr Thr Ala Tyr Met Glu Leu Lys Ser Leu Gln Phe Asp
            340             345             350

Asp Thr Ala Val Tyr Tyr Cys Ala Arg Arg Asp Tyr Arg Phe Asp Met
        355             360             365

Gly Phe Asp Tyr Trp Gly Gln Gly Thr Thr Val Thr Val Ser Ser Ala
    370             375             380

Ser Thr Lys Gly Pro Ser Val Phe Pro Leu Ala Pro Cys Ser Arg Ser
385             390             395             400

Thr Ser Glu Ser Thr Ala Ala Leu Gly Cys Leu Val Lys Asp Tyr Phe
                405             410             415

Pro Glu Pro Val Thr Val Ser Trp Asn Ser Gly Ala Leu Thr Ser Gly
            420             425             430

Val His Thr Phe Pro Ala Val Leu Gln Ser Ser Gly Leu Tyr Ser Leu
        435             440             445

Ser Ser Val Val Thr Val Pro Ser Ser Ser Leu Gly Thr Lys Thr Tyr
    450             455             460

Thr Cys Asn Val Asp His Lys Pro Ser Asn Thr Lys Val Asp Lys Arg
465             470             475             480

Val Glu Ser Lys Tyr Gly Pro Pro Cys Pro Pro Cys Pro Ala Pro Glu
                485             490             495

Phe Leu Gly Gly Pro Ser Val Phe Leu Phe Pro Pro Lys Pro Lys Asp
            500             505             510

Thr Leu Met Ile Ser Arg Thr Pro Glu Val Thr Cys Val Val Val Asp
        515             520             525

Val Ser Gln Glu Asp Pro Glu Val Gln Phe Asn Trp Tyr Val Asp Gly
    530             535             540

Val Glu Val His Asn Ala Lys Thr Lys Pro Arg Glu Glu Gln Phe Asn
545             550             555             560

Ser Thr Tyr Arg Val Val Ser Val Leu Thr Val Leu His Gln Asp Trp
                565             570             575

Leu Asn Gly Lys Glu Tyr Lys Cys Lys Val Ser Asn Lys Gly Leu Pro
            580             585             590

Ser Ser Ile Glu Lys Thr Ile Ser Lys Ala Lys Gly Gln Pro Arg Glu
        595             600             605

Pro Gln Val Tyr Thr Leu Pro Pro Ser Gln Glu Glu Met Thr Lys Asn
    610             615             620

Gln Val Ser Leu Thr Cys Leu Val Lys Gly Phe Tyr Pro Ser Asp Ile
625             630             635             640

Ala Val Glu Trp Glu Ser Asn Gly Gln Pro Glu Asn Asn Tyr Lys Thr
                645             650             655

Thr Pro Pro Val Leu Asp Ser Asp Gly Ser Phe Phe Leu Tyr Ser Arg
            660             665             670

Leu Thr Val Asp Lys Ser Arg Trp Gln Glu Gly Asn Val Phe Ser Cys
    675             680             685
```

-continued

```
Ser Val Met His Glu Ala Leu His Asn His Tyr Thr Gln Lys Ser Leu
    690             695             700

Ser Leu Ser Leu Gly Lys
705             710

<210> SEQ ID NO 54
<211> LENGTH: 482
<212> TYPE: PRT
<213> ORGANISM: Artificial Sequence
<220> FEATURE:
<223> OTHER INFORMATION: antibody LB503 light chain sequence

<400> SEQUENCE: 54

Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Gly Val Ser Thr Ser
            20              25              30

Gly Tyr Ser Tyr Leu His Trp Tyr Gln Gln Lys Pro Gly Gln Ala Pro
        35              40              45

Arg Leu Leu Ile Tyr Leu Ala Ser Tyr Leu Glu Ser Gly Val Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln His Ser Arg
            85              90              95

Asp Leu Pro Leu Thr Phe Gly Gly Gly Thr Lys Val Glu Ile Lys Arg
            100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
        195             200             205

Val Thr Lys Ser Phe Asn Arg Gly Glu Cys Ala Gly Gly Gly Gly Ser
    210             215             220

Gly Gly Gly Gly Ser Gly Gly Gly Ser Gln Val Gln Leu Val Gln
225             230             235             240

Ser Gly Ala Glu Val Lys Lys Pro Gly Ala Ser Val Lys Val Ser Cys
            245             250             255

Lys Ala Ser Gly Tyr Asn Phe Asn Ile Tyr Trp Ile Asn Trp Val Arg
            260             265             270

Gln Ala Pro Gly Gln Gly Leu Glu Trp Ile Gly Asn Ile Tyr Pro Ser
        275             280             285

Ser Ile Ser Thr Asn Tyr Asn Glu Lys Phe Lys Thr Arg Ala Thr Leu
    290             295             300

Thr Val Asp Lys Ser Thr Ser Thr Val Tyr Met Glu Leu Ser Ser Leu
305             310             315             320

Arg Ser Glu Asp Thr Ala Val Tyr Tyr Cys Ala Arg Ser Glu Gly Thr
            325             330             335
```

-continued

Tyr Tyr Gly Gly Arg Tyr Glu Gly Asp Trp Phe Gly Tyr Trp Gly Gln
            340                 345                 350

Gly Thr Leu Val Thr Val Ser Ser Gly Gly Gly Gly Ser Gly Gly Gly
            355                 360                 365

Gly Ser Gly Gly Gly Gly Ser Asp Ile Gln Met Thr Gln Ser Pro Ser
    370                 375                 380

Ser Leu Ser Ala Ser Val Gly Asp Arg Val Thr Ile Thr Cys Arg Ala
385                 390                 395                 400

Ser Gln Asp Ile Arg Asn Tyr Leu Asn Trp Tyr Gln Gln Lys Pro Gly
                405                 410                 415

Lys Ala Pro Lys Leu Leu Ile Tyr Phe Thr Ser Thr Leu His Ser Gly
            420                 425                 430

Val Pro Ser Arg Phe Ser Gly Ser Gly Ser Gly Thr Asp Phe Thr Leu
            435                 440                 445

Thr Ile Ser Ser Leu Gln Pro Glu Asp Phe Ala Thr Tyr Tyr Cys Gln
    450                 455                 460

Gln Gly Asn Thr Leu Pro Trp Thr Phe Gly Gly Gly Thr Lys Val Glu
465                 470                 475                 480

Ile Lys

<210> SEQ ID NO 55
<211> LENGTH: 710
<212> TYPE: PRT
<213> ORGANISM: Artificial Sequence
<220> FEATURE:
<223> OTHER INFORMATION: antibody LB504 heavy chain sequence

<400> SEQUENCE: 55

Gln Val Gln Leu Val Gln Ser Gly Val Glu Val Lys Lys Pro Gly Ala
1                   5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro

-continued

```
       210              215              220

Pro Cys Pro Pro Cys Pro Ala Pro Glu Phe Leu Gly Gly Pro Ser Val
225              230              235              240

Phe Leu Phe Pro Pro Lys Pro Lys Asp Thr Leu Met Ile Ser Arg Thr
            245              250              255

Pro Glu Val Thr Cys Val Val Val Asp Val Ser Gln Glu Asp Pro Glu
            260              265              270

Val Gln Phe Asn Trp Tyr Val Asp Gly Val Glu Val His Asn Ala Lys
        275              280              285

Thr Lys Pro Arg Glu Glu Gln Phe Asn Ser Thr Tyr Arg Val Val Ser
    290              295              300

Val Leu Thr Val Leu His Gln Asp Trp Leu Asn Gly Lys Glu Tyr Lys
305              310              315              320

Cys Lys Val Ser Asn Lys Gly Leu Pro Ser Ser Ile Glu Lys Thr Ile
            325              330              335

Ser Lys Ala Lys Gly Gln Pro Arg Glu Pro Gln Val Tyr Thr Leu Pro
            340              345              350

Pro Ser Gln Glu Glu Met Thr Lys Asn Gln Val Ser Leu Thr Cys Leu
            355              360              365

Val Lys Gly Phe Tyr Pro Ser Asp Ile Ala Val Glu Trp Glu Ser Asn
        370              375              380

Gly Gln Pro Glu Asn Asn Tyr Lys Thr Thr Pro Pro Val Leu Asp Ser
385              390              395              400

Asp Gly Ser Phe Phe Leu Tyr Ser Arg Leu Thr Val Asp Lys Ser Arg
            405              410              415

Trp Gln Glu Gly Asn Val Phe Ser Cys Ser Val Met His Glu Ala Leu
            420              425              430

His Asn His Tyr Thr Gln Lys Ser Leu Ser Leu Ser Leu Gly Ala Gly
        435              440              445

Gly Gly Gly Ser Gly Gly Gly Gly Ser Gly Gly Gly Ser Gln Val
    450              455              460

Gln Leu Val Gln Ser Gly Ala Glu Val Lys Lys Pro Gly Ala Ser Val
465              470              475              480

Lys Val Ser Cys Lys Ala Ser Gly Tyr Asn Phe Asn Ile Tyr Trp Ile
            485              490              495

Asn Trp Val Arg Gln Ala Pro Gly Gln Gly Leu Glu Trp Ile Gly Asn
            500              505              510

Ile Tyr Pro Ser Ser Ile Ser Thr Asn Tyr Asn Glu Lys Phe Lys Thr
        515              520              525

Arg Ala Thr Leu Thr Val Asp Lys Ser Thr Ser Thr Val Tyr Met Glu
    530              535              540

Leu Ser Ser Leu Arg Ser Glu Asp Thr Ala Val Tyr Tyr Cys Ala Arg
545              550              555              560

Ser Glu Gly Thr Tyr Tyr Gly Gly Arg Tyr Glu Gly Asp Trp Phe Gly
            565              570              575

Tyr Trp Gly Gln Gly Thr Leu Val Thr Val Ser Ser Gly Gly Gly Gly
            580              585              590

Ser Gly Gly Gly Gly Ser Gly Gly Gly Gly Ser Asp Ile Gln Met Thr
        595              600              605

Gln Ser Pro Ser Ser Leu Ser Ala Ser Val Gly Asp Arg Val Thr Ile
    610              615              620

Thr Cys Arg Ala Ser Gln Asp Ile Arg Asn Tyr Leu Asn Trp Tyr Gln
625              630              635              640
```

-continued

Gln Lys Pro Gly Lys Ala Pro Lys Leu Leu Ile Tyr Phe Thr Ser Thr
              645             650             655

Leu His Ser Gly Val Pro Ser Arg Phe Ser Gly Ser Gly Ser Gly Thr
              660             665             670

Asp Phe Thr Leu Thr Ile Ser Ser Leu Gln Pro Glu Asp Phe Ala Thr
              675             680             685

Tyr Tyr Cys Gln Gln Gly Asn Thr Leu Pro Trp Thr Phe Gly Gly Gly
          690             695             700

Thr Lys Val Glu Ile Lys
705             710

<210> SEQ ID NO 56
<211> LENGTH: 214
<212> TYPE: PRT
<213> ORGANISM: Artificial Sequence
<220> FEATURE:
<223> OTHER INFORMATION: antibody LB506 light chain sequence (Nivo light
      chain)

<400> SEQUENCE: 56

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
              20              25              30

Leu Ala Trp Tyr Gln Gln Lys Pro Gly Gln Ala Pro Arg Leu Leu Ile
          35              40              45

Tyr Asp Ala Ser Asn Arg Ala Thr Gly Ile Pro Ala Arg Phe Ser Gly
      50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Ser Ser Asn Trp Pro Arg
              85              90              95

Thr Phe Gly Gln Gly Thr Lys Val Glu Ile Lys Arg Thr Val Ala Ala
              100             105             110

Pro Ser Val Phe Ile Phe Pro Pro Ser Asp Glu Gln Leu Lys Ser Gly
          115             120             125

Thr Ala Ser Val Val Cys Leu Leu Asn Asn Phe Tyr Pro Arg Glu Ala
      130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
              165             170             175

Ser Thr Leu Thr Leu Ser Lys Ala Asp Tyr Glu Lys His Lys Val Tyr
              180             185             190

Ala Cys Glu Val Thr His Gln Gly Leu Ser Ser Pro Val Thr Lys Ser
          195             200             205

Phe Asn Arg Gly Glu Cys
      210

<210> SEQ ID NO 57
<211> LENGTH: 703
<212> TYPE: PRT
<213> ORGANISM: Artificial Sequence
<220> FEATURE:
<223> OTHER INFORMATION: antibody LB506 heavy chain sequence

<400> SEQUENCE: 57

-continued

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
```

-continued

```
               420            425               430
Ser Leu Ser Leu Ser Leu Gly Ala Gly Gly Gly Gly Ser Gly Gly Gly
         435            440               445

Gly Ser Gly Gly Gly Gly Ser Gln Val Gln Leu Val Gln Ser Gly Ala
    450                455            460

Glu Val Lys Lys Pro Gly Ala Ser Val Lys Val Ser Cys Lys Ala Ser
465                470            475                480

Gly Tyr Asn Phe Asn Ile Tyr Trp Ile Asn Trp Val Arg Gln Ala Pro
                485            490               495

Gly Gln Gly Leu Glu Trp Ile Gly Asn Ile Tyr Pro Ser Ser Ile Ser
         500            505               510

Thr Asn Tyr Asn Glu Lys Phe Lys Thr Arg Ala Thr Leu Thr Val Asp
         515            520            525

Lys Ser Thr Ser Thr Val Tyr Met Glu Leu Ser Ser Leu Arg Ser Glu
    530            535            540

Asp Thr Ala Val Tyr Tyr Cys Ala Arg Ser Glu Gly Thr Tyr Tyr Gly
545                550            555                560

Gly Arg Tyr Glu Gly Asp Trp Phe Gly Tyr Trp Gly Gln Gly Thr Leu
         565            570            575

Val Thr Val Ser Ser Gly Gly Gly Ser Gly Gly Gly Gly Ser Gly
         580            585               590

Gly Gly Gly Ser Asp Ile Gln Met Thr Gln Ser Pro Ser Ser Leu Ser
         595            600            605

Ala Ser Val Gly Asp Arg Val Thr Ile Thr Cys Arg Ala Ser Gln Asp
    610            615            620

Ile Arg Asn Tyr Leu Asn Trp Tyr Gln Gln Lys Pro Gly Lys Ala Pro
625                630            635                640

Lys Leu Leu Ile Tyr Phe Thr Ser Thr Leu His Ser Gly Val Pro Ser
                645            650               655

Arg Phe Ser Gly Ser Gly Ser Gly Thr Asp Phe Thr Leu Thr Ile Ser
         660            665            670

Ser Leu Gln Pro Glu Asp Phe Ala Thr Tyr Tyr Cys Gln Gln Gly Asn
         675            680            685

Thr Leu Pro Trp Thr Phe Gly Gly Gly Thr Lys Val Glu Ile Lys
    690            695            700
```

<210> SEQ ID NO 58
<211> LENGTH: 5
<212> TYPE: PRT
<213> ORGANISM: Artificial Sequence
<220> FEATURE:
<223> OTHER INFORMATION: Linker 1

<400> SEQUENCE: 58

```
Gly Gly Gly Gly Ser
1               5
```

<210> SEQ ID NO 59
<211> LENGTH: 10
<212> TYPE: PRT
<213> ORGANISM: Artificial Sequence
<220> FEATURE:
<223> OTHER INFORMATION: Linker 2

<400> SEQUENCE: 59

```
Gly Gly Gly Gly Ser Gly Gly Gly Gly Ser
1               5                   10
```

<210> SEQ ID NO 60
<211> LENGTH: 15
<212> TYPE: PRT
<213> ORGANISM: Artificial Sequence
<220> FEATURE:
<223> OTHER INFORMATION: Linker 3

<400> SEQUENCE: 60

Gly Gly Gly Gly Ser Gly Gly Gly Gly Ser Gly Gly Gly Gly Ser
1               5                  10                  15

<210> SEQ ID NO 61
<211> LENGTH: 20
<212> TYPE: PRT
<213> ORGANISM: Artificial Sequence
<220> FEATURE:
<223> OTHER INFORMATION: Linker 4

<400> SEQUENCE: 61

Gly Gly Gly Gly Ser Gly Gly Gly Gly Ser Gly Gly Gly Gly Ser Gly
1               5                  10                  15

Gly Gly Gly Ser
            20

<210> SEQ ID NO 62
<211> LENGTH: 503
<212> TYPE: PRT
<213> ORGANISM: Macaca fascicularis

<400> SEQUENCE: 62

Met Glu Pro Ala Gly Pro Ala Pro Gly Arg Leu Gly Pro Leu Leu Cys
1               5                  10                  15

Leu Leu Leu Thr Ala Ser Cys Ala Trp Ser Gly Val Leu Gly Glu Glu
            20                  25                  30

Glu Leu Gln Val Ile Gln Pro Glu Lys Ser Val Ser Val Ala Ala Gly
        35                  40                  45

Asp Ser Ala Thr Leu Asn Cys Thr Val Ser Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Leu Lys Glu Gly His Phe Pro Arg Val Thr Ala Val Ser Asp Pro
            85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Leu Lys Ser Gly Ala Gly Thr Glu Leu Ser Val Arg
        130                 135                 140

Ala Lys Pro Ser Ala Pro Val Val Ser Gly Pro Ala Val Arg Ala Thr
145                 150                 155                 160

Ala Glu His Thr Val Ser Phe Thr Cys Glu Ser His Gly Phe Ser Pro
            165                 170                 175

Arg Asp Ile Thr Leu Lys Trp Phe Lys Asn Gly Asn Glu Leu Ser Asp
            180                 185                 190

Val Gln Thr Asn Val Asp Pro Ala Gly Lys Ser Val Ser Tyr Ser Ile
        195                 200                 205

Arg Ser Thr Ala Arg Val Leu Leu Thr Arg Arg Asp Val His Ser Gln
    210                 215                 220

-continued

```
Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Phe Leu Glu
                245                 250                 255

Val Thr Gln Gln Ser Met Arg Ala Asp Asn Gln Val Asn Val Thr Cys
                260                 265                 270

Gln Val Thr Lys Phe Tyr Pro Gln Arg Leu Gln Leu Thr Trp Leu Glu
                275                 280                 285

Asn Gly Asn Val Ser Arg Thr Glu Met Ala Ser Ala Leu Pro Glu Asn
                290                 295                 300

Lys Asp Gly Thr Tyr Asn Trp Thr Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Asn Lys Ser Phe Ser Val Lys Val Ser Ala His Pro
                340                 345                 350

Lys Glu Gln Gly Ser Asn Thr Ala Ala Glu Asn Thr Gly Thr Asn Glu
                355                 360                 365

Arg Asn Ile Tyr Ile Val Val Gly Val Val Cys Thr Leu Leu Val Ala
        370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
                420                 425                 430

Leu Pro Lys Gly Lys Lys Pro Ala Pro Arg Ala Ala Glu Pro Asn Asn
                435                 440                 445

His Thr Glu Gly Ala Ser Ile Gln Thr Ser Pro Gln Pro Ala Ser Glu
                450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
                500
```

```
<210> SEQ ID NO 63
<211> LENGTH: 503
<212> TYPE: PRT
<213> ORGANISM: Macaca fascicularis

<400> SEQUENCE: 63
```

```
Met Glu Pro Ala Gly Pro Ala Pro Gly Arg Leu Gly Pro Leu Leu Cys
1               5                   10                  15

Leu Leu Leu Thr Ala Ser Cys Ala Trp Ser Gly Val Leu Gly Glu Glu
                20                  25                  30

Glu Leu Gln Val Ile Gln Pro Glu Lys Ser Val Ser Val Ala Ala Gly
        35                  40                  45

Asp Ser Ala Thr Leu Asn Cys Thr Val Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Leu Lys Glu Gly His Phe Pro Arg Val Thr Pro Val Ser Asp Pro
                85                  90                  95
```

-continued

```
Thr Lys Arg Asn Asn Met Asp Phe Ser Ile His Ile Ser Asn Ile Thr
            100             105             110

Pro Ala Asp Ala Gly Thr Tyr Tyr Cys Val Lys Phe Arg Lys Gly Ser
            115             120             125

Pro Asp Val Glu Val Lys Ser Gly Ala Gly Thr Glu Leu Ser Val Arg
            130             135             140

Ala Lys Pro Ser Ala Pro Val Val Ser Gly Pro Ala Val Arg Ala Thr
145             150             155             160

Ala Glu His Thr Val Ser Phe Thr Cys Glu Ser His Gly Phe Ser Pro
                165             170             175

Arg Asp Ile Thr Leu Lys Trp Phe Lys Asn Gly Asn Glu Leu Ser Asp
                180             185             190

Phe Gln Thr Asn Val Asp Pro Ala Gly Lys Ser Val Ser Tyr Ser Ile
                195             200             205

Arg Ser Thr Ala Arg Val Val Leu Thr Arg Arg Asp Val His Ser Gln
            210             215             220

Val Ile Cys Glu Val Ala His Val Thr Leu Gln Gly Asp Pro Leu Arg
225             230             235             240

Gly Thr Ala Asn Leu Ser Glu Ala Ile Arg Val Pro Pro Phe Leu Glu
                245             250             255

Val Thr Gln Gln Ser Met Arg Ala Asp Asn Gln Val Asn Val Thr Cys
                260             265             270

Gln Val Thr Lys Phe Tyr Pro Gln Arg Leu Gln Leu Thr Trp Leu Glu
                275             280             285

Asn Gly Asn Val Ser Arg Thr Glu Met Ala Ser Ala Leu Pro Glu Asn
            290             295             300

Lys Asp Gly Thr Tyr Asn Trp Thr Ser Trp Leu Leu Val Asn Val Ser
305             310             315             320

Ala His Arg Asp Asp Val Lys Leu Thr Cys Gln Val Glu His Asp Gly
                325             330             335

Gln Pro Ala Val Asn Lys Ser Phe Ser Val Lys Val Ser Ala His Pro
                340             345             350

Lys Glu Gln Gly Ser Asn Thr Ala Ala Glu Asn Thr Gly Thr Asn Glu
                355             360             365

Arg Asn Ile Tyr Ile Val Val Gly Val Val Cys Thr Leu Leu Val Ala
            370             375             380

Leu Leu Met Ala Ala Leu Tyr Leu Val Arg Ile Arg Gln Lys Lys Ala
385             390             395             400

Gln Gly Ser Thr Ser Ser Thr Arg Leu His Glu Pro Glu Lys Asn Ala
                405             410             415

Arg Glu Ile Thr Gln Asp Thr Asn Asp Ile Thr Tyr Ala Asp Leu Asn
                420             425             430

Leu Pro Lys Gly Lys Lys Pro Ala Pro Arg Ala Ala Glu Pro Asn Asn
            435             440             445

His Thr Glu Tyr Ala Ser Ile Gln Thr Ser Pro Gln Pro Ala Ser Glu
            450             455             460

Asp Thr Leu Thr Tyr Ala Asp Leu Asp Met Val His Leu Asn Arg Thr
465             470             475             480

Pro Lys Gln Pro Ala Pro Lys Pro Glu Pro Ser Phe Ser Glu Tyr Ala
                485             490             495

Ser Val Gln Val Pro Arg Lys
            500
```

-continued

```
<210> SEQ ID NO 64
<211> LENGTH: 25
<212> TYPE: PRT
<213> ORGANISM: Artificial Sequence
<220> FEATURE:
<223> OTHER INFORMATION: Linker 5

<400> SEQUENCE: 64

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 65
<211> LENGTH: 30
<212> TYPE: PRT
<213> ORGANISM: Artificial Sequence
<220> FEATURE:
<223> OTHER INFORMATION: Linker 6

<400> SEQUENCE: 65

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 66
<211> LENGTH: 35
<212> TYPE: PRT
<213> ORGANISM: Artificial Sequence
<220> FEATURE:
<223> OTHER INFORMATION: Linker 7

<400> SEQUENCE: 66

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 67
<211> LENGTH: 40
<212> TYPE: PRT
<213> ORGANISM: Artificial Sequence
<220> FEATURE:
<223> OTHER INFORMATION: Linker 8

<400> SEQUENCE: 67

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 68
<211> LENGTH: 45
<212> TYPE: PRT
<213> ORGANISM: Artificial Sequence
<220> FEATURE:
<223> OTHER INFORMATION: Linker 9

<400> SEQUENCE: 68
```

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 69
<211> LENGTH: 50
<212> TYPE: PRT
<213> ORGANISM: Artificial Sequence
<220> FEATURE:
<223> OTHER INFORMATION: Linker 10

<400> SEQUENCE: 69

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

SIRPα-TARGETING ANTIBODY OR ANTIGEN BINDING FRAGMENT THEREOF, AND PREPARATION AND APPLICATION THEREOF

REFERENCE TO SEQUENCE LISTING

The Sequence Listing is submitted concurrently with the specification as an ASCII formatted text file via EFS-Web, with a file name of "P22414128US-2-SEQ-sub", a creation date of Aug. 7, 2025, and a size of 102,889 bytes. The Sequence Listing filed via EFS-Web is part of the specification and is incorporated in its entirety by reference herein.

The present application is a National Stage of International Application No. PCT/CN2021/081272, filed on Mar. 17, 2021, which claims the priority of Chinese patent application 2020102041302 filed on Mar. 20, 2020. The present application cites the full text of the aforementioned Chinese patent application.

TECHNICAL FIELD

The present disclosure relates to the field of biomedicine, and in particular to a Sirpα-targeting antibody or an antigen-binding fragment thereof, and a preparation method and application thereof, and the present disclosure further relates to a bispecific antibody including the Sirpα-targeting antibody or an antigen-binding fragment thereof.

BACKGROUND

The SIRP family is a transmembrane glycoprotein belonging to the immunoglobulin superfamily, and is generally divided into Sirpα, Sirpβ, and Sirpγ according to the different structures of transmembrane region and intracellular region. The extracellular region structures of the three are highly homologous, and they are all composed of three Ig-like domains. The intracellular regions of Sirpβ and Sirpγ are very short, with only six and four amino acids, respectively, and both have no signal motif interacting with phosphatase. However, four tyrosine residues in the cytoplasmic region of Sirpα (Signal regulatory protein α, also known as CD172α, SHPS-1, P84 or BIT) form two typical immune-receptor tyrosine-based inhibitory motifs (ITIMs), which can be phosphorylated to undergo an accumulation reaction, and then activated by cytosolic protein tyrosine phosphatase connected to itself, thereby regulating the growth and activation of cells. In myeloid cells, Sirpα often acts as an inhibitory receptor that inhibits activation of immune cells by recruiting SH2-domain-bearing tyrosine phosphatases. Sirpα was identified in the late 1990s and is expressed on the membrane surface of myeloid cells, including all types of macrophages, granulocytes, dendritic cells, and nerve cells, and expressed to a lesser extent on other cells. A gene encoding human Sirpα is a polymorphic gene that includes multiple variants. The most common protein variants are Sirpα-V1 and Sirpα-V2 (NCBI sequence number NP_542970 (P78324) and CAA71403). The polymorphism in human Sirpα can lead to the change of amino acids exposed on the surface, but does not affect the binding to CD47. The expression level of the Sirpα protein variant is different in populations of different races. In the populations of regions of Europe, Africa, America, and South Asia, the proportion of people with high expression of Sirpα-V2 is relatively low, accounting for only 8.6% in Africa; but its proportion in East Asians is very high, up to 41.3%. Currently, all of the existing anti-Sirpα antibodies are only aimed at a population with high expression of Sirpα-V1, but clinically, 20% of the population is of a non-V1 form, and the existing anti-Sirpα antibodies cannot meet the needs of this part of patients. For example, OSE-172 available from Boehringer Ingelheim, a drug against Sirpα, currently enters clinical trials (see WO2017178653A2). OSE-172 is a monoclonal antibody targeting Sirpα expressed in myeloid cells, which binds only to human Sirpα-V1, but not to human Sirpα-V2, and it can only treat patients with high expression of Sirpα-V1 when developed as a drug. Furthermore, OSE-172 does not bind to Sirpα derived from *cynomolgus* (cyno) (Cyno Sirpα), which brings inconvenience to the selection of primate *Macaca mulatta* in preclinical safety evaluation studies. In terms of the selectivity to Sirpβ, OSE-172 binds to Sirpβ, but the selectivity is not good enough. If it is used in the process of developing a clinical drug, there may be side effects caused by off-target effects, bringing about security issues.

The interaction between CD47 and Sirpα was first discovered in 1999, after which a large number of studies have confirmed that CD47 (also known as integrin-associated protein, IAP) is widely expressed on the surface of normal cells, and by binding to the Sirpα on the surface of macrophages, it releases a "don't eat me" signal, thereby protecting healthy cells from being "eaten" by the macrophages. Cancer cells also learn this mechanism: overexpression of CD47 on its surface allows macrophages to treat them as "normal cells", thereby evading macrophage-mediated phagocytic attack. After Sirpα binds to CD47, it leads to the aggregation of receptor molecules, and thus causes phosphorylation and activation of tyrosine and inhibits the accumulation of macrophage synaptic myosin. In this process, the Sirpα bearing the phosphorylated ITIM can recruit and activate tyrosine phosphatases SHP-1 and SHP-2, and transmit inhibition signals to inhibit the phagocytosis of macrophages, which eventually leads to the immune escape of tumor cells. Therefore, blocking the binding of Sirpα to CD47 can restore the relevant functions of macrophages, and finally achieve the effect of treating a tumor.

Moreover, CD47 also binds to another member of SIRP family, Sirpγ (also known as SIRPg, SIRPgamma, CD172g or SIRP beta 2) that is present on the surface of human T cells rather than on human myeloid cells. In contrast to the expression of Sirpα on the myeloid cells, Sirpγ is restrictedly expressed on T lymphocytes. Sirpγ is not expressed in mice. It has been shown by research that the Sirpγ-CD47 interaction mediates cell-cell adhesion, enhances superantigen-dependent T cell-mediated proliferation and co-stimulates T-cell activation (Piccio et al., Blood, 105: 6, 2005).

Due to the high sequence homology between Sirpα and Sirpγ, especially in the region that binds to CD47, the anti-Sirpα antibody disclosed in the prior art can also bind to Sirpγ and have adverse effects in human, for example inhibiting proliferation of T cells and reducing an immune response. Since testing of existing known antibodies is conducted in a mouse model that does not have the Sirpγ gene, it is impossible to predict whether the existing anti-CD47 antibody or non-selective anti-Sirpα antibody have such side effects. For example, US20140242095A1 discloses an antibody against Sirpα, but it has relatively strong binding to both Sirpβ and Sirpγ, and binds to human T cells. If it is used in the process of developing a clinical drug, there may be side effects caused by off-target effects, bringing about security issues.

Therefore, there is an urgent need in the field for a Sirpα-targeting antibody, which has better effects such as targeting a wider patient population (for example, targeting both a population expressing V1 and/or a population expressing V2), being able to bind to Sirpα while not binding to human Sirpβ and Sirpγ so as to reduce side effects, and being able to bind to primate-derived Sirpα so as to make preclinical research more convenient.

SUMMARY OF THE PRESENT INVENTION

The technical problem to be solved by the present disclosure is to overcome the inability of the antibodies in the prior art of simultaneously binding to two forms of human Sirpα, Sirpα-V1 and Sirpα-V2, so as to target more patient populations, of binding to Sirpα while not binding to human Sirpβ and Sirpγ so as to reduce side effects, and of low expression level after humanization. The present disclosure provides a Sirpα-targeting antibody or an antigen-binding fragment thereof, a bispecific antibody, and a preparation method and use thereof. Compared with the prior art, the antibody or an antigen-binding fragment thereof of the present disclosure has good activity of binding to Sirpα, can block the binding of human Sirpα (including Sirpα-V1 and Sirpα-V2) to human CD47 so that the antibody or an antigen-binding fragment thereof can be developed as a new drug that targets the binding of Sirpα to CD47 to achieve the purpose of treating a tumor, and the antibody or an antigen-binding fragment thereof of the present disclosure can simultaneously binds to the two forms of human Sirpα, Sirpα-V1 and Sirpα-V2 with binding activity significantly higher than that of the prior art. Therefore, the antibody or an antigen-binding fragment thereof of the present disclosure has advantages of many aspects when developed as a drug, and can target more patient populations (a population expressing Sirpα-V1 and/or a population expressing Sirpα-V2). The antibody or an antigen-binding fragment thereof of the present disclosure does not bind to human Sirpβ and Sirpγ; and also does not bind to human T cells, so that the antibody or an antigen-binding fragment thereof of the present disclosure has better selectivity and avoids a side effect caused by off-target effect brought about by binding to T cells in clinical application. The antibody or an antigen-binding fragment thereof of the present disclosure preferably can also bind to *cynomolgus* (cyno) Sirpα (Cyno Sirpα), and especially has strong binding with various pleomorphic Cyno Sirpαs, so that the primate *cynomolgus* (cyno) can be selected for use in preclinical safety evaluation research, which brings great convenience to preclinical pharmacology, toxicology and the like research. The analysis results of potential post-translational modification (PTM) show that the antibody or an antigen-binding fragment thereof of the present disclosure has the characteristics of low immunogenicity and low risk of druggability. The antibody or an antigen-binding fragment thereof of the present disclosure has a higher expression level after humanization, which provides convenience and cost savings for downstream production and processes. In a preferred embodiment of the present disclosure, the expression level of the humanized antibody of the present disclosure is up to 275 mg/L, which is about 4.5 times higher than those of a chimeric antibody and the antibody OSE-172 in the prior art. The bispecific antibody designed and screened out based on the Sirpα antibody sequence of the present disclosure can retain the functional activity of a dual-target antibody, the binding activities of it to the two targets are both close to those of its corresponding monoclonal antibodies, and the activity of blocking the binding of an antigen with a corresponding ligand is also consistent with that of the corresponding monoclonal antibody. The in vivo pharmaceutical effect of the bispecific antibody of the present disclosure in mice is significantly better than that of the monoclonal antibody, and has the advantage of more convenient administration. In a certain formulation recipe screening embodiment, the bispecific antibody of the present disclosure has good stability, with the purity being changed within 3% after treated at 40° C. for 30 days. These bispecific antibodies (called SBodies in the present disclosure), which are similar in structure to conventional IgGs, have the same entire Fc as normal antibodies, so that their purification process can be carried out according to those of normal antibodies, and thus the process is simple and has the advantage of low production cost. In view of the above, the unique properties of the antibody or an antigen-binding fragment thereof of the present disclosure enable the same to be more suitable for the development of a drug for an antibody or an antigen-binding fragment thereof against a human Sirpα target, and as a candidate drug, it can be administered alone or in combination, especially providing a new and even better option for combined immunotherapy of tumors with a PD-1 antibody and the like.

In order to solve the aforementioned technical problems, a first aspect of the present disclosure provides a Sirpα-targeting antibody or an antigen-binding fragment thereof, including a light chain variable region, i.e., VL and/or a heavy chain variable region, i.e., VH. The antibody or the antigen-binding fragment thereof binds to human Sirpα-V1 and human Sirpα-V2, but weakly binds to or does not bind to human Sirpβ and Sirpγ, and does not bind to human T cells, and has the function of blocking the binding of Sirpα to CD47. Therefore, it can be seen that the Sirpα-targeting antibody or the antigen-binding fragment thereof described in the present disclosure recognizes an antigen epitope different from that recognized by the antibody in the prior art, and shows a more excellent technical effect than the prior art.

Preferably, the antibody or the antigen-binding fragment thereof also binds to one or more of Cyno Sirpα L932, L933, L936 and L937, but does not bind to Cyno Sirpα L938 and L939; wherein the amino acid sequence of the L932 has a NCBI reference sequence number of NP_001271679.1, the amino acid sequence of the L933 has a NCBI sequence number of XP_015313155.1, the amino acid sequence of the L936 is as shown in SEQ ID NO: 3, the amino acid sequence of the L937 is as shown in SEQ ID NO: 4, the amino acid sequence of the L938 is as shown in SEQ ID NO: 5, and the amino acid sequence of the L939 is as shown in SEQ ID NO: 6.

In the present disclosure, the "binding" in the context that the antibody or an antigen-binding fragment thereof binds to human Sirpα-V1/human Sirpα-V2 and the antibody or an antigen-binding fragment thereof also binds to Cyno Sirpα is generally "strong binding". The "strong binding" generally means that a $EC_{50}$ in a binding experiment is lower than 0.2 nM (more preferably lower than 0.1 nM), and this definition is mainly conducted based on the experimental results in Tables 5, 13, 6, and 15. Generally, the binding ability of the antibody or an antigen-binding fragment thereof to human Sirpα-V1/human Sirpα-V2 is similar or even better than the binding ability of Ref1 to human Sirpα-V1/human Sirpα-V2.

In the present disclosure, the "binding" means that the $EC_{50}$ in the binding experiment is between 0.2 nM and 2 nM (i.e., 0.2 nM≤$EC_{50}$<2 nM), the "weak binding" means that the $EC_{50}$ in the binding experiment is between 2-10 nM (i.e., 2 nM≤$EC_{50}$<10 nM), and the "faint binding" generally means that the $EC_{50}$ in the binding experiment is higher than 10 nM and lower than 50 nM (i.e., 10 nM$\leq$EC$_{50}$<50 nM), unless otherwise specified. The "no binding" generally refers to EC$_{50}\geq$50 nM in the binding experiment or that the binding signal is undetectable. This definition is mainly conducted based on the experimental results in Table 15. That is, the EC$_{50}$ value of Ref1 binding to Sirp$\beta$ is about 0.126 nM, and the EC$_{50}$ value of Ref2 binding to Sirp$\beta$ is about 0.167 nM, the EC$_{50}$ value of the Ref1 binding to Sirp$\gamma$ is undetectable, and the EC$_{50}$ value of Ref2 binding to Sirp$\gamma$ is approximately 1.46 nM.

The aforementioned EC$_{50}$ values are generally obtained according to conventional experimental methods in the art, such as ELISA, and the aforementioned EC$_{50}$ values are generally obtained according to conventional blocking ELISA experiments in the art.

More preferably, the VL includes the following complementary determining regions (CDRs) (defined by CCG numbering rules): VL CDR1 as shown in the amino acid sequence of SEQ ID NO: 11; VL CDR2 as shown in the amino acid sequence of SEQ ID NO: 12; and/or VL CDR3 as shown in the amino acid sequence of SEQ ID NO: 13; and/or the VH includes the following CDRs: VH CDR1 as shown in the amino acid sequence of SEQ ID NO: 14; VH CDR2 as shown in the amino acid sequence of SEQ ID NO: 15; and/or VH CDR3 as shown in the amino acid sequence of SEQ ID NO: 16; or alternatively, the VL has 3, 2 or 1 amino acid mutations in the amino acid sequences of the VL CDR1, VL CDR2 and VL CDR3, respectively, and/or the VH has 3, 2 or 1 amino acid mutations in the amino acid sequences of the VH CDR1, VH CDR2 and VH CDR3, respectively.

"Amino acid mutation" in a phrase like "having 3, 2 or 1 amino acid mutations" means that there are amino acid mutations in the sequence of the variant compared with the original amino acid sequence, including amino acid insertion, deletion or substitution based on the original amino acid sequence. An exemplary explanation is that the mutation of CDRs can include mutations of 3, 2 or 1 amino acids, and the same or different numbers of amino acid residues can be optionally selected for mutation among these CDRs. For example, mutation of 1 amino acid is conducted on CDR1, and no amino acid mutation is conducted on CDR2 and CDR3.

In the present disclosure, the mutations may include mutations currently well known to those skilled in the art. For example, some mutations that may be made to the antibody during the production or application of the antibody, such as mutations made to possible sites, especially PTM sites of CDR regions, include related mutations such as aggregation of antibodies, mutations at asparagine deamidation sensitive sites (NG, NS or NH, etc.), aspartic acid isomerization (DG, DP) sensitive sites, N-glycosylation (N—{P}S/T) sensitive sites and oxidation sensitive sites.

The CDR amino acid residues in the VL and VH regions of the antibody or an antigen-binding fragment thereof of the present disclosure conform to the known numbering rules of Kabat, Contact, CCG, AbM and Chothia in terms of numbers and positions. In the present disclosure, the amino acid sequences of the CDRs listed above are all shown in accordance with a CCG definition rule (the sequences in the claims of the present disclosure are also shown in accordance with the CCG definition rule). However, it is well known to those of skills in the art that the CDR of the antibody can be defined by various methods, such as a Kabat definition rule based on sequence variability (see Kabat et al., protein sequence in immunology, 5th edition, National Institutes of Health, Bethesda, Maryland (1991)) and a Chothia definition rule based on the position of a structural loop region (see J Mol Biol 273:927-48, 1997). The boundary of a given CDR may vary depending on the scheme used for recognition, the definition rules described in the present disclosure and the CDR sequences defined by the antibody are shown in Tables 7-12. For example, the Kabat scheme is based on structural alignment, while the Chothia scheme is based on structural information. The numbering used in the Kabat and Chothia schemes is based on the most commonly used sequence length of an antibody region, and insertions are adapted by inserting letters (e.g., "30a") and deletions are present in some antibodies. Both the two schemes place certain insertions and deletions ("indels") at different positions to result in differential numberings. The Contact scheme is based on analysis of the crystal structure of a complex and is similar to the Chothia numbering scheme in many aspects. Therefore, the terms "CDR" and "complementarity determining region" of a given antibody or a region thereof (e.g., variable region) and individual CDRs (e.g., "VH CDR1, VH CDR2") of the antibody or a region thereof should be understood to cover complementarity determining regions as defined by any of the aforementioned known schemes described by the present disclosure, unless otherwise specified. Although the scope of protection claimed in the claims of the present disclosure is sequences as shown based on the CCG definition rule, the corresponding amino acid sequences according to other CDR definition rules (e.g., the following corresponding sequences listed according to different CDR numbering rules) also should fall within the protection scope of the present disclosure.

For example, according to the definition of the Kabat numbering rule, the VL includes the following CDRs: VL CDR1 as shown in the amino acid sequence of SEQ ID NO: 11; VL CDR2 as shown in the amino acid sequence of SEQ ID NO: 12; and/or VL CDR3 as shown in the amino acid sequence of SEQ ID NO: 13; and/or the VH includes the following CDRs: VH CDR1 as shown in the amino acid sequence of SEQ ID NO: 17; VH CDR2 as shown in the amino acid sequence of SEQ ID NO: 15; and/or VH CDR3 as shown in the amino acid sequence of SEQ ID NO: 16.

For example, according to the definition of the AbM numbering rule, the VL includes the following CDRs: VL CDR1 as shown in the amino acid sequence of SEQ ID NO: 11; VL CDR2 as shown in the amino acid sequence of SEQ ID NO: 12; and/or VL CDR3 as shown in the amino acid sequence of SEQ ID NO: 13; and/or the VH includes the following CDRs: VH CDR1 as shown in the amino acid sequence of SEQ ID NO: 14; VH CDR2 as shown in the amino acid sequence of SEQ ID NO: 18; and/or VH CDR3 as shown in the amino acid sequence of SEQ ID NO: 16.

For example, according to the definition of the Chothia numbering rule, the VL includes the following CDRs: VL CDR1 as shown in the amino acid sequence of SEQ ID NO: 11; VL CDR2 as shown in the amino acid sequence of SEQ ID NO: 12; and/or VL CDR3 as shown in the amino acid sequence of SEQ ID NO: 13; and/or the VH includes the following CDRs: VH CDR1 as shown in the amino acid sequence of SEQ ID NO: 19; VH CDR2 as shown in the amino acid sequence of SEQ ID NO: 20; and/or VH CDR3 as shown in the amino acid sequence of SEQ ID NO: 16.

For example, according to the definition of the Contact numbering rule, the VL includes the following CDRs: VL CDR1 as shown in the amino acid sequence of SEQ ID NO: 21; VL CDR2 as shown in the amino acid sequence of SEQ ID NO: 22; and/or VL CDR3 as shown in the amino acid sequence of SEQ ID NO: 23; and/or the VH includes the following CDRs: VH CDR1 as shown in the amino acid sequence of SEQ ID NO: 24; VH CDR2 as shown in the amino acid sequence of SEQ ID NO: 25; and/or VH CDR3 as shown in the amino acid sequence of SEQ ID NO: 26.

Preferably, the Sirpα-targeting antibody is a murine antibody.

More preferably, the VL of the murine antibody is the amino acid sequence as shown in SEQ ID NO: 9 or a mutation thereof; and/or, the VH of the murine antibody is the amino acid sequence as shown in SEQ ID NO: 10 or a mutation thereof; more preferably, the VL of the murine antibody is encoded by a nucleotide as shown in SEQ ID NO: 7; and/or, the VH of the murine antibody is encoded by a nucleotide as shown in SEQ ID NO: 8;

The mutation is the deletion, substitution or insertion of one or more amino acid residues on the amino acid sequence of the VL and/or the VH, and the mutated amino acid sequence has at least 85% sequence identity with the amino acid sequence of the VL and/or the VH, and maintains or improves the binding of the antibody to Sirpα; the at least 85% sequence identity is preferably at least 90% sequence identity; more preferably at least 95% sequence identity; and most preferably at least 99% sequence identity.

Preferably, the Sirpα-targeting antibody or the antigen-binding fragment thereof further includes a constant region of the murine antibody or a constant region of a human antibody; the constant region of the murine antibody includes the heavy chain constant region of murine IgG1, IgG2a, IgG2b or IgG3 and κ or λ type light chain constant region, and the constant region of the human antibody includes the heavy chain constant region of human IgG1, IgG2, IgG3 or IgG4 and κ or λ type light chain constant region.

More preferably, when the Sirpα-targeting antibody or the antigen-binding fragment thereof includes the variable region of the murine antibody and the constant region of the human antibody, the constant region of the human antibody includes the heavy chain constant region of human IgG4 and κ type light chain constant region of amino acid sequences as shown in SEQ ID NO: 28 and SEQ ID NO: 27 respectively.

Preferably, the Sirpα-targeting antibody is a humanized antibody.

More preferably, the framework region of the humanized antibody includes a heavy chain framework region of a human antibody and a light chain framework region of a human antibody;

further more preferably, the light chain framework region of the human antibody is selected from 1) one or more of IGKV1-27*01, IGKV1-33*01, IGKV1-39*01, IGKV1-NL1*01, IGKV1/OR10-1*01, IGKV1D-33*01, IGKV1D-39*01, IGKV1-12*01, IGKV1-12*02 and IGKV1-17*02, and a J gene is selected from 2) one or more of hJk1, hJk2.1, hJk2.2, hJk2.3, hJk2.4, hJk3, hJk4.1, hJk4.2 or hJk5, or backmutation thereof; and/or, the heavy chain framework region of the human antibody is selected from 1) one or more of IGHV1-46*01, IGHV1-46*02, IGHV1-46*03, IGHV1-69*02, IGHV1-69*04, IGHV1-69*06, IGHV1-69*08, IGHV1-69*09, IGHV1-69*10 or IGHV1-69*14, and the J gene is selected from 2) one or more of hJh1, hJh2, hJh3.1, hJh3.2, hJh4.1, hJh4.2, hJh4.3, hJh5.1, hJh5.2, hJh6.1, hJh6.2 or hJh6.3, or back-mutation thereof; and the number of amino acid sites subjected to the back-mutation is preferably 0-10.

Most preferably, the VL of the humanized antibody includes the amino acid sequence as shown in any one of SEQ ID NOs: 29-34, or a mutation thereof; and/or, the VH sequence of the humanized antibody includes the amino acid sequence as shown in any one of SEQ ID NOs: 35-41, or a mutation thereof; the mutation is the deletion, substitution or addition of one or more amino acid residues on the amino acid sequence of the VL and/or the VH, and the mutated amino acid sequence has at least 85% sequence identity with the amino acid sequence of the VL and/or the VH, and maintains or improves the binding of the antibody or the antigen-binding fragment thereof to Sirpα; the at least 85% sequence identity is preferably at least 90% sequence identity; more preferably at least 95% sequence identity; and most preferably at least 99% sequence identity.

In a certain preferred embodiment of the present disclosure, the VL includes the amino acid sequence as shown in SEQ ID NO: 29; and the VH includes the amino acid sequence as shown in SEQ ID NO: 35. In a certain preferred embodiment of the present disclosure, the light chain variable region VL includes the amino acid sequence as shown in SEQ ID NO: 30; and the VH includes the amino acid sequence as shown in SEQ ID NO: 36. In a certain preferred embodiment of the present disclosure, the light chain variable region VL includes the amino acid sequence as shown in SEQ ID NO: 30; and the heavy chain variable region VH includes the amino acid sequence as shown in SEQ ID NO: 37. In a certain preferred embodiment of the present disclosure, the light chain variable region VL includes the amino acid sequence as shown in SEQ ID NO: 30; and the heavy chain variable region VH includes the amino acid sequence as shown in SEQ ID NO: 38. In a certain preferred embodiment of the present disclosure, the light chain variable region VL includes the amino acid sequence as shown in SEQ ID NO: 30; and the heavy chain variable region VH includes the amino acid sequence as shown in SEQ ID NO: 39. In a certain preferred embodiment of the present disclosure, the light chain variable region VL includes the amino acid sequence as shown in SEQ ID NO: 30; and the heavy chain variable region VH includes the amino acid sequence as shown in SEQ ID NO: 40. In a certain preferred embodiment of the present disclosure, the light chain variable region VL includes the amino acid sequence as shown in SEQ ID NO: 30; and the heavy chain variable region VH includes the amino acid sequence as shown in SEQ ID NO: 41. In a certain preferred embodiment of the present disclosure, the light chain variable region VL includes the amino acid sequence as shown in SEQ ID NO: 31; and the heavy chain variable region VH includes the amino acid sequence as shown in SEQ ID NO: 36. In a certain preferred embodiment of the present disclosure, the light chain variable region VL includes the amino acid sequence as shown in SEQ ID NO: 32; and the heavy chain variable region VH includes the amino acid sequence as shown in SEQ ID NO: 36. In a certain preferred embodiment of the present disclosure, the light chain variable region VL includes the amino acid sequence as shown in SEQ ID NO: 33; and the heavy chain variable region VH includes the amino acid sequence as shown in SEQ ID NO: 36. In a certain preferred embodiment of the present disclosure, the light chain variable region VL includes the amino acid sequence as shown in SEQ ID NO: 34; and the heavy chain variable region VH includes the amino acid sequence as shown in SEQ ID NO: 36. In a certain preferred embodiment of the present disclosure, the light chain variable region VL includes the amino acid sequence as shown in SEQ ID NO: 31; and the heavy chain variable region VH includes the amino acid sequence as shown in SEQ ID NO: 39. In a certain preferred embodiment of the present disclosure, the light chain variable region VL includes the amino acid sequence as shown in SEQ ID NO: 32; and the heavy chain variable region VH includes the amino acid sequence as shown in SEQ ID NO: 39. In a certain preferred embodiment of the present disclosure, the light chain variable region VL includes the amino acid sequence as shown in SEQ ID NO: 33; and the heavy chain variable region VH includes the amino acid sequence as shown in SEQ ID NO: 39. In a certain preferred embodiment of the present disclosure, the light chain variable region VL includes the amino acid sequence as shown in SEQ ID NO: 34; and the heavy chain variable region VH includes the amino acid sequence as shown in SEQ ID NO: 39. In a certain preferred embodiment of the present disclosure, the light chain variable region VL includes the amino acid sequence as shown in SEQ ID NO: 29; and the heavy chain variable region VH includes the amino acid sequence as shown in SEQ ID NO: 39.

Preferably, the light chain of the antibody or the antigen-binding fragment thereof includes the κ or λ type light chain constant region of a human antibody, or a mutation thereof; and/or, the heavy chain of the antibody or the antigen-binding fragment thereof includes the heavy chain constant region of human IgG1, IgG2, IgG3 and IgG4, or a mutation thereof.

More preferably, the light chain of the antibody or the antigen-binding fragment thereof includes the κ type light chain constant region of the human antibody.

More preferably, the heavy chain of the antibody or the antigen-binding fragment thereof includes the heavy chain constant region of human IgG4.

Further more preferably, the light chain of the antibody or the antigen-binding fragment thereof includes the amino acid sequence as shown in SEQ ID NO: 42, SEQ ID NO: 44, SEQ ID NO: 45, SEQ ID NO: 46, SEQ ID NO: 47 or SEQ ID NO: 48 or a mutation thereof; and/or the heavy chain of the antibody or the antigen-binding fragment thereof includes the amino acid sequence as shown in SEQ ID NO: 43 or a mutation thereof.

In a preferred embodiment of the present disclosure, the Sirpα-targeting antibody or the antigen-binding fragment thereof includes the following light and heavy chains: the light chain as shown in the amino acid sequence of SEQ ID NO: 42, and the heavy chain as shown in the amino acid sequence of SEQ ID NO: 43.

In a preferred embodiment of the present disclosure, the Sirpα-targeting antibody or the antigen-binding fragment thereof includes the following light and heavy chains: the light chain as shown in the amino acid sequence of SEQ ID NO: 44, and the heavy chain as shown in the amino acid sequence of SEQ ID NO: 43.

In a preferred embodiment of the present disclosure, the Sirpα-targeting antibody or the antigen-binding fragment thereof includes the following light and heavy chains: the light chain as shown in the amino acid sequence of SEQ ID NO: 45, and the heavy chain as shown in the amino acid sequence of SEQ ID NO: 43.

In a preferred embodiment of the present disclosure, the Sirpα-targeting antibody or the antigen-binding fragment thereof includes the following light and heavy chains: the light chain as shown in the amino acid sequence of SEQ ID NO: 46, and the heavy chain as shown in the amino acid sequence of SEQ ID NO: 43.

In a preferred embodiment of the present disclosure, the Sirpα-targeting antibody or the antigen-binding fragment thereof includes the following light and heavy chains: the light chain as shown in the amino acid sequence of SEQ ID NO: 47, and the heavy chain as shown in the amino acid sequence of SEQ ID NO: 43.

In a preferred embodiment of the present disclosure, the Sirpα-targeting antibody or the antigen-binding fragment thereof includes the following light and heavy chains: the light chain as shown in the amino acid sequence of SEQ ID NO: 48, and the heavy chain as shown in the amino acid sequence of SEQ ID NO: 43.

Preferably, the Sirpα-targeting antibody or the antigen-binding fragment thereof includes immunoglobulin, Fab, Fab', F(ab')₂, Fv or a single chain Fv fragment (scFv), a bispecific antibody, a multispecific antibody, a single domain antibody, a single-domain antibody, or any other antibody that retains the partial ability of the antibody of specifically binding to an antigen, or a monoclonal or polyclonal antibody prepared from the aforementioned antibodies. The monoclonal antibody can be developed by various ways and technologies, including hybridoma technology, phage display technology, single lymphocyte gene cloning technology, etc. The mainstream is to prepare a monoclonal antibody from wild-type or transgenic mice by hybridoma technology.

In order to solve the aforementioned technical problems, a second aspect of the present disclosure provides a bispecific antibody including a first protein functional region and a second protein functional region, wherein the first protein functional region is the Sirpα-targeting antibody or the antigen-binding fragment thereof in the first aspect of the present disclosure, and the second protein functional region is an antibody targeting a non-Sirpα antigen, or an antigen-binding fragment thereof. The bispecific antibody can not only retain the binding activity and functional activity of a single Sirpα antibody, but also can maintain the binding and functional activities of another protein functional region. Moreover, the bispecific antibody is structurally similar to a normal IgG antibody, can be expressed and purified according to expression and purification methods of a conventional antibody, and is stable.

The bispecific antibody of the present disclosure can be a sequence-based IgG like bispecific antibody (SBody). These bispecific antibody molecules have the same entire Fc as normal antibodies, so that their purification process can be carried out according to those of normal antibodies, and thus the process is simple and has the advantage of low production cost.

In a specific embodiment of the present disclosure, in the bispecific antibody as described above, the non-Sirpα antigen is an immune checkpoint antigen or a tumor therapy target, and the immune checkpoint antigen preferably includes PD-1, PD-L1, Tim3, or LAG3, and the tumor therapy target preferably includes CLDN18.2 (claudin 18.2); more preferably, the second protein functional region is an anti-PD-1 antibody, anti-PD-L1 antibody, anti-Tim3 antibody, anti-LAG3 antibody or anti-CLDN18.2 antibody or an antigen-binding fragment thereof; most preferably, the anti-PD-1 antibody is Nivolumab (referred to as Nivo for short) or Pembrolizumab (referred to as Pem for short), and the anti-PD-L1 antibody is Atezolumab, Avelumab, or Durvalumab.

In order to design a bispecific antibody that has a simple production process and retains effective activity, the bispecific antibody of the present disclosure is in the form of a structure similar to normal IgG, and specifically, protein functional regions which can target the light chain and/or heavy chain variable regions of two targets are designed on its structure, and the two protein functional regions share the same heavy chain Fc region. Preferably, an antibody molecule of one target is linked to one end of the light or heavy chain of an intact antibody of the other target in the form of one or more scFvs. In this way, the non-uniformity of expression products caused by the expression of different heavy chain Fcs and/or different light chains can be avoided, for example in the co-expression of a Knob-type Fc and a Hole-type Fc, there will be a inhomogeneous Fc-Fc pairing form in the expression process, which will bring a lot of inconvenience to the purification process; and it can also avoid the possible influence of cross design of partial regions of the light and heavy chains on structural activity and the Fc mismatch phenomenon in the course of the process. Through the design of one or more scFvs, the activity against a specific target can further be modulated. By screening different designs, the SBody with the optimal activity can be obtained. Due to differences in sequence and design, the obtained preferred SBody retains dual-target activity, and has advantages in druggability and the like aspects, so that it can be used as a normal antibody for drug development.

In some specific embodiments, in the bispecific antibody as described above, the first protein functional region is immunoglobulin, and the second protein functional region is one or more, preferably two scFvs; or alternatively, the second protein functional region is immunoglobulin, and the first protein functional region is one or more, preferably two scFvs; wherein, the scFv includes a heavy chain variable region and a light chain variable region that are linked by a linker which is preferably $(Gly-Gly-Gly-Gly-Ser)_w$ [hereinafter referred to as $(G_4S)_w$ for short]; the scFv is linked to the immunoglobulin through a linker which is selected from a common peptide fragment in the art or $(G4S)_w$; wherein the w is preferably an integer between 0-10 (SEQ ID NOs: 58-61 and 64-70), and more preferably 1, 2, 3 or 4 (SEQ ID NOs: 58-61).

The summary of the bispecific design (general formula 1) is shown in Table 17 of the present disclosure. In Table 17, a light chain-containing sequence means that the sequence may include, in addition to the light chain sequence, a scFv linked to the light chain sequence; and a heavy chain-containing sequence means that the sequence may include, in addition to the heavy chain sequence, a scFv linked to the heavy chain sequence. T1 represents the first protein functional region against the target 1 (e.g., Sirpα), and T2 represents the second protein functional region against the target 2 (not Sirpα). T1 (scFv) represents the scFv sequence of the antibody against target 1; and T2 (scFv) represents the scFv sequence against target 2.

n1, n2, n3 and n4 in $(scFv)_{n1}$, $(scFv)_{n2}$, $(scFv)_{n3}$ and $(scFv)_{n4}$ are respectively natural numbers, which can be 0, 1, 2, 3, etc. In a specific embodiment of the present disclosure, the value of at least one of the n1, n2, n3 and n4 is 1, and the rest are 0. VL represents the light chain variable region sequence of the antibody against the target 1 or 2; and VH represents the heavy chain variable region sequence of the antibody against the target 1 or 2. LC represents the constant region sequence of the light chain (κ or λ), preferably the human light chain constant region sequence; and HC represents the constant region sequence of the heavy chain including IgG1, IgG2, IgG3, IgG4, etc. (abbreviated as HC-IgG1, HC-IgG2, HC-IgG3, and HC-IgG4), preferably human heavy chain constant region sequence (HC-hIgG). When scFv or other protein sequences are linked to the C-terminus of the heavy chain constant region, the last amino acid K at the C-terminus of the heavy chain constant region can be mutated, preferably mutated to A. Therefore, in scheme 1, T1 is immunoglobulin, and T2 is scFv; in scheme 2, T2 is immunoglobulin, and T1 is scFv; the targets of the scFvs are the same; and in schemes 3 and 4, the scFvs at two ends target two different targets.

In Table 17, the scFv is a light chain variable region-linker-heavy chain variable region, and the N-terminus of the light chain variable region or the C-terminus of the heavy chain variable region is accordingly linked to the C-terminus or N-terminus of the light and/or heavy chain of the immunoglobulin through the linker; or the scFv is heavy chain variable region-linker-light chain variable region, and the N-terminus of the heavy chain variable region or the C-terminus of the light chain variable region is accordingly linked to the C-terminus or N-terminus of the light and/or heavy chain of the immunoglobulin through the linker.

It should be noted that when the aforementioned scFv is light chain variable region-linker-heavy chain variable region, the linking mode of it is that the C-terminus of the light chain variable region is linked with the linker, and the linker is then linked with the N-terminus of the heavy chain variable region, thereby exposing the N-terminus of the light chain variable region and the C-terminus of the heavy chain variable region in the scFv, so that it can be linked to the light and/or heavy chain of the immunoglobulin through a linker. In the present disclosure, when it is linked to the light chain of the immunoglobulin, in some specific embodiments, preferably the C-terminus of the heavy chain variable region of the scFv is linked to the N-terminus of the heavy chain of the immunoglobulin through a linker; and when it is linked to the heavy chain of the immunoglobulin, in some specific embodiments, preferably the N-terminus of the light chain variable region of the scFv is linked to the C-terminus of the heavy chain of the immunoglobulin.

When the scFv is heavy chain variable region-linker-light chain variable region, the linking mode of it is that the N-terminus of the light chain variable region is linked with the linker, and the linker is then linked with the C-terminus of the heavy chain variable region, thereby exposing the C-terminus of the light chain variable region and the N-terminus of the heavy chain variable region in the scFv, so that it can be linked to the light and/or heavy chain of the immunoglobulin through a linker. In this case, when it is linked to the light chain of the immunoglobulin, in some specific embodiments, preferably the C-terminus of the light chain variable region of the scFv is linked to the N-terminus of the heavy chain of the immunoglobulin; and when it is linked to the heavy chain of the immunoglobulin, in some specific embodiments, preferably the N-terminus of the heavy chain variable region of the scFv is linked to the C-terminus of the heavy chain of the immunoglobulin. Preferably, the two scFvs are symmetrically linked to the C-terminus and/or N-terminus of the light and/or heavy chain of the immunoglobulin.

In the present disclosure, for the antibody sequences against various targets involved in the bispecific design, in addition to the anti-Sirpα antibody sequence or an antigen-binding fragment thereof of the present disclosure, other antibody sequences against the targets are derived from published antibody sequences. It includes anti-PD-1 antibodies Nivolumab/Opidivo® (referred to as Nivo for short) and Pembrolizumab/Keytruda® (referred to as Pem for short).

More preferably, the bispecific antibody can be that: the first protein functional region is scFv, and the second protein functional region is immunoglobulin; wherein the scFv of the first protein functional region includes the VL and VH as described in the first aspect of the present disclosure.

In a preferred embodiment of the present disclosure, in the scFv of the first protein functional region, the included VL includes the amino acid sequence as shown in SEQ ID NO: 29; and the included VH includes the amino acid sequence as shown in SEQ ID NO: 35. In a preferred embodiment of the present disclosure, in the scFv of the first protein functional region, the included VL includes the amino acid sequence as shown in SEQ ID NO: 30; and the included VH includes the amino acid sequence as shown in any one of SEQ ID NOs: 36-41. In a preferred embodiment of the present disclosure, in the scFv of the first protein functional region, the included VL includes the amino acid sequence as shown in any one of SEQ ID NOs: 31-34; and the included VH includes the amino acid sequence as shown in SEQ ID NO: 36. In a preferred embodiment of the present disclosure, in the scFv of the first protein functional region, the included VL includes the amino acid sequence as shown in any one of SEQ ID NO: 29 or 31-34; and the included VH includes the amino acid sequence as shown in SEQ ID NO: 39.

Preferably, the immunoglobulin includes the light chain variable region of Pem, the κ type chain as the light chain constant region, the heavy chain variable region of Pem, and the amino acid sequence of hIgG4 as the heavy chain constant region; or alternatively, the immunoglobulin includes the light chain variable region of Nivo, the κ type chain as the light chain constant region, the heavy chain variable region of Nivo, and the amino acid sequence of hIgG4 as the heavy chain constant region;

the C-terminuses of the heavy chain variable regions of the two scFvs are symmetrically linked to the N-terminuses of the two heavy chains of the immunoglobulin through a linker; and the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39; or alternatively, the C-terminuses of the heavy chain variable regions of the two scFvs are symmetrically linked to the N-terminuses of the two light chain variable regions of the immunoglobulin through a linker; and the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39; or alternatively, the N-terminuses of the heavy chain variable regions of the two scFvs are symmetrically linked to the C-terminuses of the two heavy chains of the immunoglobulin through a linker; and the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39; or alternatively, the N-terminuses of the heavy chain variable regions of the two scFvs are symmetrically linked to the C-terminuses of the two light chains of the immunoglobulin through a linker; and the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39.

Moreover, the bispecific antibody can further include the following structure: the first protein functional region is immunoglobulin, and the immunoglobulin includes a light chain of the amino acid sequence as shown in SEQ ID NO: 48 and a heavy chain of the amino acid sequence as shown in SEQ ID NO: 43; and the second protein functional region is scFv:

The sequence of the light chain variable region of the scFv is the light chain variable region of Pem, and the heavy chain variable region of the scFv is the heavy chain variable region of Pem.

More preferably, the bispecific antibody includes the following light chain amino acid sequence and heavy chain amino acid sequence: the light chain amino acid sequence as shown in SEQ ID NO: 50, and the heavy chain amino acid sequence as shown in SEQ ID NO: 51; or alternatively, the light chain amino acid sequence as shown in SEQ ID NO: 52, and the heavy chain amino acid sequence as shown in SEQ ID NO: 53; or alternatively, the light chain amino acid sequence as shown in SEQ ID NO: 54, and the heavy chain amino acid sequence as shown in SEQ ID NO: 51; or alternatively, the light chain amino acid sequence as shown in SEQ ID NO: 52, and the heavy chain amino acid sequence as shown in SEQ ID NO: 55; or alternatively, the light chain amino acid sequence as shown in SEQ ID NO: 56, and the heavy chain amino acid sequence as shown in SEQ ID NO: 57.

In order to solve the aforementioned technical problems, a third aspect of the present disclosure provides an isolated nucleic acid, which encodes the Sirpα-targeting antibody or the antigen-binding fragment thereof of the first aspect of the present disclosure or the bispecific antibody of the second aspect of the present disclosure.

The method for preparing the nucleic acid is a conventional preparation method in the art, and preferably includes the following steps: obtaining the nucleic acid molecule encoding the aforementioned antibody or an antigen-binding fragment thereof by gene cloning technology, or obtaining the nucleic acid molecule encoding the aforementioned antibody or an antigen-binding fragment thereof by a method of artificial full sequence synthesis.

Those skilled in the art know that, substitution, deletion, alteration, insertion or addition can be appropriately introduced into the base sequence encoding the amino acid sequence of the antibody or an antigen-binding fragment thereof, so as to provide a polynucleotide homologue. The polynucleotide homologue of the present disclosure can be prepared by making substitution, deletion or addition of one or more bases in the sequence gene encoding the antibody or an antigen-binding fragment thereof within a range that maintains the activity of the antibody.

In order to solve the aforementioned technical problems, a fourth aspect of the present disclosure provides a recombinant expression vector, which includes the isolated nucleic acid of the third aspect of the present disclosure.

The recombinant expression vector can be obtained by a conventional method in the art, namely: it is constructed by linking the nucleic acid molecule of the present disclosure onto various expression vectors. The expression vectors are various conventional vectors in the art, as long as they can accommodate the aforementioned nucleic acid molecule.

Preferably, the expression vector includes a eukaryotic expression vector and/or a prokaryotic expression vector.

In order to solve the aforementioned technical problems, a fifth aspect of the present disclosure provides a transformant including the recombinant expression vector of the fourth aspect of the present disclosure in a host cell.

The method for preparing the transformant can be a conventional preparation method in the art, for example:

preparing by transforming the aforementioned recombinant expression vector into host cells. The host cells are various conventional host cells in the art, as long as the aforementioned recombinant expression vector can replicate by itself stably, and the nucleic acid carried by it can be expressed effectively. Preferably, the host cell includes an eukaryotic and/or prokaryotic cell, the prokaryotic cell is preferably *E. coli* cell such as TG1 or BL21 (expressing a single chain antibody or a Fab antibody), and the eukaryotic cell is preferably HEK293 or CHO cell (expressing a full-length IgG antibody). The preferred recombinant expression transformant of the present disclosure can be obtained by transforming the aforementioned recombinant expression plasmid into a host cell. The transformation method is a conventional transformation method in the art, and preferably a chemical transformation method, a thermal shock method or an electrotransformation method.

In order to solve the aforementioned technical problems, a sixth aspect of the present disclosure provides a method for preparing a Sirpα-targeting antibody or the antigen-binding fragment thereof, including culturing the transformant of the fifth aspect of the present disclosure, and obtaining the Sirpα-targeting antibody or an antigen-binding fragment thereof from the culture.

In order to solve the aforementioned technical problems, a seventh aspect of the present disclosure provides a pharmaceutical composition including the Sirpα-targeting antibody or the antigen-binding fragment thereof of the first aspect of the present disclosure and/or the bispecific antibody of the second aspect of the present disclosure, and a pharmaceutically acceptable carrier.

Preferably, the pharmaceutical composition further includes other anti-tumor antibodies as active ingredients.

The pharmaceutically acceptable carrier can be a conventional carrier in the art, and the carrier can be any suitable physiologically or pharmaceutically acceptable pharmaceutical accessory. The pharmaceutical accessory is a conventional pharmaceutical accessory in the art, and preferably includes a pharmaceutically acceptable excipient (e.g., a conventional excipient in the art, such as glycine and/or trehalose, etc.), a filler, a diluent, a pH adjusting agent (e.g. a buffer, preferably one or more selected from citric acid-sodium citrate, acetic acid-sodium acetate, a phosphate buffer and His-HCl) and/or a surfactant (e.g. Tween 80) etc. More preferably, the pharmaceutical composition includes 0.01-99.99% of the aforementioned antibody or an antigen-binding fragment thereof and/or bispecific antibody, and 0.01-99.99% of the pharmaceutical carrier, with the percentages being the mass percentages of the pharmaceutical composition.

In a preferred embodiment, the pharmaceutical composition consists of the Sirpα-targeting antibody or an antigen-binding fragment thereof of the second aspect of the present disclosure and/or the bispecific antibody, and a buffer, glycine, trehalose and Tween 80.

Furthermore, in the pharmaceutical composition: the concentration of the Sirpα-targeting antibody or an antigen-binding fragment thereof and/or the bispecific antibody may preferably be 5 mg/mL-100 mg/mL, and preferably 5 mg/mL; and/or, the concentration of the buffer may preferably be 5 mM-50 mM, and preferably 20 mM; and/or, the concentration of the glycine may preferably be 0 mM-200 mM, and preferably 125 mM; and/or, the concentration of the trehalose may preferably be 0 mM-300 mM, and preferably 125 mM; and/or, the volume ratio of the Tween 80 to the pharmaceutical composition may preferably be 0.01-1%, and preferably 0.02%; and/or, the pH of the pharmaceutical composition may preferably be 5.0-7.0, e.g., 5.5, 6 or 6.5; and/or, in the bispecific antibody, the amino acid sequence of the light chain may preferably be as shown in SEQ ID NO: 52, and the amino acid sequence of the heavy chain may preferably be as shown in SEQ ID NO: 55.

In the present disclosure, the pharmaceutical composition may exist in the form of, for example, a formulation. The method for preparing the formulation can be a conventional method in the art, and for example, the antibody drug is replaced into the formulation recipe by a method of ultra-filtration.

In a certain preferred embodiment, the pharmaceutical composition of the present disclosure consists of 5±0.2 mg/mL of a bispecific antibody (in the bispecific antibody, the amino acid sequence of the light chain is as shown in SEQ ID NO: 52, and the amino acid sequence of the heavy chain is as SEQ ID NO: 55, and hereinafter it is referred to as LB504 bispecific antibody for short), 20 mM citric acid-sodium citrate, 125 mM glycine, 125 mM trehalose and 0.02% Tween 80, and its pH is 5.0.

In a certain preferred embodiment, the pharmaceutical composition of the present disclosure consists of 5±0.2 mg/mL of the LB504 bispecific antibody, 20 mM acetic acid-sodium acetate, 125 mM glycine, 125 mM trehalose, and 0.02% Tween 80, and its pH is 5.0.

In a certain preferred embodiment, the pharmaceutical composition of the present disclosure consists of 5±0.2 mg/mL of the LB504 bispecific antibody, 20 mM His-HCl, 125 mM glycine, 125 mM trehalose and 0.02% ps80, and its pH is 5.5.

In a certain preferred embodiment, the pharmaceutical composition of the present disclosure consists of 5±0.2 mg/mL of the LB504 bispecific antibody, 20 mM citric acid-sodium citrate, 125 mM glycine, 125 mM trehalose and 0.02% ps80, and its pH is 5.5.

In a certain preferred embodiment, the pharmaceutical composition of the present disclosure consists of 5±0.2 mg/mL of the LB504 bispecific antibody, 20 mM His-HCl, 125 mM glycine, 125 mM trehalose and 0.02% ps80, and its pH is 6.0.

In a certain preferred embodiment, the pharmaceutical composition of the present disclosure consists of 5±0.2 mg/mL of the LB504 bispecific antibody, 20 mM citric acid-sodium citrate, 125 mM glycine, 125 mM trehalose and 0.02% ps80, and its pH is 6.0.

In a certain preferred embodiment, the pharmaceutical composition of the present disclosure consists of 5±0.2 mg/mL of the LB504 bispecific antibody, 20 mM His-HCl, 125 mM glycine, 125 mM trehalose and 0.02% ps80, and its pH is 6.5.

In a certain preferred embodiment, the pharmaceutical composition of the present disclosure consists of 5±0.2 mg/mL of the LB504 bispecific antibody, 20 mM PB, 125 mM glycine, 125 mM trehalose and 0.02% ps80, and its pH is 7.0.

Preferably, the pharmaceutical composition is an anti-tumor drug. For example, it is a drug for treating blood tumors and solid tumors such as breast cancer, colorectal cancer, lung cancer, pancreatic cancer, oesophageal cancer, endometrial cancer, ovarian cancer, stomach cancer, prostate cancer, kidney cancer, cervical cancer, myeloma, lymphoma, leukemia, thyroid cancer, uterine cancer, bladder cancer, neuroendocrine cancer, head and neck cancer, liver cancer, nasopharyngeal cancer, testicular cancer, small cell lung cancer, non-small cell lung cancer, melanoma, basal cell skin cancer, squamous cell skin cancer, dermatofibrosarcoma protuberans, Meckel cell carcinoma, glioblastoma, glioma, sarcoma, mesothelioma or myelodysplastic syndrome.

The route of administration of the pharmaceutical composition of the present disclosure is preferably administration by injection. The administration by injection preferably includes intravenous injection, intramuscular injection, intraperitoneal injection, intradermal injection or subcutaneous injection. The pharmaceutical composition is of various conventional dosage forms in the art, preferably in the form of solid, semi-solid or liquid. That is, it can be an aqueous solution, a non-aqueous solution or a suspension, and more preferably a tablet, capsule, granule, injection or infusion, and the like. More preferably it is administrated intravascularly, subcutaneously, intraperitoneally or intramuscularly. Preferably, the pharmaceutical composition can also be administered as an aerosol or coarse spray, i.e. nasally; or alternatively, intrathecally, intramedullary or intraventricularly. More preferably, the pharmaceutical composition can also be administered transdermally, percutaneously, topically, enterally, intravaginally, sublingually or rectally.

The administrated dosage level of the pharmaceutical composition of the present disclosure can be adjusted according to the amount of the composition for achieving a desired diagnostic or therapeutic result. The administration regimen may also be a single injection or multiple injections, or adjusted. The selected dosage level and regimen are reasonably adjusted depending on various factors including the activity and stability (i.e., half-life) of the pharmaceutical composition, formulation, route of administration, combination with other drugs or therapies, the disease or condition to be detected and/or treated, as well as the health status and previous medical history of the subject to be treated.

For the combination therapy, the aforementioned Sirpα-targeting antibody or an antigen-binding fragment thereof, the aforementioned bispecific antibody and/or a further therapeutic or diagnostic agent can each be used as a single agent in any time range suitable for performing the expected treatment or diagnosis. Therefore, these single agents can be administered substantially simultaneously (i.e., as a single agent or within minutes or hours) or administered sequentially and continuously. For example, these single agents can be administered within one year, or within 10, 8, 6, 4, or 2 months, or within 4, 3, 2, or 1 weeks, or within 5, 4, 3, 2, or 1 days.

See The Merck Manual of Medical Information (Berkow et al., 2000) and Merck&Co. Inc., Whitehouse Station, New Jersey; Ebadi (1998) CRC Desk Reference of Clinical Pharmacology and the like works, for additional instructions on formulation, dosage, administration regimen and measurable treatment outcomes.

In order to solve the aforementioned technical problems, an eighth aspect of the present disclosure provides a use of the Sirpα-targeting antibody or the antigen-binding fragment thereof of the first aspect of the present disclosure, or the bispecific antibody of the second aspect of the present disclosure, or the pharmaceutical composition of the seventh aspect of the present disclosure in preparation of a drug for diagnosing, preventing and/or treating a tumor. Preferably, the tumor is as described in the aforementioned seventh aspect.

In order to solve the aforementioned technical problems, the present disclosure further provides use of the Sirpα-targeting antibody or the antigen-binding fragment thereof of the first aspect of the present disclosure, or the bispecific antibody of the second aspect of the present disclosure, or the pharmaceutical composition of the seventh aspect of the present disclosure in diagnosing, preventing and/or treating a tumor. Preferably, the tumor is as described in the seventh aspect of the present disclosure.

In order to solve the aforementioned technical problems, the present disclosure further provides a kit of parts including a part A and a part B, wherein the part A is the Sirpα-targeting antibody or the antigen-binding fragment thereof of the first aspect of the present disclosure, or the bispecific antibody of the second aspect of the present disclosure, or the pharmaceutical composition of the seventh aspect of the present disclosure, and the part B is other anti-tumor antibodies or contains a pharmaceutical composition of other anti-tumor antibodies. The part A and the part B can be used simultaneously, or the part A can be used first and then the part B is used, or alternatively the part B can be used first and then the part A is used, which can be determined according to the actual needs of the specific application.

In the present disclosure, scientific and technical terms used herein have the meanings commonly understood by those skilled in the art, unless otherwise specified. Furthermore, the cell culture, molecular genetics, nucleic acid chemistry, and immunology laboratory operation steps used herein are all routine steps widely used in the corresponding fields. Meanwhile, for a better understanding of the present disclosure, definitions and explanations of related terms are provided hereafter.

In the present disclosure, the term "variable" generally refers to the fact that some parts of the sequence of the variable domain of an antibody change strongly, which forms the binding and specificity of various specific antibodies to their specific antigens. However, variability is not uniformly distributed in the whole variable region of the antibody. It concentrates on three segments in the variable regions of the light and heavy chains, which are called complementarity determining regions (CDRs) or hypervariable regions (HVRs). The more highly conserved portion of the variable domain is called a framework region (FR). The variable domains of natural heavy and light chains each contain four FRs, most of which adopt a β-folded configuration, and connected by three CDRs to form a loop connection, and in some cases form a part of a β-folded structure. CDRs in each chain are tightly close together by FRs, and form the antigen-binding sites of the antibodies together with the CDRs from the other chain, and the constant regions are not directly involved in the binding of the antibody to the antigen, but they exhibit different effector functions, for example, they are involved in antibody-dependent cytotoxicity of antibodies.

The three-letter and single-letter codes of amino acid used in the present disclosure are well known to those skilled in the art, or as described in J. Biol. Chem, 243, p 3558 (1968).

As used herein, the terms "comprising" or "including" are intended to represent that the composition and method include the stated elements but do not exclude other elements, but according to the understanding of the context, it also includes the case of "consisting of . . . ."

The term "epitope" refers to the portion of an antigen (e.g. Sirpα) that specifically interacts with an antibody molecule. The term "compete" in the present disclosure refers to the ability of an antibody molecule to interfere with the binding of an anti-Sirpα antibody molecule to a target antigen (e.g. Sirpα). The interference with the binding can be direct or indirect (e.g. by binding to the same antigen binding site as that of the antibody molecule or allosteric modulation of the target antigen). A competitive binding assay (e.g. FACS, ELISA or BIACORE assay) can be used for determining whether an antibody molecule can interfere with the extent of binding of another antibody molecule to its target.

The term "antibody" in the present disclosure includes immunoglobulin (Ig), which is a tetrapeptide chain structure formed by connecting two identical heavy chains and two identical light chains by inter-chain disulfide bonds. The amino acid composition and arrangement order of the heavy chain constant region of the immunoglobulin is different, and thus its antigenicity is also different. Accordingly, the immunoglobulin can be divided into five classes, or referred to as isotypes of immunoglobulin, i.e., IgM, IgD, IgG, IgA and IgE, and their corresponding heavy chains are a $\mu$ chain, a $\delta$ chain, a $\gamma$ chain, an $\alpha$ chain and a $\varepsilon$ chain, respectively. The Igs of the same class can be divided into different subclasses according to the difference of amino acid composition in the hinge region of the Ig and the number and positions of disulfide bonds in the heavy chain. For example, IgG can be divided into IgG1, IgG2, IgG3 and IgG4. The light chain is divided into a $\kappa$ chain or a $\lambda$ chain by the difference of the constant region. The Igs in each class of the five classes of Igs can have a $\kappa$ or $\lambda$ chain.

The sequence of about 110 amino acids near the N-terminus of the heavy and light chains of the antibody varies greatly, and is a variable region (V region); and the remaining amino acid sequence near the C-terminus is relatively stable and is a constant regions (C region). Each light chain variable region (VL) and heavy chain variable region (VH) consists of 3 CDRs and 4 FRs, and the sequence arranged sequentially from the amino terminus to the carboxyl terminus is: FR1, CDR1, FR2, CDR2, FR3, CDR3, and FR4. The three CDRs of the light chain refer to VL CDR1, VL CDR2 and VL CDR3; and the three CDRs of the heavy chain refer to VH CDR1, VH CDR2 and VH CDR3.

Within the light and heavy chains, the variable region and the constant region are linked by a "J" region of about 12 or more amino acids, and the heavy chain further includes a "D" region of about 3 or more amino acids. Each heavy chain consists of a VH and a heavy chain constant region (referred to as HC or CH for short). The heavy chain constant region consists of three domains (respectively referred to as HC1, HC2 and HC3 or CH1, CH2 and CH3 for short). Each light chain consists of a VL and a light chain constant region (referred to as LC or CL for short), and generally, one light chain includes one light chain constant region. The constant region of the antibody can mediate the binding of an immunoglobulin to a host tissue or factor, including the binding of various cells of an immune system (e.g., effector cells) to a first component (C1q) of a classical complement system.

The term "murine antibody" in the present disclosure is a monoclonal antibody against human Sirpα prepared according to the knowledge and skills in the art. In preparation, a test subject is injected with Sirpα antigens, and then hybridomas expressing antibodies with the desired sequence or functional properties are isolated. In a preferred embodiment of the present disclosure, the murine Sirpα antibody or an antigen-binding fragment thereof may further include light chain constant regions of murine $\kappa$, $\lambda$ chains or a variant thereof, or further includes heavy chain constant regions of murine IgG1, IgG2a, IgG2b, IgG2c or IgG3 or a variant thereof.

The term "chimeric antibody" is an antibody formed by fusing the variable region of a murine antibody with the constant region of a human antibody, which can alleviate the immune response induced by the murine antibody. In order to establish a chimeric antibody, a hybridoma that secretes a murine monoclonal antibody should be established first and then the variable region gene is cloned from the mouse hybridoma cells, then the constant region gene of the human antibody is cloned as desired, and the mouse variable region gene is linked with the human constant region gene to form a chimeric gene, the chimeric gene is inserted into a vector, and finally a chimeric antibody molecule is expressed in an eukaryotic or prokaryotic industry system. In a preferred embodiment of the present disclosure, the antibody light chain variable region of the Sirpα chimeric antibody further includes light chain FRs of murine $\kappa$ and $\lambda$ types or a variant thereof. The antibody heavy chain variable region of the Sirpα chimeric antibody further includes heavy chain FRs of murine IgG1, IgG2a, IgG2b, IgG2c, IgG3 or a variant thereof. The constant region of the human antibody can be selected from the heavy chain constant regions of human-derived IgG1, IgG2, IgG3 or IgG4 or a variant thereof, preferably including the heavy chain constant region of human-derived IgG1 or IgG4, or alternatively an IgG1 which changes the activities of ADCC (antibody-dependent cell-mediated cytotoxicity) and CDC (complement dependent cytotoxicity) after amino acid mutation is used. By modifying a Fc segment on the IgG, the ADCC and CDC effector functions of the antibody can be reduced or eliminated, or enhanced. The modification refers to making a mutation in the heavy chain constant region of the antibody, such as a mutation selected from N297A, L234A or L235A of IgG1; IgG2/4 chimera, F235E, L234A/E235A, F243L, or S239D/A330L/I332E of IgG4, etc.

The term "humanized antibody", also known as CDR-grafted antibody, refers to an antibody produced by grafting the CDR sequence of a mouse into variable region framework of a human antibody. Particularly, the CDRs of the Sirpα antibody of the present disclosure are CDR sequences defined according to numbering rules of CCG, Kabat, AbM, Chothia or Contact, etc., which are transplanted into the variable region framework of the human antibody to produce an antibody. Preferably, the light chain and/or heavy chain of the humanized Sirpα antibody of the present disclosure may contain 0-10 back mutations.

As used herein, the term "specifically binds to" in reference to an antibody means an antibody that recognizes a specific antigen but substantially does not recognize or bind to other molecules in a sample. For example, an antibody that specifically binds to an antigen from one species can also bind to that antigen from one or more species. However, this interspecies cross-reactivity does not alter the classification of antibodies according to specificity by itself. In another example, an antibody that specifically binds to an antigen can also bind to different allelic forms of the antigen. However, this cross-reactivity by itself does not alter the classification of antibodies according to specificity. In some cases, the term "specifically binds to" or "specifical binding to" may be used to refer to the interaction between an antibody, protein or peptide and a second chemical substance, meaning that the interaction depends on the presence of a specific structure (e.g., antigenic determinant or epitope) on the chemical substance.

The term "deamidation" refers to the removal of an amino group at a site or at a certain site in a molecule. "deamidation sensitive site" refers to a molecule and a certain site of the molecule that are easier and more prone to deamination.

The term "antigen-binding fragment" refers to an antigen-binding fragment of an antibody and an antibody analog, which generally include at least a portion of the antigen-binding or variable region (e.g. one or more CDRs) of a parental antibody. The antibody fragment retains at least some of the binding specificity of the parental antibody. Typically, the antibody fragment retains at least 10% of the binding activity of the parental antibody when the activity is expressed on a molar basis. Preferably, the antibody fragment retains at least 50%, 60%, 70%, 80%, 90%, 95%, 99% or 100% or more of the binding affinity of the parental antibody for a target. Examples of the antigen-binding fragment include, but are not limited to: Fab, Fab', F(ab')$_2$, a Fv fragment, a linear antibody, a single chain antibody, a nanobody, a domain antibody and a multispecific antibody. Engineered antibody variants are reviewed in Holliger and Hudson (2005) Nat. Biotechnol. 23: 1126-1136.

An antibody molecule includes a bispecific antibody (diabody) and a single chain molecule as well as an antigen-binding fragment of an antibody (e.g., Fab, F(ab')$_2$, scFv and Fv). The antibody molecule includes or consists of one heavy chain and one light chain (referred to in the present disclosure as a half-antibody). Fab', F(ab')$_2$, Fc, Fd, Fv, a single chain antibody (e.g. scFv), a single variable domain antibody, a bispecific antibody (Dab) (bivalent and bispecific) and a chimeric (e.g. humanized) antibody, can be produced by modifying a whole antibody, or they are those antibody molecules synthesized de novo by using a recombinant DNA technique. These functional antibody fragments retain the ability to selectively bind to their corresponding antigens or receptors. The antibodies and antibody fragments can be from any antibody class, including but not limited to IgG, IgA, IgM, IgD and IgE and from any antibody subclass. The preparation of antibody molecules can be monoclonal or polyclonal. The antibody can also be a human antibody, a humanized antibody, a CDR-grafted antibody, or an antibody produced in vitro.

A "Fab fragment" consists of one light chain, the CH1 of one heavy chain, and a variable region. The heavy chain of the Fab molecule cannot form a disulfide bond with another heavy chain molecule. A "Fc" region contains two heavy chain fragments including the CH2 and CH3 domains of an antibody. The two heavy chain fragments are held together by two or more disulfide bonds and by the hydrophobic interaction of the CH3 domain. A "Fab' fragment" contains one light chain, and part of one heavy chain including VH and CH1 domains and the region between the CH1 and CH2 domains, so that an interchain disulfide bond can be formed between the two heavy chains of two Fab' fragments to form an F(ab')$_2$ molecule. A "F(ab')$_2$ fragment" contains two light chains and two heavy chains including part of the constant region between the CH1 and CH2 domains, thereby forming an interchain disulfide bond between the two heavy chains. Therefore, the F(ab')$_2$ fragment consists of two Fab' fragments linked by a disulfide bond between two heavy chains. The term "Fv" means an antibody fragment consisting of the VL and VH domains of a single arm of an antibody, but lacking the constant region.

In some cases, the antigen-binding fragment of an antibody is a single-chain binding fragment (e.g., scFv), in which the VL and VH domains are paired to form a monovalent molecule by a linker that enables them to be produced as a single polypeptide chain [See, for example, Bird et al., Science 242:423-426 (1988) and Huston et al., Proc. Natl. Acad. Sci. USA 85:5879-5883(1988)]. Such scFv molecules can have the general structure: NH$_2$-VL-linker-VH-COOH or NH$_2$-VH-linker-VL-COOH. A suitable linker of the prior art consists of repeated G$_4$S amino acid sequences or variants thereof. For example, a linker having the amino acid sequence (G$_4$S)$_4$ (SEQ ID NO: 61) or (G$_4$S)$_3$ (SEQ ID NO: 60) can be used, but variants thereof can also be used.

The term "multispecific antibody" is used in its broadest sense to encompass an antibody with multiepitope specificity. These multispecific antibodies include, but are not limited to: an antibody including a heavy chain variable region (VH) and a light chain variable region (VL), wherein the VH-VL unit has multiepitope specificity; an antibody having two or more VL and VH regions, wherein each VH-VL unit binds to different targets or different epitopes of the same target; an antibody having two or more single variable regions, each of which binds to a different target or a different epitope of the same target; a full-length antibody, an antibody fragment, a bispecific antibody, a diabody, antibody fragments that are linked covalently or noncovalently, etc.

The antibody disclosed by the present disclosure may also be a single domain antibody. The single domain antibody can include an antibody of which the complementarity determining region is an integral part of a single domain polypeptide. Examples include, but are not limited to, a heavy chain antibody, an antibody that naturally lacks a light chain, a single domain antibody derived from a conventional 4 chain antibody, an engineered antibody, and single domain scaffolds other than those derived from antibodies. The single domain antibody can be any antibody of the prior art, or any single domain antibody in the future. The single domain antibody can be derived from any species, including but not limited to mouse, human, camel, alpaca, goat, rabbit and bovine. According to some aspects, the single domain antibody is a naturally-occurring single domain antibody, referred to as a heavy chain antibody lacking a light chain. For reasons of clarity, such a variable domain derived from a heavy chain antibody naturally lacking a light chain is referred to in the present disclosure as a VHH or a nanobody to distinguish it from the conventional VH of a four-chain immunoglobulin. Such a VHH molecule can be derived from antibodies produced in Camelidae species (e.g., camels, alpacas, dromedaries, llamas and guanacos). Species other than camels can produce a heavy chain antibody naturally lacking a light chain, and such VHHs are also contemplated.

A monoclonal antibody or an antigen-binding fragment can be obtained by recombination using, for example, a hybridoma technology, a recombinant technology, a phage display technology, a synthetic technology (e.g., CDR-grafting), or other existing technologies. Methods of producing and purifying antibodies and antigen-binding fragments are well known and can be found in the prior art, such as the Technical guide for antibody experiment from Cold Spring Harbor. The antigen-binding fragment can likewise be prepared by a conventional method.

"Identity", "homology", "variant sequence" and "mutation" refer to the sequence similarity between two polynucleotide sequences or two polypeptides. When the positions in the two compared sequences are occupied by the same base or amino acid monomer subunit, for example, if each position of two DNA molecules is occupied by adenine, then the molecules are homologous at that position. The percentage of identity between two sequences is a function of the number of matches or homologous positions shared by the two sequences divided by the number of compared positions×100. For example, when sequences are optimally aligned, two sequences are 60% homologous if 6 of 10 positions in the two sequences are matched or homologous. In general, two sequences are compared when the maximum percentage of identity is obtained by aligning them. "Optimize" refers to a mutation that retains or improves the binding of the antibody to the antigen, and in the present disclosure, refers to a mutation that retains, maintains or improves the binding to Sirpα.

The terms "polypeptide", "peptide" and "protein" (if of a single chain) are used interchangeably in the present disclosure. The terms "nucleic acid", "nucleic acid sequence", "nucleotide sequence" or "polynucleotide sequence" and "polynucleotide" are used interchangeably.

The term "mutation" includes the substitution, insertion and/or deletion of amino acids or nucleotides. "Amino acid substitution" and "conservative amino acid substitution" are the substitution of an amino acid residue with another amino acid residue and substitution of an amino acid residue with an amino acid residue having a similar side chain, respectively.

"Lentivirus" as used herein refers to the genus Lentivirus under the Retroviridae family. The Lentiviruses are unique among retroviruses, which can infect nondividing cells; and they can deliver a significant amount of genetic information into the DNA of host cells, so that they are one of the most effective methods of gene delivery vector. HIV, SIV and FIV are all examples of the Lentivirus. A vector derived from the Lentivirus provides a means for achieving a significant level of gene transfer in vivo.

The term "recombinant expression vector" as used herein is a composition that includes an isolated nucleic acid and can be used to deliver the isolated nucleic acid to the interior of a cell. Numerous vectors are known in the art, including, but not limited to, linear polynucleotides, polynucleotides associated with ionic or amphiphilic compounds, plasmids, and viruses. Thus, the term "vector" includes an autonomously replicating plasmid or virus. The term should also be construed to include non-plasmid and non-viral compounds that facilitate transfer of nucleic acids into cells, e.g., polylysine compounds, liposomes, and the like. Examples of a viral vector include, but are not limited to, a adenoviral vector, a adeno-associated viral vector, a retroviral vector, and the like.

The expressions "cell", "cell line" as used in the present disclosure are used interchangeably, and all such designations include progeny. The term "host cell" refers to a cell that can be used for introducing a vector, including but not limited to a prokaryotic cell such as Escherichia coli, a fungal cell such as a yeast cell, or an animal cell such as a fibroblast, a CHO cell, a COS cell, a NSO cell, a HeLa cell, a BHK cell, a HEK 293 cell or a human cell.

The term "transfection" refers to the introduction of an exogenous nucleic acid into a eukaryotic cell. Transfection can be achieved by various means known in the art, including calcium phosphate-DNA co-precipitation, DEAE-dextran-mediated transfection, polybrene-mediated transfection, electroporation, microinjection, liposome fusion, lipofection, protoplast fusion, retroviral infection and biolistics.

"Optional", "any", or "any one" means that the event or environment described later can happen, but it doesn't have to happen. This description includes the occasion where this event or environment happens or doesn't happen. For example, "optionally contains 1 antibody heavy chain variable region" means the antibody heavy chain variable region of a specific sequence may be existed, but doesn't have to be existed. As used in the present disclosure, "a" and "an" are used for referring to one or more grammatical objects in the present disclosure. Unless the content clearly indicates, the term "or" is used in the present disclosure to mean the term "and/or" and is used interchangeably with it. "About" and "approximately" should generally mean the acceptable error degree of the measured quantity in view of the nature or accuracy of the measurement. Exemplary error degree is generally within a range of 10% thereof and more generally within a range of 5% thereof. The methods and compositions disclosed in the present disclosure encompass such polypeptides and nucleic acids that have specified sequences, variant sequences or sequences that are basically the same as or similar to them, for example, sequences that are at least 85%, 90%, 95%, 99% or more identical to the specified sequences. In the context of amino acid sequences, the term "substantially identical" is used in the present disclosure to refer to the first amino acid sequence.

As used herein, the term $EC_{50}$ refers to a concentration for 50% of maximum effect, i.e., the concentration that can cause 50% of the maximal effect. The term $IC_{50}$ refers to a semi-inhibitory concentration, i.e., the inhibitor concentration required to inhibit 50% of the activities of an enzyme, a cell, a cell receptor or the growth of microorganisms.

The pharmaceutical composition of the present disclosure can be prepared into various dosage forms as needed, and can be administered at a dosage beneficial to a patient as determined by physicians according to the type, age, body weight and general disease state of the patient, mode of administration and the like factors. The mode of administration can be, for example, injection or other therapeutic modalities.

The method, composition and combined therapy of the present disclosure can be combined with other active agents or therapeutic modalities. The methods includes administering to a subject the anti-Sirpα antibody molecule of the present disclosure, optionally in combination with one or more inhibitors such as PD-1, PD-L1, PD-L2, LAG-3, CTLA-4, Tim-3 antibodies (immunotherapy) or other tumor therapy antibodies, Her-2, EGFR, VEGF, VEGFR, CLDN18.2 and the like antibodies, as well as ADC (e.g., T-DM1), a bispecific antibody, chemotherapeutic drugs, etc. in an amount effective for treating or preventing diseases (e.g., cancer), and further includes administering an anti-Sirpα antibody molecule, additional active agents or all of them in such an amount or dosage that is higher, lower or equal to the amount or dosage of each active agent used alone (e.g. as monotherapy). The amount or dosage of the anti-Sirpα antibody, additional active agents or all of them is lower (for example, at least 20%, at least 30%, at least 40% or at least 50%) than that of each active agent used alone (for example, as monotherapy).

The anti-Sirpα antibody molecule can be administered in combination with one or more of the following: immune-based strategies, targeted drugs (e.g. a VEGF inhibitor such as a monoclonal antibody against VEGF); a VEGF tyrosine kinase inhibitor such as Sunitinib, Sorafenib and Apatinib; an RNAi inhibitor or an inhibitor of a downstream mediator of VEGF signaling, for example, an inhibitor of a rapamycin mammalian target (mTOR).

As used in the present disclosure, the terms "cancer", "carcinoma", "tumor" are intended to include all types of cancerous growths or tumorigenic processes, metastatic tissues or malignantly transformed cells, tissues or organs, regardless of the type of histopathology or stage of invasiveness. Examples include, but are not limited to, solid tumors, hematologic cancers, soft tissue tumors, and metastatic lesions.

On the basis of conforming to the common knowledge in the art, the aforementioned preferred conditions can be combined arbitrarily to obtain preferred examples of the present disclosure. The reagents and raw materials used in the present disclosure are all commercially available.

The positive progressive effect of the present disclosure is as follows.

1) Compared with the prior art, the antibody or an antigen-binding fragment thereof of the present disclosure has good activity of binding to Sirpα, can block the binding of human Sirpα (including Sirpα-V1 and Sirpα-V2) to human CD47 so that the antibody or an antigen-binding fragment thereof can be developed as a new drug that targets the binding of Sirpα to CD47 to achieve the purpose of treating a tumor, and the antibody or an antigen-binding fragment thereof of the present disclosure can simultaneously binds to the two forms of human Sirpα, Sirpα-V1 and Sirpα-V2 with binding activity significantly higher than that of the prior art. Therefore, the antibody or an antigen-binding fragment thereof of the present disclosure has advantages of many aspects when developed as a drug, and can target more patient populations (a population expressing Sirpα-V1 and/or a population expressing Sirpα-V2).

2) The antibody or an antigen-binding fragment thereof of the present disclosure does not bind to human Sirpβ and Sirpγ; nor does it bind to human T cells. Therefore, the antibody or an antigen-binding fragment thereof of the present disclosure has better selectivity and avoids a side effect caused by off-target effect brought about by clinical binding to T cells.

3) The antibody or an antigen-binding fragment thereof of the present disclosure can strongly bind to a variety of different polymorphisms of Cyno Sirpα, so that the primate *cynomolgus* (cyno) can be selected for use in preclinical safety evaluation research, which brings great convenience to preclinical pharmacology, toxicology and the like research.

4) The results of PTM analysis show that the antibody or an antigen-binding fragment thereof of the present disclosure has the characteristics of low immunogenicity and low risk of druggability.

5) The antibody or an antigen-binding fragment thereof of the present disclosure has a higher expression level after humanization, which provides convenience and cost savings for downstream production and processes. In a preferred embodiment of the present disclosure, the expression level of the humanized antibody of the present disclosure is up to 275 mg/L, which is about 4.5 times higher than those of its chimeric antibody and the antibody OSE-172 in the prior art.

6) The sequence-specific bispecific antibody SBody, which is designed and screened out based on the Sirpα antibody sequence of the present disclosure, can retain the functional activity of the antibody against dual targets, the activity of it of binding to the two targets is close to that of its corresponding monoclonal antibody, and the activity of it of blocking the binding of an antigen to a corresponding ligand is also consistent with that of the corresponding monoclonal antibody; it can effectively inhibit tumor growth; and it has good stability in a preferred formulation. These bispecific antibodies (called SBodies in the present disclosure), which are similar in structure to conventional IgGs, have the same entire Fc as normal antibodies, so that their purification process can be carried out according to those of normal antibodies, and thus the process is simple and has the advantage of low production cost.

In view of the above, the unique properties of the antibody or an antigen-binding fragment thereof of the present disclosure enable the same to be more suitable for the development of a drug for an antibody or an antigen-binding fragment thereof against a human Sirpα target, and as a candidate drug, it can be administered alone or in combination, especially providing a new and even better option for combined immunotherapy of tumors with a PD-1 antibody and the like.

DETAILED DESCRIPTION OF THE PREFERRED EMBODIMENT

Figure 1A:
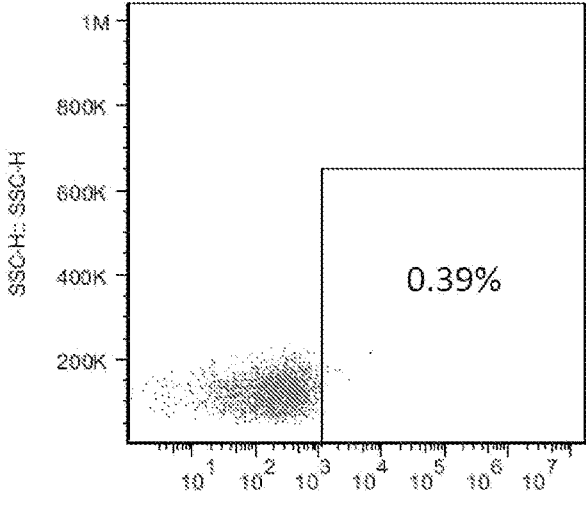
FIG. 1A shows the binding activity of the negative control to human T cells.
Figure 1B:
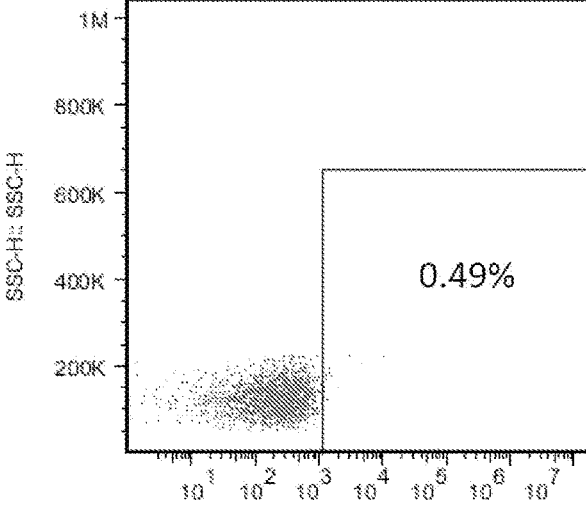
FIG. 1B shows the binding activity of the control antibody 1 (Ref1) to human T cells.

The present disclosure is further described hereafter by way of examples, but the present disclosure is not limited to the scope of the described examples. The experimental methods that do not specify specific conditions in the following examples are selected according to conventional methods and conditions, or according to the description of products.

Example 1 Cloning, Expression and Purification of Antigen and Antibody

The antigens used in the present disclosure are purchased from various different companies as follows.

Sino Biological Inc.: human Sirpα-V1-his (Cat. No.: 11612-H08H), human Sirpα-V1-mFc (Cat. No.: 11612-H38H), mouse Sirpα-his (Cat. No.: 50956-M08H), and human Sirpγ (Cat. No.: 11828-H08H); or Acrobiosystems Co., Ltd.: human Sirpβ-hFc (Cat. No.: SIA-H5257), human Sirpγ-hFc (Cat. No.: SIG-H5253); or Biointron: human CD47-his (Cat. No.: B2048) or obtained by expression and purification of the present disclosure.

The expressed human Sirpα-V1 protein (his, or Fc Tag) sequence is NCBI Reference Sequence: NP_001035111, with a full length of 504 amino acids, of which positions 1-30 are a signal peptide; and the extracellular domain (ECD) is amino acids of positions 31-373. The amino acids of positions 31-137 of the ECD are a Ig-like-V-type region, the amino acids of positions 148-247 are a Ig-like C1-type1 region, and the amino acids of positions 254-348 are a Ig-like C1-type2 region.

The protein sequence of human Sirpα-V2 (his, or Fc tag) is NCBI Reference Sequence: NP_001317657.1, with a full length of 508 amino acids, of which positions 1-30 are a signal peptide; and the ECD is amino acids of positions 31-373. In the extracellular domain, the amino acids of positions 35-145 are a Ig-like 1 region, the amino acids of positions 147-250 are a Ig-like 2 region, and the amino acids of positions 252-333 are a Ig-like 3 region.

The protein sequence of human Sirpβ (his tag) is NCBI Reference Sequence: NP_006056.2, with a full length of 398 amino acids, of which positions 1-29 are a signal peptide; and the ECD region is amino acids of positions 30-371. In the ECD, the amino acids of positions 37-144 are a Ig-like-V-type region, the amino acids of positions 142-253 are a Ig-like region, and the amino acids of positions 265-344 are a Ig C region.

The protein sequence of human Sirpγ (his tag) is NCBI Reference Sequence: AAH64532.1, with a full length of 387 amino acids, of which positions 1-28 are a signal peptide; and the ECD is amino acids of positions 29-360. In the ECD, the amino acids of positions 29-137 are a Ig-like-V-type region, the amino acids of positions 146-245 are a Ig-like C1-type1 region, and the amino acids of positions 252-340 are a Ig-like C1-type2 region.

The protein sequence of NOD mouse Sirpα (his tag) is referred to the article polymorphism in Sirpα modulates engraftment of human hematopoietic stem cells (Nature Immunology, 2007).

Cyno Sirpα (*cynomolgus* Sirpα, *Macaca mulatta* Sirpα) has different forms of polymorphism. In addition to two sequences from the database published by NCBI, the amino acid sequence of the Cyno Sirpα protein of the present disclosure includes 4 polymorphic sequences which are different from the Cyno Sirpα published by NCBI and obtained by collecting different *cynomolgus* monkeys. Also, the binding activities of the antibody of the present disclosure to these different polymorphic forms of the Cyno Sirpα protein are evaluated.

The protein sequence of Cyno Sirpα (his tag) is derived from NCBI database, Reference Sequence: NP_001271679.1 (SEQ ID NO: 62), with a full length of 503 amino acids, of which positions 1-30 are a signal peptide; and the ECD is the amino acids of positions 31-370. In the ECD, the amino acids of positions 38-144 are a Ig-like-V-type region, the amino acids of positions 142-253 are a Ig region, and the amino acids of positions 265-345 are a Ig-C region. NCBI Reference Sequence: NP_001271679.2 (SEQ ID NO: 63) has a full length of 503 amino acids. The two ECD sequences differ by 3 amino acids (polymorphism).

Moreover, in the present disclosure, blood samples of *cynomolgus* monkeys (cynos) were purchased from Zhaoqing Experimental Animal Center, human peripheral blood mononuclear cells (PBMCs) were separated by using SEPMATE 50 (Beijing Office of STEMCELL Technologies Inc., Canada, Cat. No. 86450), then the PBMCs were cultured with RPMI1640 (HYCLONE, Cat. No. SH30809.01) containing 10% FBS (Shanghai Biosun Sci&Tech Co., Ltd., Cat. No. BS-0002-500) until confluence for 3 h, and the adherent macrophages were digested by pancreatin (Shanghai Basalmedia Technologies Co., Ltd., Cat. No. S310JV), then RNA was extracted by a Trizol method for reverse transcription, then the fragment of interest was amplified by PCR, wherein the primers used for PCR were SI-2F: taaacggatctctaGCGAATTCatggagcccgccggcccggccccg (SEQ ID NO: 1) and SI-2R: cggccttgccggcctcGAGCGGCCGCtgtct-gattcggacgaggtagag (SEQ ID NO: 2), and the purified PCR product was cloned into a vector for sequencing, wherein the sequencing primer is p63a-SEQ: cacaggtgtccactcccaggt (SEQ ID NO: 49). Finally, two Cyno Sirpα sequences (polymorphisms) different from those published by NCBI were obtained. Meanwhile, 2 other different Cyno Sirpα sequences (polymorphisms) were obtained from the blood samples of *cynomolgus* monkeys purchased from Hainan Animal Center by the same method.

The base sequence of each Cyno Sirpα protein was subjected to whole gene synthesis (C-terminus linked to 6×his) and cloned into a pTT5 vector (Biovector, Cat #: 102762) for expression, so as to obtain different Cyno Sirpα proteins through purification.

TABLE 1

| Different polymorphic molecules of Cyno Sirpα | |
| --- | --- |
| No. of Cyno Sirpα protein | Sequence number |
| L932 | NP_001271679.1 |
| L933 | XP_015313155.1 |
| L936 | RB3-3 |
| L937 | RB3-5 |
| L938 | RB6-1 |
| L939 | RB6-2 |

The amino acid sequence of the Cyno Sirpα protein (polymorphism) found in the present disclosure:

```
RB3-3 sequence:
                                      (SEQ ID NO: 3)
EEELQVIQPEKSVSVAAGDSATLNCTVTSLIPVGPIQWFRGAGPGRELI

YHQKEGHFPRVTSVSESTKRNNMDFSIHISNITPADAGTYYCVKFRKGS

PDVEVKSGAGTELSVRAKPSAPVVSGPAVRATAEHTVSFTCESHGFSPR

DITLKWFKNGNELSDFQTNVDPAGKSVSYSIRSTARVVLTRRDVHSQVI

CEVAHVTLQGDPLRGTANLSEAIRVPPFLEVTQQSMRADNQVNVTCQVT

KFYPQRLQLTWLENGNVSRTEMASALPENKDGTYNWTSWLLVNVSAHRD

DVKLTCQVEHDGQPAVNKSFSVKVSAHPKEQGSNTAAENTGTNERN

RB3-5 sequence:
                                      (SEQ ID NO: 4)
EEELQVIQPEKSVSVAAGDSATLNCTVSSLIPVGPIQWFRGAGPGRELI

YNLKEGHFPRVTPVSDPTKRNNMDFSIRISNITPADAGTYYCVKFRKGS

PDVELKSGAGTELSVRAKPSAPVVSGPAVRATAEHTVSFTCESHGFSPR

DITLKWFKNGNELSDVQTNVDPAGKSVSYSIRSTARVLLTRRDVHSQVI

CEVAHVTLQGDPLRGTANLSEAIRVPPFLEVTQQSMRADNQVNVTCQVT

KFYPQRLQLTWLENGNVSRTEMASALPENKDGTYNWTSWLLVNVSAHRD

DVKLTCQVEHDGQPAVNKSFSVKVSAHPKEQGSNTAAENTGTNERN

RB6-1 sequence:
                                      (SEQ ID NO: 5)
EEELQVIQPEKSVSVAAGESATLNCTATSLIPVGPIQWFRGVGPGRELI

YHQKEGHFPRVTPVSDPTKRNNMDFSIRISNITPADAGTYYCVKFRKGS

PDVELKSGAGTELSVRAKPSAPVVSGPAVRATAEHTVSFTCESHGFSPR

DITLKWFKNGNELSDFQTNVDPAGKSVSYSIRSTARVVLTRRDVHSQVI
```

-continued

CEVAHVTLQGDPLRGTANLSEAIRVPPFLEVTQQSMRADNQVNVTCQVM

KFYPQRLQLTWLENGNVSRTEMASALPENKDGTYNWTSWLLVNVSAHRD

DVKLTCQVEHDGQPAVNKSFSVKVSAHPKEQGSNTAAENTGTNERN

RB6-2 sequence:

(SEQ ID NO: 6)

EEELQVIQPEKSVSVAAGESATLNCTATSLIPVGPIQWFRGVGPGRELI

YSQKEGHFPRVTPVSDPTKRNNMDFSIRISNITPADAGTYYCVKFRKGS

PDVELKSGAGTELSVRAKPSAPVVSGPAVRATAEHTVSFTCESHGFSPR

DITLKWFKNGNELSDFQTNVDPAGKSVSYSIRSTARVVLTRRDVHSQVI

CEVAHVTLQGDPLRGTANLSEAIRVPPFLEVTQQSMRADNQVNVTCQVT

KFYPQRLQLTWLENGNVSRTEMASALPENKDGTYNWTSWLLVNVSAHRD

DVKLTCQVEHDGQPAVNKSFSVKVSAHPKEQGSNTAAENTGTNERN

The human CD47 (hFc/his tag) protein sequence was NCBI Reference Sequence: NP_001768.1, with a full length of 323 amino acids, of which positions 1-18 were a signal peptide; and the ECD was amino acids of positions 19-141.

The human PD-1 (hFc/his tag) protein sequence was NCBI Reference Sequence: NP_005009.2, with a full length of 288 amino acids, of which positions 1-20 were a signal peptide; and the ECD was amino acids of positions 21-167.

The human PD-L1 (hFc/his tag) protein sequence was NCBI Reference Sequence: NP_054862.1, with a full length of 290 amino acids, of which positions 1-18 were a signal peptide; and the ECD was amino acids of positions 19-239.

The proteins with hFc tag used in the present disclosure were expressed with a IgG1 Fc region at the C-terminus, and the proteins with his tag were expressed with 6×his tag at the C-terminus.

The antibodies used in the present disclosure, including a positive control antibody 1 (referred to as Ref1 for short, namely OSE-172, with a sequence from WO2017178653A2, #55 light chain, and #42 heavy chain, wherein #represents the sequence number in the reference) and a positive control antibody 2 (referred to as Ref2 for short, with a sequence from SIRP29 in US20140242095A1, #6 light chain, and #12 heavy chain, acting as a positive control when binding to Sirpγ), were all expressed and purified by the present disclosure.

A pTT5 vector (Biovector, Cat #: 102762) was used as an expression vector. The expressed recombinant protein, and light and heavy chain sequences of the antibody were cloned into the pTT5 vector, transiently transfected into HEK293F cells (Life Technologies Cat. No. 11625019, hereinafter referred to as 293F cells for short) for expression, and then purified.

Specifically, expanding culture of the 293F cells was conducted in a Gibco FreeStyle 293 Expression Medium (Gibco, Cat #: 12338018) medium. Before the start of the transiently transfection, the cell concentration was adjusted to $8 \times 10^5$ cells/mL, and cultured in 1% FBS (AusGeneX FBS Excellent, Supplier: AusGeneX, China, Cat #: FBSSA500-S) in a shaker at 37° C. under 8% $CO_2$ for 24 h, with the survival rate being >95% by microscopic examination again, and the cell concentration being $1.2 \times 10^6$ cells/mL.

A 300 mL culture system of cells was prepared, wherein 15 mL of Opti-MEM (Gibco, Cat #: 31985070) into each 150 μg (the amount of a single plasmid was 300 μg if it was a recombinant protein) of the heavy chain, light chain plasmids or fused protein plasmids, and filtered through a 0.22 μm filter for sterilization. Then another 15 mL of Opti-MEM was taken, dissolved into 600 μL of 1 mg/mL PEI (Polysciences, Inc, Cat #: 23966-2), and then allowed to stand for 5 min. The PEI was slowly added into the plasmids and incubated at room temperature for 10 min, and the mixed solution of the plasmids and the PEI was slowly added dropwise while shaking the culture flask. A sample was collected after culture in the shaker at 37° C. under 8% $CO_2$ for 5 days and centrifuged at 3300G for 10 min, and the supernatant was taken for purification.

Purification of antibody or -Fc fusion protein: The sample was centrifuged at a high speed to remove impurities, and a gravity column (Sangon, Cat #: F506606-0001) containing protein A (bselect, GE Healthcare Life Science, Cat #: 71-5020-91 AE) was equilibrated by rinsing with 2-5 times the volume of the column of PBS pH7.4. The sample passed through the column. The column was rinsed with 5-10 times the volume of the column of PBS (Sangon, CAT #: B548117-0500). Then the protein of interest was eluted with 0.1 M acetic acid at pH3.5, subsequently adjusted to neutrality with Tris-HCl at pH8.0, determined for the concentration with a microplate reader, subpackaged and stored for later use.

Purification of His Tagged protein: The sample was centrifuged at high speed to remove impurities. Equilibration of nickel column (Ni smart beads 6FF, Changzhou Smart-Lifesciences Biotechnology Co., Ltd., Cat #: SA036010): the nickel column was equilibrated by rinsing with 2-5 times the volume of the column of a PBS pH7.4 solution containing 10 mM imidazole and 0.5 M NaCl. The supernatant of the sample passed through the column. Rinsing of impurity protein: the chromatographic column was rinsed with a PBS pH7.4 solution containing 10 mM imidazole and 0.5 M NaCl to remove non-specifically bound impurity proteins, and the effluent was collected. The protein of interest was eluted with PBS pH7.4 containing 250 mM imidazole and 0.5 M NaCl. Buffer replacement: the eluted protein of interest was centrifuged at 12,000 g for 10 min through an ultrafiltration tube (ultrafiltration tube, Merck Millipore, Cat #: UFC500308), then added with 1 mL of PBS, determined for the concentration, subpackaged and stored for later use.

Example 2 Construction of High Expression Cell Strain and Detection of Cell Activity (ELISA)

The high expression cell strains used in the present disclosure were all constructed by the inventors themselves through the stable cell strain construction platform of our company. The construction process would be explained below by taking the construction of a human Sirpα high expression strain as an example. The specific steps were as follows:

On the 1st day of the experiment, 293T cells (The cell bank of National Collection of Authenticated Cell Cultures of Chinese Academy of Sciences, Cat #: GNHu17) were inoculated into two 6 cm culture dishes, with the number of cells in each culture dish reaching $7.5 \times 10^5$. On the 2nd day, each 4 μg of a packaging plasmid (BioVector plasmid vector strain cell gene collection centers pGag-pol, pVSV-G and the like) and a plasmid pBabe-hSirpα cloned with a human Sirpα gene were added to Opti-MEM (Thermo Fisher Scientific, Cat #: 31985070) to make a final volume of 200 μL. Another 200 μL of OPTI-MEM was prepared, added with 36 μL of a transfection reagent fectin (Shanghai Basalmedia Technologies Co., Ltd., CAT #: F210), evenly mixed and allowed to stand at room temperature for 5 min. Then, the mixture (200 μl per dish) was added dropwise into the cultured 293T cells. On the 3rd day, the 293T cell culture medium was replaced with 4 mL of a DMEM high-sugar medium (Shanghai Basalmedia Technologies Co., Ltd., Cat #: L130KJ). On the 4th day, CHO-K1 cells (The cell bank of National Collection of Authenticated Cell Cultures of Chinese Academy of Sciences, CAT #: SCSP-507) were inoculated into a 10 cm culture dish to make the number of cells reach $5\times10^5$. On the 5th day, the supernatant of 293T cells (viruses) was collected, filtered through a 0.45 μm filter membrane into cultured CHO-K1 cells, meanwhile added with 10 μg/mL of polybrene (Yeasen Biotechnology (Shanghai) Co., Ltd., Cat #: 40804ES76), mixed uniformly and placed into an incubator for 3-4 h, and then the medium was replaced with a DMEM/F12 10% FBS medium (Shanghai Basalmedia Technologies Co., Ltd., Cat #: L310KJ). On the 7th day, CHO-K1 cells were passaged, and the passaged cells were added with 10 μg/mL of puromycin on the 8th day for screening (Shanghai Basalmedia Technologies Co., Ltd., Cat #: S250J0). After 2-3 days, a large number of cells died, the medium was replaced to continue the culture until the cells no longer died, a large number of cells were expanded, and monoclonal cell strains were screened, subjected to expanding culture, and cryopreserved for seed preservation.

The amino acid sequence of human Sirpα (pBabe-hSirpα-V1) used in this example was NP_001035111, with a full length of 1-504 amino acids, of which positions 1-30 were a signal peptide; and the positions 31-504 were the protein sequence expressed by the CHO-K1 h Sirpα+ cell line constructed by the present disclosure.

hSirpα+ Cell Binding Activity (ELISA) Assay:

The cells obtained above, i.e., the monoclonal cell strains with high expression of human Sirpα, were subjected to expanding culture, then plated onto a 96-well plate in accordance with $10\times10^4$/well, and incubated overnight in an incubator at 37° C. Then the supernatant was discarded, and the cell pellet was fixed with 100 μL/well of an immunostaining fix solution (Shanghai beyotime Biotechnology Co., Ltd., CAT #: P098) at room temperature for half an hour. The cells were washed once with PBS (Shanghai Basalmedia Technologies Co., Ltd., CAT #: B320), then blocked in 230 μL of 5% milk at 37° C. for 2 hours, and washed with PBST for three times. Each well was added with 50 μL of 5-fold gradient dilution of the sample to be tested at 10 μg/mL. after incubation at 37° C. for 1 hour, the well was washed with PBST for 5 times. The well was added with Anti-human HRP (Jackson Immuno Research, 115-035-003) 1:2500 at 50 μL/well, incubated at 37° C. for 1 hour, and then washed with PBST for 5 times. Each well was added with 50 μL of TMB Surmodic, Cat #: TTMB-1000-01) for color development, and added with 1 M $H_2SO_4$ at 50 μL/well to stop the reaction. The readings on a microplate reader (MultiskanGO Thermo, Model 51119200) were subjected to data analysis by GraphPad prism 5.

Example 3 Assay of Binding of Anti-Sirpα Antibody to Antigen (ELISA)

Different antigens (recombinant proteins) such as the human Sirpα-V1-hFc, Sirpα-V1-his, Sirpα-V2-his, Sirpβ-his, Sirpγ-his, monkey Sirpα-his (cynoSirpα-his) or NOD-mSirpα-his described in Example 1 were diluted with a PBS buffer at pH7.4 to concentrations of 1 μg/mL, 2 μg/mL or 5 μg/mL, added into a 96-well ELISA plate (Corning®, CLS3590-100EA) at a volume of 50 μL/well, and placed in an incubator at 37° C. for 2 hours. After the liquid was discarded, the wells were added with a blocking solution of 5% skimmed milk (skimmed milk powder available from Bright Dairy) diluted with PBS at 230 μL/well, and incubated in an incubator at 37° C. for 3 hours, or placed overnight at 4° C. (for 16-18 hours) for blocking. The blocking solution was discarded, and the plate was washed with a PBST buffer (pH7.4 PBS containing 0.05% Tween-20) for 5 times, then added with 50 μL/well of the supernatant (containing a detection antibody) or 10 μg/mL of the starting 5-fold gradient dilution of the antibody to be tested, and incubated at 37° C. for 1 hour. The plated was washed with PBST for 5 times, added with 50 μL/well of Anti-mouse or human HRP secondary antibody (Jackson Immuno Research, Cat #: 115-035-003 or 109-035-003) diluted at 1:2500, and incubated at 37° C. for 1 hour. The plated was washed with PBST for 5 times, then added with 50 μL/well of a TMB chromogenic substrate (KPL, 52-00-03), incubated at room temperature for 10-15 min, added with 50 μL/well of 1 M $H_2SO_4$ to stop the reaction, and read by a MULTISKAN Go microplate reader (ThermoFisher, Cat #: 51119200) for the absorbance value at 450 nm, and then a clone with high binding activity was selected or a $EC_{50}$ value was calculated according to the OD value.

Example 4 Assay of Activity of Anti-Sirpα Antibody in Preventing the Binding of Sirpα to CD47

The recombinant proteins such as human Sirpα-V1-hFc/Sirpα-V1-his were diluted to concentrations of 5 μg/mL or 2 μg/mL respectively with a PBS buffer at pH 7.4, and then added into a 96-well ELISA plate (Corning®, CLS3590-100EA) at a volume of 50 μL/well, and placed in an incubator at 37° C. for 2 hours. After the liquid was discarded, the wells were added with a blocking solution of 5% skimmed milk (skimmed milk powder available from Bright Dairy) diluted with PBS at 230 μL/well, and incubated in an incubator at 37° C. for 3 hours, or placed overnight at 4° C. (for 16-18 hours) for blocking. The blocking solution was discarded, and the plate was washed with a PBST buffer (pH7.4 PBS containing 5% Tween-20) for 5 times, then added with 25 μL/well of the supernatant (containing a detection antibody) or 100 μg/mL of the starting 3-fold gradient dilution of the antibody to be tested, and 25 μL/well of Biotin-labeled CD47-hFc at a concentration of 4 μg/mL or 3 μg/mL of CD47-his, mixed uniformly, and then incubated in an incubator at 37° C. for 1 hour. The plate was washed for 5 times, added with 50 μL/well of a streptavidin-TRP secondary antibody (GenScript, M00091) or anti-his-RP secondary antibody (GenScript, A00612) diluted at 1:1000, incubated at 37° C. for 1 hour, and then washed with PBST for 5 times. Each well was added with 50 μL of TMB (Surmodic, Cat #: TTMB-1000-01) for color development, and added with 50 μL/well of 1 M $H_2SO_4$ to stop the reaction. The readings on a microplate reader (MultiskanGO Thermo, Model 51119200) were subjected to data analysis by GraphPad prism 5.

Example 5 Assay of Binding of Anti-Human Sirpα Antibody to Human T Cells

The T cells used in the present disclosure were isolated from the peripheral blood of healthy volunteers with SEP-MATE 50 (Beijing Office of STEMCELL Technologies Inc., Cat. No. 86450), and cryopreserved with a cryopreservation solution (RPMI1640 medium:FBS:DMSO=5:4:1) in a liquid nitrogen tank for later use. The cryopreserved PBMC cells were taken, thawed at 37° C., then added into 3 mL of a FACS buffer (1×PBS+2% FBS), and centrifuged at 1,000 rpm for 5 min, the supernatant was discarded, the cells were resuspended in the FACS buffer for counting, and the density was adjusted to 1×10⁶ cells/mL. PBMCs were added into a U-shaped 96-well plate at 100 µL cells/well, and added with the antibody to be detected so that the final concentrations thereof are 10 µg/mL, 1 µg/mL and 0 µg/mL respectively. They were mixed uniformly, then incubated at room temperature for 20 min, and centrifuged at 2,000 rpm for 5 min. The supernatant was discarded, and the cell pellet was resuspended by adding 100 µL of the FACS buffer, and centrifuged at 2,000 rpm for 5 min. The supernatant was discarded, and the cell pellet was added with 50 µL of PE anti-human IgG Fc (Biolegend, Cat. No.: 409304) diluted at 1:200, mixed uniformly, and incubated with protected from light at room temperature for 20 min. The mixture was centrifuged at 2,000 rpm for 5 min. The supernatant was discarded, and the cell pellet was washed once with 100 µL of the FACS buffer, resuspended with 100 µL of the FACS buffer, and read by a flow cytometer (Novosampler™ pro, model: NS200). The assay data was processed with Novo-Express. Taking the sample well with the antibody concentration of 0 µg/mL as the negative control, based on this, the proportion of T cells specifically bound with the antibody to be tested was calculated.

Example 6 Discovery of Anti-Human Sirpα Antibody

In the present disclosure, human Sirpα-V1-mFc (Sino Biological Inc., Cat. No.: 11612-H38H) and hSirpα-V2-hFc (as expressed in Example 1) recombinant proteins were used as antigens. After the mice were subjected to cross immunization with a Freund's complete adjuvant for 4 times, the cells were subjected to electrofusion and screened for fused hybridomas, so that the clones with good binding activity to hSirpα-V1 were screened out from tens of thousands of hybridoma clones. After further screening, it was unexpectedly found that a clone could simultaneously bind to human Sirpα-V1 and human Sirpα-V2, had blocking activity, and did not bind to human PBMCs (T cells). Further, monoclonal cell strains are obtained from these unexpectedly discovered hybridoma clones through multiple times of sub-cloning, antibody sequences are extracted from the monoclonal cell strains, and expressed and purified to obtain the murine antibody of the present disclosure.

Specifically, the 4 weeks old female SJL mice for experimental use, were purchased from Beijing Vital River Laboratory Animal Technology Co., Ltd., with the animal production license number: SCXK (Beijing) 2016-0011. After the mice were purchased, they were reared in a laboratory environment for 1 week under adjustment of a daytime light/night dark cycle, at a temperature of 20-25° C. and humidity of 40-60%. The mice were divided into 3 mice/group/cage. The mice were immunized with the antigen prepared in Example 1. The first-immune adjuvant was a Freund's complete adjuvant (Sigma-Aldrich, SIGMA F5506-10M), and the second-immune starting adjuvant was a Freund's incomplete adjuvant (Sigma-Aldrich, SIGMA F5881-10M). The ratio of the antigen to the adjuvant was 1:1 (v/v). The mice were subjected to first immunization at 100 µL/25 µg/mouse, and second, third, and fourth immunization respectively at 100 µL/12.5 µg/mouse, through intramuscular injection in a lower leg. 3 days before fusion, the mice were subjected to booster immunization at 100 µL/25 µg/mouse. The immunization times were days 0, 14, 28, 42, and 56 (booster immunization). On days 36 and 50, the serum antibody titer of the mice was detected by the ELISA method of Example 3, and the mice with high serum antibody titer which was at a plateau were selected for spleen cell fusion. Spleen lymphocytes were fused with myeloma cells Sp2/0 (ATCC® CRL-8287™) to obtain hybridoma cells. The hybridoma cells were plated onto a 96-well plate, and then screened to obtain preferred clones.

The hybridoma cell strains were subjected to primary screening, wherein the binding activity of the antibody in the supernatant secreted by the hybridoma cell strains to human Sirpα was detected by the ELISA method of Example 3 (partial binding data was shown in Table 2), and the clones with good activity were selected. The supernatant was taken, and the activity of the secreted antibody in blocking the binding of hSirpα to hCD47 (Blocking activity) was detected by the method of Example 4, and meanwhile the binding activity of it to human Sirpα-V2 was also detected. The preferred clones were further subjected to limiting dilution to obtain monoclonal antibody cell strains, and partial of the results were shown in Table 3.

TABLE 2

| The binding activity of the supernatant of the hybridoma fusion cells (clones) to hSirpα-V1 ($OD_{450}$ value) | |
| --- | --- |
| Initial clone number | ELISA value |
| 1E6 | 1.58 |
| 2D9 | 1.52 |
| 3C6 | 1.22 |
| 3B8 | 1.6 |
| 3C11 | 2.49 |
| 4C1 | 3.0 |
| 5G7 | 1.54 |
| 5E 9 | 1.56 |
| 5B10 | 1.71 |
| 6H1 | 1.57 |
| 6F12 | 1.59 |
| 7G4 | 1.32 |
| 7H4 | 1.85 |
| 8C4 | 2.2 |
| 8H4 | 2.14 |
| 8H7 | 2.11 |
| 9H1 | 2.48 |
| 9F8 | 1.25 |
| 9G8 | 2.25 |
| 9H10 | 2.02 |
| 10A3 | 1.12 |
| 10G4 | 1.85 |
| 10Q5 | 1.98 |
| 10C11 | 2.39 |
| 11H1 | 1.4 |
| 12C1 | 1.57 |
| 12E 2 | 1.22 |
| 12C3 | 1.56 |
| 12D7 | 1.54 |
| 13F10 | 1.0 |
| 13A11 | 1.24 |
| 13C11 | 1.7 |
| 14A4 | 1.41 |
| 14H6 | 1.81 |
| 15Q6 | 1.53 |
| 16G12 | 1.28 |

TABLE 3

Data of the binding activity of the supernatant of the hybridoma fusion to hSirpα-V2, and blocking activity of the same ($OD_{450}$ value)

| Initial clone number | ELISA value (activity of binding to hSirpα-V2) | activity of blocking the binding of hSirpα to hCD47 |
|---|---|---|
| 1E6 | 1.09 | 0.85 |
| 3C11 | 1.02 | 0.83 |

TABLE 3-continued

Data of the binding activity of the supernatant of the hybridoma fusion to hSirpα-V2, and blocking activity of the same ($OD_{450}$ value)

| Initial clone number | ELISA value (activity of binding to hSirpα-V2) | activity of blocking the binding of hSirpα to hCD47 |
|---|---|---|
| 4C1 | 0.92 | 0.73 |
| 5G7 | 1.24 | 0.65 |
| 5B10 | 0.07 | 0.24 |
| 6H1 | 1.09 | 0.79 |
| 6F12 | 1.05 | 0.68 |
| 8C4 | 1.25 | 0.79 |
| 8H4 | 1.27 | 0.75 |
| 9H1 | 1.0 | 0.75 |
| 9F8 | 0.99 | 0.75 |
| 9G8 | 1.0 | 0.72 |
| 9H10 | 1.0 | 0.69 |
| 10C11 | 1.0 | 0.73 |
| 12C1 | 0.89 | 0.69 |
| 12D7 | 1.03 | 0.78 |
| 14A4 | 0.87 | 0.75 |
| 14H6 | 1.25 | 0.33 |
| 15Q6 | 0.87 | 0.68 |
| 16G12 | 0.99 | 0.78 |

Partial of the primary screening data was listed in Table 2. The data showed that many hybridoma fusion cells exhibited very high binding activity in the primary screening and very high ELISA reading values ($OD_{450}$ above 2), such as 4C1, 8C4, 8H7, 9H1 and the like clones. However, it had been found by further screening that almost all of the clones either had low binding activities to hSirpα-V2, or did not have the blocking activity of blocking the binding of hSirpα to hCD47 (when the $OD_{450}$ value of the blocking activity was lower and had the greater difference from the ELISA value, the better blocking activity was indicated). See Table 3.

Very surprisingly, it was found that the clone 14H6 with better binding activity to hSirpα-V1 (Table 2, with the $OD_{450}$ value of 1.81) showed very strong binding activity to hSirpα-V2 (Table 3, with the $OD_{450}$ value of 1.25), and was able to block the binding of hSirpα to hCD47 (with the $OD_{450}$ value of 0.33) very well.

This clone was subjected to multiple times of limiting dilution, with each time of dilution being conducted for 7-10 days. After the clones were proliferated, the antibody (supernatant) secreted by each clone was re-detected by the ELISA method for the binding activities to different Sirpαs and the blocking activity of the same. The results were shown in Table 4.

TABLE 4

Screening activity of preferred hybridoma cell subclones

| Subclone number | Activity of binding to hSirpα-V1 | Activity of binding to hSirpα-V2 | Activity of binding to hSirpγ | Activity of blocking the binding of hSirpα to CD47 (dimer) | Activity of blocking the binding of hSirpα (dimer) to CD47 |
|---|---|---|---|---|---|
| 14H6E5H9F6E3 | 1.1 | 1.64 | 0.11 | 0.48 | 0.075 |
| 14H6E5H9F6G4 | 1.2 | 1.4 | 0.081 | 0.49 | 0.10 |
| 14H6E5H9F6E5 | 1.11 | 1.3 | 0.089 | 0.44 | 0.071 |
| 14H6E5H9F6E11 | 1.15 | 1.4 | 0.092 | 0.46 | 0.072 |
| 14H6E5B5C8G2 | 1.27 | 1.25 | 0.099 | 0.42 | 0.069 |
| 14H6E5B5C8G4 | 1.23 | 1.29 | 0.082 | 0.43 | 0.083 |
| 14H6E5B5C8F5 | 1.3 | 1.2 | 0.091 | 0.41 | 0.067 |
| 14H6E5B5C8G5 | 1.37 | 1.34 | 0.085 | 0.42 | 0.08 |

The aforementioned results indicated that the antibody secreted by the monoclonal cell strain obtained from 14H6 through multiple times of subcloning retained the activities of binding to hSirpα-V1 and hSirpα-V2, and exhibited the activities of blocking the binding of hSirpα-V1-his to hCD47-Fc (dimer) and blocking the binding of hSirpα-V1-hFc (dimer) to hCD47-his.

Even more unexpectedly, the antibodies secreted by these monoclonal cell strains did not bind to Sirpγ (in Table 4, the value of the activity of binding to hSirpγ was below 0.1, i.e., the background value). It indicated that the antibody of the present disclosure had very good selectivity to Sirpα and Sirpγ.

In the present disclosure, the antibody sequence was further extracted from 14H6E5B5C8G2, one of the subclones of 14H6, to obtain the preferred murine mab14 antibody sequence of the present disclosure, which was described specifically in the following examples.

Example 7 the Extraction, Analysis and Identification of Antibody Sequence of Murine Anti-Human Sirpα Antibody mab14

The process of extracting an antibody sequence from the preferred monoclonal cell strain obtained from the aforementioned hybridoma 14H6 subclones is a method commonly used by those skilled in the art. Specifically, the aforementioned monoclonal cell strains were collected and subjected to expanding culture, then $1 \times 10^6$ cells were taken, and RNAs were extracted with Trizol (Invitrogen, 15596-018) (according to the steps of the instructions of the kit). The extracted RNAs were reverse transcribed into cDNAs, and the reverse transcription kit was purchased from Sangon (Shanghai) Co., Ltd., Cat #: B532435. PCR amplification was performed by using the cDNAs obtained by reverse transcription as templates. The amplified products were sequenced, and the base/coding sequences of the light and heavy chain variable regions of the mab14 antibody were obtained respectively (as follows). The primers as used are referred to the manual TB326 Rev. C0308 published by Novagen.

The base sequence of the light chain variable region of the murine monoclonal antibody mab14 obtained in the preferred hybridoma cell strain of the present disclosure (the bold part was the coding sequence):

(SEQ ID NO: 7)
Taatggtgtccctcagctcagttccttggtctcctgttgctctgttttc aaggtaccagatgtgatatccagatgacacagactacatcctccctgtc tgcctctctgggagacagagtcaccatcagttgcagggcaagtcaggac attaggaattatttaaactggtatcagcagaagcagatggaactgtta aactcctgatctacttcacatcaacattacactcaggagtcccatcaag gttcagtggcagtgggtctggaacagattattctctcaccattagcaac ctggaacaagaagatattgccacttacttttgccaacagggtaatacgc ttccgtggacgttcggtggaggcaccaagctggaaatcaaacgggctga tgctgcaccaactgtatccatcttcccaccatccagtgagcagttaaca tctggaggtgcctcagtcgtgtgcttctgaacaactctaccccaaagac atcaaggacct The base sequence of the heavy chain variable region of the murine monoclonal antibody mab14 obtained in the preferred hybridoma cell strain of the present disclosure (the bold part was the coding sequence):

(SEQ ID NO: 8)
Tcatgggatggagctgtatcatgttctttttggtagccgcagctacagg tgtccactcccaggtccatctgcagcagcctggggctgagcttgtgaag cctggggcttcagtgaagttgtcctgcaaggcttctggctacaatttca acatctactggataaattgggtgaagcagaggcctggacaaggccttga gtggattggaaatatttatcctagtagtattagtactaactacaatgag aagttcaagacgaaggccacactgactgtagacaaatcctccaacacag tctacatgcagttcagcagcctgacatctgaggactctgcggtctatta ttgtgcgcgatcggagggaacttactatggtggtcgctacgaggggggac tggtttggttactggggccaagggactctggtcactgtctctgcagcca aaacaacaccccatcagtctatccactggcccctgggtgtggagatac aactggttcctccgtgactctgggatgcctggtcaagggctactgccga gtcgaagttcc The amino acid sequences encoded by the base sequences of the light and heavy chain variable regions of the murine monoclonal antibody mab14 obtained by the present disclosure were as shown in SEQ ID NO: 9 and SEQ ID NO: 10 below.

The amino acid sequence of the light chain variable region of the murine monoclonal antibody mab14 obtained in the preferred hybridoma cell strain of the present disclosure:

(SEQ ID NO: 9)
DIQMTQTTSSLSASLGDRVTISCRASQDIRNYLNWYQQKPDGTVKLLIY

FTSTLHSGVPSRFSGSGSGTDYSLTISNLEQEDIATYFCQQGNTLPWTF

GGGTKLEIK

The amino acid sequence of the heavy chain variable region of the murine monoclonal antibody mab14 obtained in the preferred monoclonal hybridoma cell strain of the present disclosure:

(SEQ ID NO: 10)
QVHLQQPGAELVKPGASVKLSCKASGYNFNIYWINWVKQRPGQGLEWIG

NIYPSSISTNYNEKFKTKATLTVDKSSNTVYMQFSSLTSEDSAVYYCAR

SEGTYYGGRYEGDWFGYWGQGTLVTVSA

The light and heavy chain variable region sequences of the aforementioned antibody of the present disclosure and the constant regions of different IgG types, for example human IgG1 (hIgG1), human IgG2 (hIgG2), human IgG3 (hIgG3) or human IgG4 (hIgG4), human light chain κ and λ types; murine mIgG1, mIgG2 or mIgG3, murine light chain κ and λ types, etc. were recombined, expressed and purified to obtain an entire human-murine chimeric antibody and a murine antibody. In the present disclosure, taking the heavy chain constant region being hIgG4 and the light chain being of the κ type as an example, the human-murine chimeric antibody mab14c was obtained according to the expression and purification methods of Example 1. The binding activities of mab14c to hSirpα-V1, hSirpα-V2 and hSirpα+ cells and the activity of the same in blocking the binding of hSirpα to CD47 were detected by the methods of Example 2, Example 3 and Example 4, and compared with those of the control antibody 1. The results were shown in Table 5.

TABLE 5

| Activity analysis of the human-murine chimeric antibody mab14c of the present disclosure | | | | | |
| --- | --- | --- | --- | --- | --- |
| Sample name | hSirpα-V1, EC$_{50}$, nM | hSirpα-V2, EC$_{50}$, nM | hSirpα+ cell, EC$_{50}$, nM | Blocking binding of hSirpα to hCD47 (dimer), IC$_{50}$, nM | Blocking binding of hSirpα (dimer) to hCD47, IC50, nM |
| mab14c | 0.16 | 0.14 | 0.29 | 5.54 | 5.7 |
| Ref1 | 0.17 | No binding | 0.37 | 4.58 | 4.55 |

The aforementioned results showed that it was unexpectedly found by the present disclosure the human-murine chimeric antibody mab14c could not only block the binding of Sirpα to human CD47, but also have good binding activity to all of hSirpα-V1, hSirpα-V2 and hSirpα+ cells. This was different from Ref1, which did not bind to hSirpα-V2.

Furthermore, the binding activities of mab14c to the muSirpα of NOD mice and different polymorphisms of Cyno Sirpαs (including L932, L933 and L936-L939) were detected by the method of Example 4, and the results were shown in Table 6.

TABLE 6

Analysis of the binding activity of the antibody mab14c of the present disclosure to murine and Cyno Sirpαs (EC$_{50}$, nM)

| Sample name | NOD-muSirpα | L932 | L933 | L936 | L937 | L938 | L939 |
|---|---|---|---|---|---|---|---|
| mab14c | No binding | 0.10 | 0.14 | 0.099 | 0.099 | No binding | No binding |
| Ref1 | No binding | No binding | No binding | No binding | faint binding | faint binding | weak binding |

Note:

it was faint binding when the EC$_{50}$ was greater than 10 nM and less than 50 nM (10 nM ≤ EC$_{50}$ < 50 nM);

it was weak binding when the EC$_{50}$ was between 2-10 nM (i.e., 2 nM ≤ EC$_{50}$ < 10 nM;

and it was no binding when the EC$_{50}$ was greater than 50 nM (EC$_{50}$ ≥ 50 nM) or no signal value was detected.

The aforementioned results showed that the antibody mab14c of the present disclosure had very good binding to 4 of 6 polymorphic proteins of *cynomolgus* (cyno) Sirpα, which was significantly different from that of Ref1, which did not bind to any of these 6 Cyno Sirpαs. In the preclinical research stage of new drug development, it was necessary to select related primate species for preclinical research. If it did not bind to the protein of the primate such as cyno (the most commonly used primate), the primate could not be selected for preclinical research, which would bring great inconvenience to the preclinical research. Therefore, the antibody of the present disclosure brought great convenience to the preclinical research since it bound to various polymorphic proteins of Cyno Sirpα.

Figure 1C:
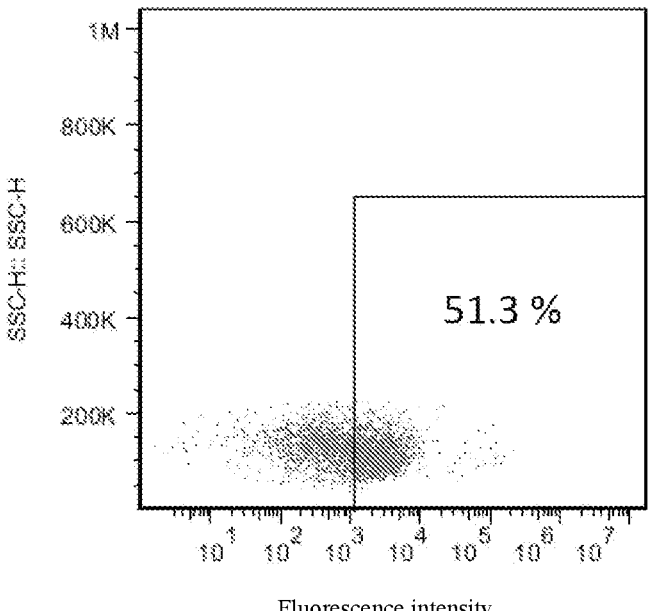
FIG. 1C shows the binding activity of the control antibody 2 (Ref2) to human T cells.
Figure 1D:
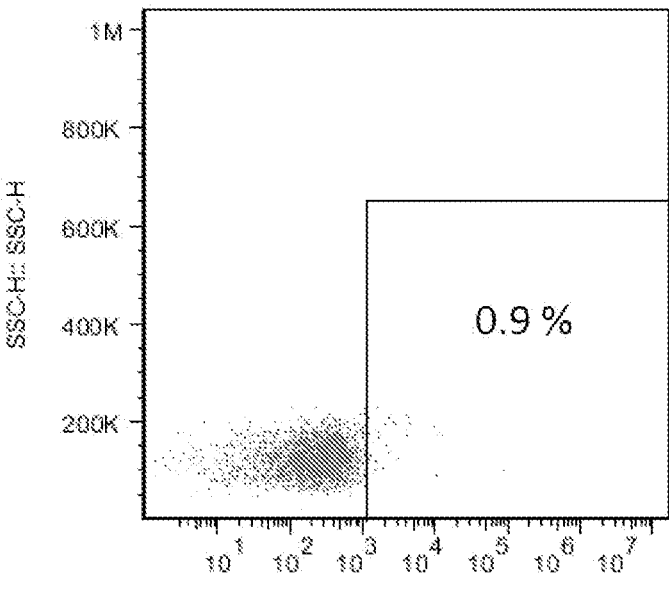
FIG. 1D shows the binding activity of the human-mouse chimeric anti-human Sirpα antibody mab14c of the present disclosure to human T cells.
Figure 2A:
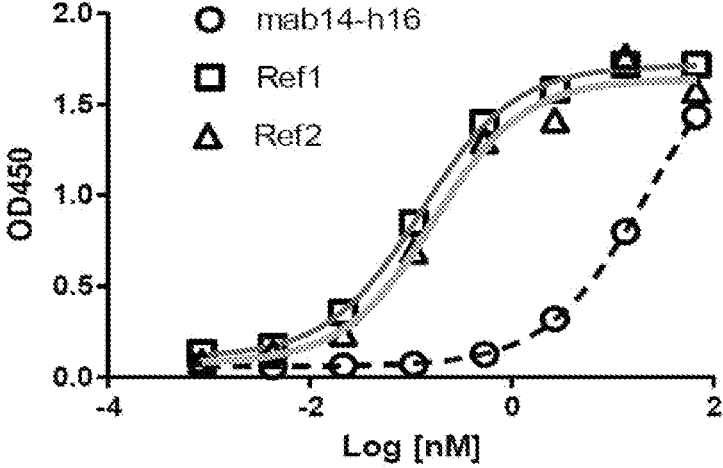
FIG. 2A shows the specific binding activities of the humanized anti-human Sirpα antibody of the present disclosure to human Sirpβ.
Figure 2B:
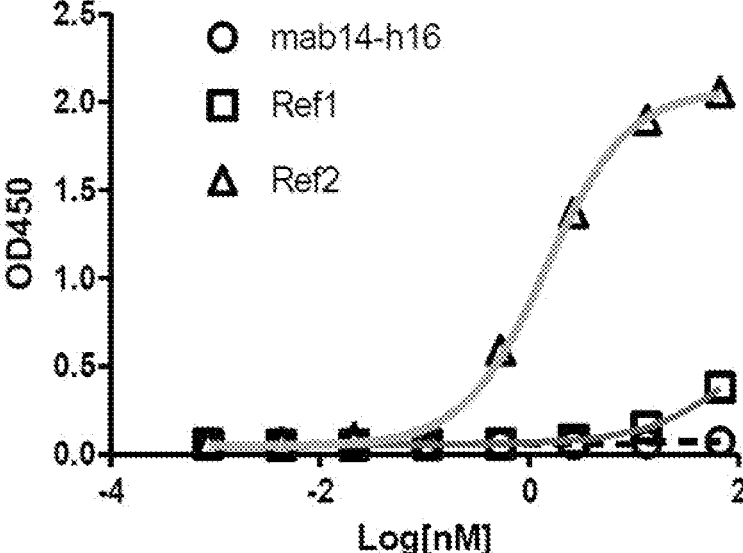
FIG. 2B shows the specific binding activities of the humanized anti-human Sirpα antibody of the present disclosure to human Sirpγ.
Figure 3A:
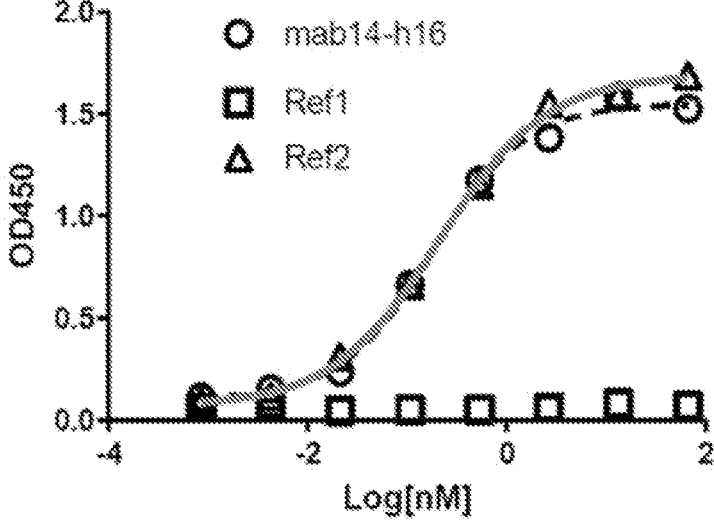
FIG. 3A shows the binding activity of the humanized anti-human Sirpα antibody of the present disclosure to Cyno Sirpα polymorphism 1.
Figure 3B:
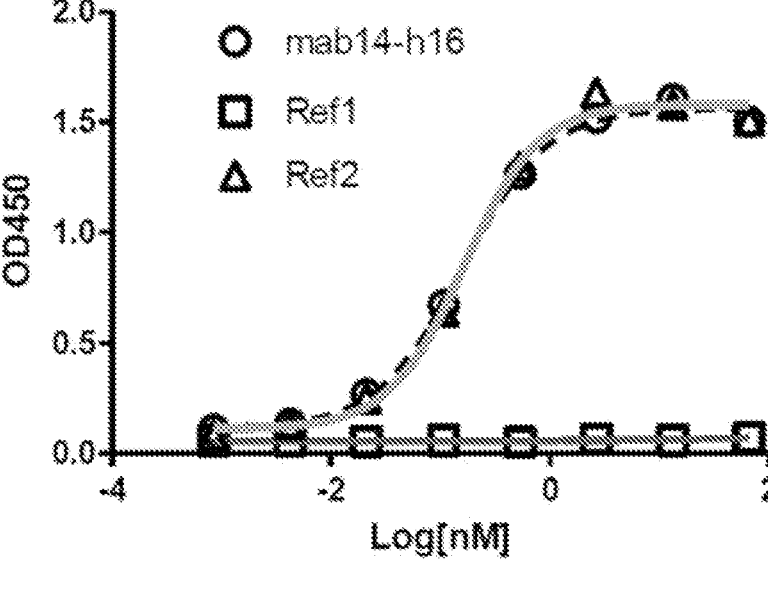
FIG. 3B shows the binding activity of the humanized anti-human Sirpα antibody of the present disclosure to Cyno Sirpα polymorphism 2.
Figure 3C:
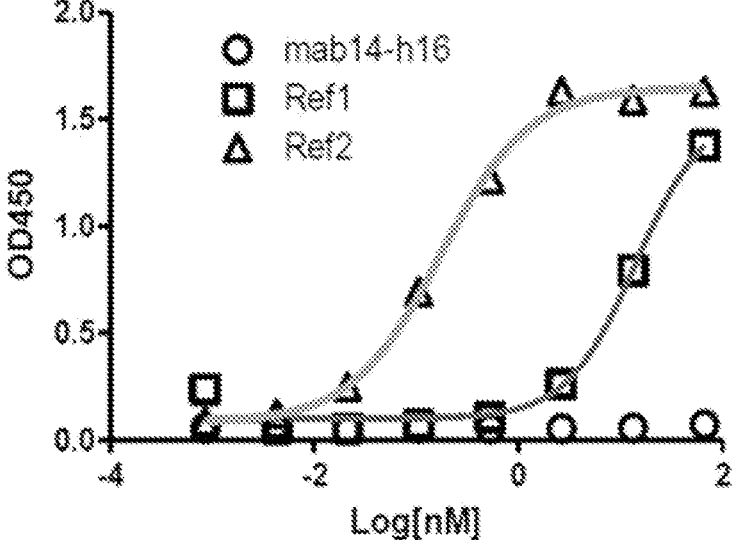
FIG. 3C shows the binding activity of the humanized anti-human Sirpα antibody of the present disclosure to Cyno Sirpα polymorphism 6.

Furthermore, since human T cells expressed Sirpγ, in order to evaluate the binding activity (selectivity) of the antibody of the present disclosure to human T cells, the binding activity of the antibody mab14c of the present disclosure to human T cells was detected by the method of Example 5, and the results were shown in FIG. 1A-FIG. 1D. FIG. 1A was a negative control, that was, only 0.39% of the cells (background level) had fluorescence intensity above 10$^3$ (positive cells) in the absence of the antibody. That was, no bound cells were detected. In the presence of 10 μg/mL of the control antibody 1 (Ref1) (FIG. 1), the proportion of cells with fluorescence intensity above 10$^3$ was 0.49% (background level), that was, the antibody did not bind to T cells. Under the same conditions, the proportion of the detected cells bound to the control antibody 2 (Ref2) was 51.3%, that was, the antibody bound to T cells (FIG. 1C). Under the same conditions, the proportion of cells bound to the antibody of the present disclosure was 0.9% (background level, FIG. 1D), that was, the antibody of the present disclosure did not bind to T cells.

The aforementioned results indicated that the antibody mab14c of the present disclosure was a new antibody which was different from both Ref1 and Ref2. Compared with Ref1, it had better selectivity, could bind to both V1 and V2 forms of Sirpα, and could be targeted at more patient populations (those who expressed V1 and those who expressed V2) clinically. Compared with Ref1, it had better activity of binding to Cyno Sirpα, which brought great convenience for preclinical pharmacological and toxicological research. Furthermore, the antibody of the present disclosure was also different from Ref2 and it had better selectivity than Ref2: it did not bind to Sirpγ or T cells (expressing Sirpγ), could be developed as a drug, and avoided the side effects caused by non-specific targeting brought about by the binding to T cells clinically.

Example 8 Humanization of the Murine Antibody of the Present Disclosure

In order to avoid the risks of immunogenicity and the like aspects in the process of drug development, in the present disclosure, humanization design and screening, and sequence optimization were conducted on the murine antibody mab14. The specific process was described as follows.

Regarding the definition of the CDR of the antibody, there were many different methods in the art. These methods of labeling CDRs could be summarized in the Table 7 below.

TABLE 7

Summary of different methods for defining the CDR of the antibody in the art*

| Loop | Definition of CCG | Definition of Kabat | Definition of AbM | Definition of Chothia | Definition of Contact |
|---|---|---|---|---|---|
| Light chain CDR1 | L24-L34 | L24-L34 | L24-L34 | L24-L34 | L30-L36 |
| Light chain CDR2 | L50-L56 | L50-L56 | L50-L56 | L50-L56 | L45-L55 |
| Light chain CDR3 | L89-L97 | L89-L97 | L89-L97 | L89-L97 | L89-L96 |
| Heavy chain CDR1 | H26-H35 | H31-H35 | H26-H35 | H26-H32 | H30-H35 |
| Heavy chain CDR2 | H50-H65 | H50-H65 | H50-H58 | H52-H56 | H47-H58 |
| Heavy chain CDR3 | H95-H102 | H95-H102 | H95-H102 | H95-H102 | H93-H101 |

*Please refer to the website for more information: http://www.bioinf.org.uk/abs/#cdrdef Laa-Lbb in Table 7 could refer to the amino acid sequence from position aa to position bb starting from the N-terminus of the light chain of the antibody; and Haa-Hbb could refer to the amino acid sequence from position aa to position bb starting from the N-terminus of the heavy chain of the antibody. For example, L24-L34 could refer to the amino acid sequence from position 24 to position 34 starting from the N-terminus of the light chain of the antibody, according to a CCG coding rule; and H26-H32 could refer to the amino acid sequence from position 26 to position 35 starting from the N-terminus of the heavy chain antibody, according to the CCG coding rule. It was well known to those skilled in the art that insertion and/or site deletion sometimes occurred in some positions when coding CDRs.

The aforementioned variable region of the murine anti-human Sirpα antibody mab14 was according to various definition methods in Table 7, and its CDR sequence was labeled/annotated as follows.

TABLE 8

CDR sequences of the anti-hSirpa antibody mab14
of the present disclosure defined according to
the CCG numbering rule

| Antibody | mab14 CDRs |
|---|---|
| Light chain CDR1 | RASQDIRNYLN (SEQ ID NO: 11) |
| Light chain CDR2 | FTSTLHS (SEQ ID NO: 12) |
| Light chain CDR3 | QQGNTLPWT (SEQ ID NO: 13) |
| Heavy chain CDR1 | GYNFNIYWIN (SEQ ID NO: 14) |
| Heavy chain CDR2 | NIYPSSISTNYNEKFKT (SEQ ID NO: 15) |
| Heavy chain CDR3 | SEGTYYGGRYEGDWFGY (SEQ ID NO: 16) |

TABLE 9

The CDR sequences of the anti-hSirpα antibody of
the present disclosure defined according to the
Kabat numbering rule

| Antibody | mab14 CDRs |
|---|---|
| Light chain CDR1 | RASQDIRNYLN (SEQ ID NO: 11) |
| Light chain CDR2 | FTSTLHS (SEQ ID NO: 12) |
| Light chain CDR3 | QQGNTLPWT (SEQ ID NO: 13) |
| Heavy chain CDR1 | IYWIN (SEQ ID NO: 17) |
| Heavy chain CDR2 | NIYPSSISTNYNEKFKT (SEQ ID NO: 15) |
| Heavy chain CDR3 | SEGTYYGGRYEGDWFGY (SEQ ID NO: 16) |

TABLE 10

The CDR sequences of the antibody of the present
disclosure defined according to the AbM
numbering rule

| Antibody | mab14 CDRs |
|---|---|
| Light chain CDR1 | RASQDIRNYLN (SEQ ID NO: 11) |
| Light chain CDR2 | FTSTLHS (SEQ ID NO: 12) |
| Light chain CDR3 | QQGNTLPWT (SEQ ID NO: 13) |
| Heavy chain CDR1 | GYNFNIYWIN (SEQ ID NO: 14) |

TABLE 10-continued

The CDR sequences of the antibody of the present
disclosure defined according to the AbM
numbering rule

| Antibody | mab14 CDRs |
|---|---|
| Heavy chain CDR2 | NIYPSSIST (SEQ ID NO: 18) |
| Heavy chain CDR3 | SEGTYYGGRYEGDWFGY (SEQ ID NO: 16) |

TABLE 11

The CDR sequences of the antibody of the present
disclosure defined according the Chothia
numbering rule

| Antibody | mab14 CDRs |
|---|---|
| Light chain CDR1 | RASQDIRNYLN (SEQ ID NO: 11) |
| Light chain CDR2 | FTSTLHS (SEQ ID NO: 12) |
| Light chain CDR3 | QQGNTLPWT (SEQ ID NO: 13) |
| Heavy chain CDR1 | GYNFNIY (SEQ ID NO: 19) |
| Heavy chain CDR2 | YPSSI (SEQ ID NO: 20) |
| Heavy chain CDR3 | SEGTYYGGRYEGDWFGY (SEQ ID NO: 16) |

TABLE 12

The CDR sequences of the antibody of the present
disclosure defined according to the Contact
numbering rule

| Antibody | mab14 CDRs |
|---|---|
| Light chain CDR1 | RNYLNWY (SEQ ID NO: 21) |
| Light chain CDR2 | KLLIYFTSTLH (SEQ ID NO: 22) |
| Light chain CDR3 | QQGNTLPW (SEQ ID NO: 23) |
| Heavy chain CDR1 | NIYWIN (SEQ ID NO: 24) |
| Heavy chain CDR2 | WIGNIYPSSIST (SEQ ID NO: 25) |
| Heavy chain CDR3 | ARSEGTYYGGRYEGDWFG (SEQ ID NO: 26) |

After the aforementioned analysis, labeling and definition of the CDR sequence of the murine antibody mab14 of the present disclosure, it was humanized according to the methods published in many literatures in the art. The murine antibody sequence was compared with a human antibody germline database (v-base) to find out the light and heavy chain germlines of the human antibody with high homology. On this basis, computer modeling was carried out to simulate the sites in the antibody structure that might affect the binding to the antigen, key sites of back mutation and a combination thereof, so as to screen out a humanized antibody molecule with the preferred activity.

Specifically, through the comparative analysis of sequence homology, it was found that the human antibody germline with better homology with the light chain of mab14 included IGKV1-27*01, IGKV1-33*01, IGKV1-39*01, IGKV1-NL1*01, IGKV1/OR10-1*01, IGKV1D-33*01, IGKV1D-39*01, IGKV1-12*01, IGKV1-12*02, IGKV1-17*02, etc. After further comparison and analysis, the human antibody germline light chain IGKV1-39*01 was preferred. It had been found through sequence alignment that the J gene region of the light chain of mab14 had high homology with human antibody germlines hJk1, hJk2.1, hJk2.2, hJk2.3, hJk2.4, hJk3, hJk4.1, hJk4.2, and hJk5. After further comparison and analysis, hJh4.1 was preferred for the humanized human antibody germline J region of the light chain of mab14, and subjected to humanized design, screening and sequence optimization.

Through the comparative analysis of sequence homology, it was found that the human antibody germline with better homology to the heavy chain of mab14 included IGHV1-46*01, IGHV1-46*02, IGHV1-46*03, IGHV1-69*02, IGHV1-69*04, IGHV1-69*06, IGHV1-69*08, IGHV1-69*09, IGHV1-69*10, IGHV1-69*14, etc. After further comparison and analysis, the sequence of the human germline heavy chain IGHV1-46*01 was preferred for humanization of the antibody of the present disclosure. It had been found through sequence alignment that the J gene region of the heavy chain of mab14 had high homology with the human antibody germline heavy chain J genes hJh1, hJh2, hJh3.1, hJh3.2, hJh4.1, hJh4.2, hJh4.3, hJh5.1, hJh5.2, hJh6.1, hJh6.2, hJh6.3 etc. After further comparison and analysis, hJh4.1 was preferred for the humanized human antibody germline J region of the heavy chain of mab14, and subjected to humanized design, screening and sequence optimization.

The antibody of the present disclosure was transplanted with the CDR of mab14 (see the definition of CDR above, which was mainly defined by CCG in this example) to the selected humanized light and heavy chain human antibody germline template, and then recombined with IgG light and heavy chain constant regions. Then, based on the three-dimensional structure of the murine antibody, the embedded residues, residues that directly interacted with CDR, and residues that had important influence on the conformations of VL and VH are subjected to back mutation, and these mutations and mutation combinations were screened to see the influence on the antibody activity, and the chemically unstable amino acid residues of the CDR were optimized to obtain an antibody molecular sequence with optimization in structure, activity and the like. That was, the humanization of the murine antibody of the present disclosure was completed.

Combined with the specific sequence of mab14, the hIgG4 heavy chain and the κ type light chain (with the sequences as shown below) were taken as examples for explanation hereafter.

Light chain constant region κ chain of human antibody:

(SEQ ID NO: 27)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

-continued

Heavy chain constant region of human IgG4:

(SEQ ID NO: 28)
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

The preferred sequence of the humanized light chain variable region of the present disclosure was as follows:

>mab14-hL1

(SEQ ID NO: 29)
DIQMTQSPSSLSASVGDRVTITCRASQDIRNYLNWYQQKPGKAPKLLIY
FTSTLHSGVPSRFSGSGSGTDFTLTISSLQPEDFATYYCQQGNTLPWTF
GGGTKVEIK

>mab14-hL2

(SEQ ID NO: 30)
DIQMTQSPSSLSASVGDRVTITCRASQDIRNYLNWYQQKPGGTVKLLIY
FTSTLHSGVPSRFSGSGSGTDYTLTISSLQPEDFATYYCQQGNTLPWTF
GGGTKVEIK

>mab14-hL3

(SEQ ID NO: 31)
DIQMTQSPSSLSASVGDRVTITCRASQDIRNYLNWYQQKPGGTPKLLIY
FTSTLHSGVPSRFSGSGSGTDFTLTISSLQPEDFATYYCQQGNTLPWTF
GGGTKVEIK

>mab14-hL4

(SEQ ID NO: 32)
DIQMTQSPSSLSASVGDRVTITCRASQDIRNYLNWYQQKPGGAPKLLIY
FTSTLHSGVPSRFSGSGSGTDYTLTISSLQPEDFATYYCQQGNTLPWTF
GGGTKVEIK

>mab14-hL5

(SEQ ID NO: 33)
DIQMTQSPSSLSASVGDRVTITCRASQDIRNYLNWYQQKPGGTPKLLIY
FTSTLHSGVPSRFSGSGSGTDYTLTISSLQPEDFATYYCQQGNTLPWTF
GGGTKVEIK

>mab14-hL6

(SEQ ID NO: 34)
DIQMTQSPSSLSASVGDRVTITCRASQDIRNYLNWYQQKPGKTPKLLIY
FTSTLHSGVPSRFSGSGSGTDYTLTISSLQPEDFATYYCQQGNTLPWTF
GGGTKVEIK

The preferred sequence of the humanized heavy chain variable region of the present disclosure:

mab14-hH1

(SEQ ID NO: 35)
QVQLVQSGAEVKKPGASVKVSCKASGYNFNIYWINWVRQAPGQGLEWMG
NIYPSSISTNYNEKFKTRVTMTRDTSTSTVYMELSSLRSEDTAVYYCAR
SEGTYYGGRYEGDWFGYWGQGTLVTVSS mab14-hH2

(SEQ ID NO: 36)
QVQLVQSGAEVKKPGASVKVSCKASGYNFNIYWINWVKQAPGQGLEWIG
NIYPSSISTNYNEKFKTKATLTVDKSTSTVYMEFSSLRSEDTAVYYCAR
SEGTYYGGRYEGDWFGYWGQGTLVTVSS mab14-hH3

(SEQ ID NO: 37)
QVQLVQSGAEVKKPGASVKVSCKASGYNFNIYWINWVRQAPGQGLEWMG
NIYPSSISTNYNEKFKTRATLTVDTSTSTVYMELSSLRSEDTAVYYCAR
SEGTYYGGRYEGDWFGYWGQGTLVTVSS

-continued

```
mab14-hH4
                                   (SEQ ID NO: 38)
QVQLVQSGAEVKKPGASVKVSCKASGYNFNIYWINWVRQAPGQGLEWIG
NIYPSSISTNYNEKFKTRATLTVDTSTSTVYMELSSLRSEDTAVYYCAR
SEGTYYGGRYEGDWFGYWGQGTLVTVSS mab14-hH5
                                   (SEQ ID NO: 39)
QVQLVQSGAEVKKPGASVKVSCKASGYNFNIYWINWVRQAPGQGLEWIG
NIYPSSISTNYNEKFKTRATLTVDKSTSTVYMELSSLRSEDTAVYYCAR
SEGTYYGGRYEGDWFGYWGQGTLVTVSS mab14-hH6
                                   (SEQ ID NO: 40)
QVQLVQSGAEVKKPGASVKVSCKASGYNFNIYWINWVKQAPGQGLEWIG
NIYPSSISTNYNEKFKTRATLTVDTSTSTVYMELSSLRSEDTAVYYCAR
SEGTYYGGRYEGDWFGYWGQGTLVTVSS mab14-hH7
                                   (SEQ ID NO: 41)
QVQLVQSGAEVKKPGASVKVSCKASGYNFNIYWINWVKQAPGQGLEWIG
NIYPSSISTNYNEKFKTKATLTVDTSTSTVYMELSSLRSEDTAVYYCAR
SEGTYYGGRYEGDWFGYWGQGTLVTVSS
```

The humanized sequence of the light chain of the murine antibody of the present disclosure contained different back mutations, and the number of the back mutation sites could be 10 or more, and preferably 0-10, as for the sequences listed above. These arbitrary sequences were combined with the constant region sequences of the light chain constant region κ or λ chain of the human antibody to obtain the light chain sequence of the antibody of the present disclosure, such as the κ type light chain constant region for the light chain of the present disclosure, as for the sequences listed above. Likewise, the heavy chain variable regions used for humanization also had different numbers of back mutations, and the number of back mutation sites could be 10 or more, and preferably 0-10, as for the heavy chain variable region sequences listed above. These heavy chain variable region sequences containing different numbers of back mutations were recombined with optionally the constant region sequences of human IgG1, human IgG2, human IgG3, and human IgG4 chains to obtain the heavy chain sequences of the present disclosure. For example, the heavy chain of the present disclosure was illustrated by taking hIgG4 which was used as a constant region sequence as an example.

The present disclosure partially optimized the humanized antibody sequence, and the results of the expression level and activity evaluation of the expressed antibody (by the ELISA detection method of Example 3 of the present disclosure) were as follows.

TABLE 13

Humanized antibody sequences of the present disclosure (human κ type light chain, taking the hIgG4 heavy chain constant region as an example)

| | Light chain | | Heavy chain | | | Activity of |
|---|---|---|---|---|---|---|
| Chimeric and Humanized Antibodies | Variable region | Constant region (κ chain) | Variable region | Constant region (hIgG4) | Expression level (mg/L) | binding to hSirpα-V1, ELISA, nM |
| mab14c | SEQ ID NO: 9 | SEQ ID NO: 27 | SEQ ID NO: 10 | SEQ ID NO: 28 | 49.3 | 0.093 |
| mab14-h1 | SEQ ID NO: 29 | | SEQ ID NO: 35 | | 227.9 | 0.148 |
| mab14-h2 | SEQ ID NO: 30 | | SEQ ID NO: 36 | | 195.5 | 0.073 |
| mab14-h3 | SEQ ID NO: 30 | | SEQ ID NO: 37 | | 206.6 | 0.103 |
| mab14-h4 | SEQ ID NO: 30 | | SEQ ID NO: 38 | | 224.3 | 0.088 |
| mab14-h5 | SEQ ID NO: 30 | | SEQ ID NO: 39 | | 217.8 | 0.061 |
| mab14-h6 | SEQ ID NO: 30 | | SEQ ID NO: 40 | | 191.8 | 0.095 |
| mab14-h7 | SEQ ID NO: 30 | | SEQ ID NO: 41 | | 143.9 | 0.081 |
| mab14-h8 | SEQ ID NO: 31 | | SEQ ID NO: 36 | | 190.8 | 0.067 |
| mab14-h9 | SEQ ID NO: 32 | | SEQ ID NO: 36 | | 164.9 | 0.062 |
| mab14-h10 | SEQ ID NO: 33 | | SEQ ID NO: 36 | | 199.5 | 0.068 |
| mab14-h11 | SEQ ID NO: 34 | | SEQ ID NO: 36 | | 219.2 | 0.073 |
| mab14-h12 | SEQ ID NO: 31 | | SEQ ID NO: 39 | | 105.34 | 0.092 |
| mab14-h13 | SEQ ID NO: 32 | | SEQ ID NO: 39 | | 103.8 | 0.089 |
| mab14-h14 | SEQ ID NO: 33 | | SEQ ID NO: 39 | | 103.6 | 0.057 |
| mab14-h15 | SEQ ID NO: 34 | | SEQ ID NO: 39 | | 76.29 | 0.077 |
| mab14-h16 | SEQ ID NO: 29 | | SEQ ID NO: 39 | | 275 | 0.087 |
| Ref1 | SEQ ID NO: 55 of WO20171 78653A2 | | SEQ ID NO: 42 of WO201717 8653A2 | | 44.9 | 0.072 |

The aforementioned results showed that the binding activity of the human-murine chimeric antibody mab14c of the present disclosure to hSirpα-v1 was almost the same as that of the control molecule Ref1 (0.093 VS 0.072). The aforementioned humanized antibody molecules obtained by 3 rounds of different combinations of the light and heavy chain sequences at different humanized degrees of the human-murine chimeric antibody sequence mab14c of the present disclosure all retained the binding activity that was almost consistent with that of the chimeric antibody.

More preferably, there were significant differences in the expression levels of different combined antibodies between sequences with different degrees of humanization, wherein the expression levels of mab14-h1, mab14-h11, mab14-h16 and the like antibodies were up to 200 mg/L, wherein the expression level of mab14-h16 was the highest, at 275 mg/L, which was 4.5 times higher than that of the chimeric antibody mab14c (275 mg/L VS 9 mg/L).

More specifically, the effects of the humanized antibody of the present disclosure in blocking the binding of hSirpα (dimer) to hCD47 and blocking the binding of hSirpα to hCD47 (dimer) were detected by the experimental method of Example 4. The results were shown in Table 14, and the humanized antibody of the present inventor retained the characteristic of the chimeric antibody mab14c of blocking the binding of hSirpα to hCD47 well. This result showed that the chimeric antibody and humanized antibody of the present disclosure not only bound to the hSirpα protein, but also effectively blocked the binding of hSirpα to hCD47.

TABLE 14

Activity of humanized antibody of the present disclosure (human κ type light chain, taking the hIgG4 heavy chain constant region as an example)

| Humanized antibody | Blocking binding of h Sirpa (dimer) to hCD47 (ELISA), $IC_{50}$, nM | Blocking binding of hSirpα to hCD47 (dimer) (ELISA), $IC_{50}$, nM |
| --- | --- | --- |
| mab14c | 5.48 | 9.98 |
| mab14-h5 | 8.99 | 8.47 |
| mab14-h12 | 3.49 | 8.08 |
| mab14-h13 | 5.31 | 9.56 |
| mab14-h14 | 4.75 | 9.1 |
| mab14-h15 | 5.13 | 7.37 |
| mab14-h16 | 5.92 | 10.14 |

The light and heavy chain amino acid (including constant regions) sequences of the humanized antibody (some representative molecules) were listed as follows.

The amino acid sequence of the humanized mab14-h5 antibody:

```
Light chain:
                              (SEQ ID NO: 42)
DIQMTQSPSSLSASVGDRVTITCRASQDIRNYLNWYQQKPGGTVKLLIY

FTSTLHSGVPSRFSGSGSGTDYTLTISSLQPEDFATYYCQQGNTLPWTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

-continued

```
Heavy chain:
                              (SEQ ID NO: 43)
QVQLVQSGAEVKKPGASVKVSCKASGYNFNIYWINWVRQAPGQGLEWIG

NIYPSSISTNYNEKFKTRATLTVDKSTSTVYMELSSLRSEDTAVYYCAR

SEGTYYGGRYEGDWFGYWGQGTLVTVSSASTKGPSVFPLAPCSRSTSES

TAALGCLVKDYFPEPVTVSWNSGALTSGVHTFPAVLQSSGLYSLSSVVT

VPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNH

YTQKSLSLSLGK
```

The amino acid sequence of the humanized mab14-h12 antibody:

```
Light chain:
                              (SEQ ID NO: 44)
DIQMTQSPSSLSASVGDRVTITCRASQDIRNYLNWYQQKPGGTPKLLIY

FTSTLHSGVPSRFSGSGSGTDFTLTISSLQPEDFATYYCQQGNTLPWTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

The heavy chain sequence of the humanized antibody mab14-h12 was the same as SEQ ID NO: 43.

The amino acid sequence of the humanized mab14-h13 antibody:

```
                              (SEQ ID NO: 45)
DIQMTQSPSSLSASVGDRVTITCRASQDIRNYLNWYQQKPGGAPKLLIY

FTSTLHSGVPSRFSGSGSGTDYTLTISSLQPEDFATYYCQQGNTLPWTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

The heavy chain sequence of the humanized antibody mab14-h13 was the same as SEQ ID NO: 43.

The amino acid sequence of the humanized mab14-h14 antibody

```
Light chain:
                              (SEQ ID NO: 46)
DIQMTQSPSSLSASVGDRVTITCRASQDIRNYLNWYQQKPGGTPKLLIY

FTSTLHSGVPSRFSGSGSGTDYTLTISSLQPEDFATYYCQQGNTLPWTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

The heavy chain sequence of the humanized antibody mab14-h14 was the same as SEQ ID NO: 43.

The amino acid sequence of the humanized mab14-h15 antibody:

49 50

Light chain:
(SEQ ID NO: 47)
DIQMTQSPSSLSASVGDRVTITCRASQDIRNYLNWYQQKPGKTPKLLIY

FTSTLHSGVPSRFSGSGSGTDYTLTISSLQPEDFATYYCQQGNTLPWTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

The heavy chain sequence of the humanized antibody mab14-h15 was the same as SEQ ID NO: 43.

The amino acid sequence of the humanized mab14-h16 antibody:

(SEQ ID NO: 48)
DIQMTQSPSSLSASVGDRVTITCRASQDIRNYLNWYQQKPGKAPKLLIY

FTSTLHSGVPSRFSGSGSGTDFTLTISSLQPEDFATYYCQQGNTLPWTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

The heavy chain sequence of the humanized antibody mab4-h16 was the same as SEQ ID NO: 43.

Example 9 Comprehensive Evaluation of Binding Activity of Humanized Anti-Human Sirpα Antibody and Preferred Antibody of the Present Disclosure In order to further evaluate the binding activity of the humanized antibody of the present disclosure, taking the preferred humanized antibody mab14-h16 of the present disclosure as an example, it was subjected to evaluation of parallel/repeated binding activity (ELISA) compared with the reference antibody Ref. The binding activities of the antibody to hSirpα-V1, hSirpα-V2, hSirpβ, hSirpγ and different polymorphic Cyno Sirpαs were detected. The experimental method was the same as that of Example 3, and the results were shown in Table 15 below and FIGS. 2A, 2B, 3A, 3B and 3C.

TABLE 15

Comprehensive evaluation of the binding activity of the antibody of the present disclosure to Sirpα (EC$_{50}$, nM)

| Antigen | mab14-h16 | Ref1 | Ref2 |
|---|---|---|---|
| hSirpα-V1 | 0.065 | 0.057 | 0.159 |
| hSirpα-V2 | 0.094 | ND | 0.37 |
| hSirpβ | faint binding | 0.126 | 0.167 |
| hSirpγ | ND | ND | 1.46 |
| NOD mouse mu-Sirpα | ND | ND | Weak binding (2.82) |
| Cyno Sirpα polymorphism 1 (L932) | 0.181 | ND | 0.209 |
| Cyno Sirpα polymorphism 2 (L933) | 0.159 | ND | 0.164 |
| Cyno Sirpα polymorphism 3 (L936) | 0.143 | ND | 0.198 |
| Cyno Sirpα polymorphism 4 (L937) | 0.121 | faint binding | 0.186 |

TABLE 15-continued

Comprehensive evaluation of the binding activity of the antibody of the present disclosure to Sirpα (EC$_{50}$, nM)

| Antigen | mab14-h16 | Ref1 | Ref2 |
|---|---|---|---|
| Cyno Sirpα polymorphism 5 (L938) | ND | faint binding | 0.175 |
| Cyno Sirpα polymorphism 6 (L939) | ND | faint binding | 0.167 |

The aforementioned results showed that, in the present disclosure it was unexpectedly found that the murine anti-human Sirpα antibody and humanized anti-human Sirpα antibody were very specific and novel antibodies. Unlike Ref1, this antibody could bind to human Sirpα-V1, V2 and various Cyno Sirpαs (polymorphism) simultaneously, but not to Sirpβ.

Not only that, the novel antibody of the present disclosure was also significantly different from Ref2. Ref2 could also bind to both Sirpα-V1 and V2, but the binding activity of it was weaker than that of the antibody of the present disclosure. The binding activity of the antibody mab14-h16 of the present disclosure to Sirpα-V1 was 1.4 times stronger than that of Ref2 (0.065 nM vs 0.159 nM in the above table), and the binding activity of it to Sirpα-V2 was 2.9 times stronger than that of Ref2 (0.094 nM vs 0.37 nM). A more significant difference was that Ref2 had relatively stronger binding to both Sirpβ and Sirpγ, with EC$_{50}$ of 0.167 nM and 1.46 nM, respectively. The antibody of the present disclosure bound only faintly or not at all to Sirpβ and Sirpγ. The unique selectivity of the present disclosure (specifically binding to Sirpα, but not to Sirpβ and Sirpγ) given it an outstanding advantage in the process of clinical drug development, that was, it could avoid the safety problem brought about by off-target.

Moreover, Ref2 could bind to Cyno Sirpα polymorphisms 5 and 6. This was also different from the antibody of the present disclosure.

These characteristics indicated that the binding sites (epitopes) of the antibody of the present disclosure were different from those of Ref1 and Ref2.

In order to further evaluate the cell-binding activity of the antibody of the present disclosure and the activity of the same in blocking the binding of Sirpα to a corresponding ligand CD47, in the present disclosure, taking the preferred humanized antibody mab14-h16 as an example, the binding activity of it to cell strains with high expression of human Sirpα was detected by ELISA of a plated coated by the cell strains with high expression of human Sirpα+, and the detection method was as shown in Example 2. The ability of the humanized antibody of the present disclosure to block the binding of human Sirpα to CD47 was detected by the method of Example 4, and the binding of the humanized antibody to human T cells was detected by the method of Example 5. The results were shown in Table 16a.

Moreover, the binding of human Sirpα-V2 to human CD47 as blocked by the antibody of the present disclosure was further detected. Specifically, the recombinant protein of human Sirpα-V2-his was diluted to a concentration of 2 μg/mL with a PBS buffer at pH7.4, then added into a 96-well ELISA plate (Corning®, CLS3590-100EA) at a volume of 50 μL/well, and placed in an incubator at 37° C. for 2 hours. After the liquid was discarded, the wells were added with a blocking solution of 5% skimmed milk (skimmed milk powder available from Bright Dairy) diluted with PBS at 230 μL/well, and incubated in an incubator at 37° C. for 3 hours, or placed overnight at 4° C. (for 16-18 hours) for blocking. The blocking solution was discarded, and the plate was washed with a PBST buffer (pH7.4 PBS containing 0.05% tween-20) for 5 times, then added with 25 μL/well of the 3-fold gradient dilution of the antibody to be tested at a starting concentration of 100 μg/mL and 25 μL/well of Biotin labeled CD47-hFc or CD47-his at a concentration of 4 μg/mL, mixed uniformly, and then incubated in an incubator at 37° C. for 1 hour. The plate was washed for 5 times, added with 50 μL/well of a streptavidin-TRP secondary antibody (GenScript, M00091) diluted at 1:1000, incubated at 37° C. for 1 hour, and then washed with PBST for 5 times. Each well was added with 50 μL TMB (Surmodic, Cat #TTMB-1000-01) for color development, and added with 50 μL/well of 1 M $H_2SO_4$ to stop the reaction. The readings on a microplate reader (MultiskanGO Thermo, Model: 51119200) were subjected to data analysis by GraphPad prism 5. The results were shown in Table 16b.

TABLE 16a

Evaluation of cell binding and blocking activities of the antibody of the present disclosure

| Antibody sample | mab14-h16 | Ref1 | Ref2 |
| --- | --- | --- | --- |
| T-cell binding activity (% binding) | 1.95 | 1.79 | 47.6 |
| hSirpα-v1+ cell strain binding activity ($EC_{50}$, nM) | 0.124 | 0.084 | 0.106 |
| Blocking the binding of hSirpα (dimer) to CD47 ($IC_{50}$, nM) | 4.81 | 3.74 | 4.79 |
| Blocking the binding of hSirpα to CD47 (dimer), $IC_{50}$ (nM) | 5.28 | 4.16 | 5.44 |

TABLE 16b

Evaluation of the activity of the antibody of the present disclosure in blocking the binding of human Sirpα-V2 to human CD47

| Antibody sample | mab14-h16 | Ref1 | Ref2 |
| --- | --- | --- | --- |
| Blocking the binding of hSirpα-V2 to hCD47 ($IC_{50}$, nM) | 2.39 | ND | 1.29 |
| Blocking the binding of hSirpα-V2 to human CD47 (dimer), $IC_{50}$ (nM) | 6.29 | ND | 3.09 |

ND: the blocking signal was not detected.

The results in the aforementioned table showed that the humanized antibody and preferred antibody mab14-h16 of the present disclosure did not bind to human T cells (the binding percentage of the negative control in this test was 1.67%, which was close to the binding ratio 1.95% of mab14-h16, i.e., the background level). Its activities of binding to a hSirpα-v1+ cell strain and blocking the binding of hSirpα-v1 to human CD47 were close to those of the controls Ref1 and Ref2, and it could effectively block the binding of hSirpα-V2 to human CD47.

The data of the aforementioned examples showed that, in the present disclosure, it was unexpectedly found that the murine anti-human Sirpα antibody and humanized anti-human Sirpα antibody can bind to human Sirpα-V1 and Sirpα-V2 simultaneously, and have stronger activities of binding to human Sirpα-V1 and human Sirpα-V2 and binding to various Cyno Sirpα (polymorphism), and did not bind to human Sirpβ and Sirpγ as well as human T cells.

Moreover, the antibody of the present disclosure had a very good activity of blocking the binding of human Sirpα (including Sirpα-V1 and Sirpα-V2) to human CD47, so that the antibody can be developed as a new drug targeting the binding of Sirpα to CD47, so as to achieve the purpose of treating a tumor.

These outstanding characteristics enabled the antibody of the present disclosure to show unique clinical advantages, which was presented as that the antibody could target more patient populations (the population expressing V1 and the population expressing V2). The antibody did not bind to Sirpβ, Sirpγ and T cells, and had very good specificity, thereby avoiding the side effects caused by clinical off-target. Meanwhile, the antibody of the present disclosure could bind to a variety of Cyno Sirpαs very strongly, and the primate cyno could be selected in the preclinical safety evaluation research, which provided convenience for the preclinical research.

Example 10 Humanized Anti-Human Sirpα Antibody PTM of the Present Disclosure

By means of MOE (molecular operating environment); Schrodinger; or DS (Discovery Studio) and the like computer analysis software, the antibody of the present disclosure was subjected to Post-translational Modification (PTM) site analysis. As a result, it was found that among M4, C23, W35, C88, and W96 of the light chain and C22, W33, W36, W47, M81, C96, and W112 of the heavy chain (H Chain) of the preferred antibody of the present disclosure, only M4 was a low-risk oxidation site, while the others were non-oxidation hot spots. There was no other deamination site or hot spot in the whole sequence, except a slight risk of deamination in the N92 of the light chain. There was no N-glycosylation hot spot and no Asp isomerization site or hot spot in the whole sequence. The humanized sequence of the present disclosure was therefore the preferred sequence for PTM analysis.

Example 11 Design of Bispecific Antibody Against Sirpα Target

Based on the anti-Sirpα antibody found above, the design of various bispecific antibodies had carried out in the present disclosure. The general formula of the designed bispecific antibody was as follows.

TABLE 17

Bispecific design based on the anti-Sirpα antibody of the present disclosure (general formula 1)

| Protocol | Light chain-containing sequence | Heavy chain-containing sequence |
| --- | --- | --- |
| 1 | T2 $(scFv)_{n1}$-T1VL-LC-T2 $(scFv)_{n2}$ | T2 $(scFv)_{n3}$-T1VH-HC-T2 $(scFv)_{n4}$ |
| 2 | T1 $(scFv)_{n1}$-T2VL-LC-T1 $(scFv)_{n2}$ | T1 $(scFv)_{n3}$-T2VH-HC-T1 $(scFv)_{n4}$ |
| 3 | T2 $(scFv)_{n1}$-T1VL-LC-T1 $(scFv)_{n2}$ | T2 $(scFv)_{n3}$-T1VH-HC-T1 $(scFv)_{n4}$ |
| 4 | T1 $(scFv)_{n1}$-T2VL-LC-T2 $(scFv)_{n2}$ | T1 $(scFv)_{n3}$-T2VH-HC-T2 $(scFv)_{n4}$ |

In Table 17, a light chain-containing sequence means that the sequence may include, in addition to the light chain sequence, a scFv linked to the light chain sequence; and a heavy chain-containing sequence means that the sequence may include, in addition to the heavy chain sequence, a scFv linked to the heavy chain sequence. T1 represents the first protein functional region against the target 1 (e.g., Sirpα), and T2 represents the second protein functional region against the target 2 (not Sirpα). T1 (scFv) represents the scFv sequence of the antibody against target 1; and T2 (scFv) represents the scFv sequence against target 2.

n1, n2, n3 and n4 in $(scFv)_{n1}$, $(scFv)_{n2}$, $(scFv)_{n3}$ and $(scFv)_{n4}$ are respectively natural numbers, which can be 0, 1, 2, 3, etc. In a specific embodiment of the present disclosure, the value of at least one of the n1, n2, n3 and n4 is 1, and the rest are 0. VL represents the light chain variable region sequence of the antibody against the target 1 or 2; and VH represents the heavy chain variable region sequence of the antibody against the target 1 or 2. LC represents the constant region sequence of the light chain (κ or λ), preferably the human light chain constant region sequence; and HC represents the constant region sequence of the heavy chain including IgG1, IgG2, IgG3, IgG4, etc. (abbreviated as HC-IgG1, HC-IgG2, HC-IgG3, and HC-IgG4), preferably human heavy chain constant region sequence (HC-hIgG). When scFv or other protein sequences are linked to the C-terminus of the heavy chain constant region, the last amino acid K at the C-terminus of the heavy chain constant region can be mutated, preferably mutated to A. Therefore, in scheme 1, T1 is immunoglobulin, and T2 is scFv; in scheme 2, T2 is immunoglobulin, and T1 is scFv; the targets of the scFvs are the same; and in schemes 3 and 4, the scFvs at two ends target two different targets.

In Table 17, the scFv is a light chain variable region-linker-heavy chain variable region, and the N-terminus of the light chain variable region or the C-terminus of the heavy chain variable region is accordingly linked to the C-terminus or N-terminus of the light and/or heavy chain of the immunoglobulin through the linker; or the scFv is heavy chain variable region-linker-light chain variable region, and the N-terminus of the heavy chain variable region or the C-terminus of the light chain variable region is accordingly linked to the C-terminus or N-terminus of the light and/or heavy chain of the immunoglobulin through the linker.

It should be noted that when the aforementioned scFv is light chain variable region-linker-heavy chain variable region, the linking mode of it is that the C-terminus of the light chain variable region is linked with the linker, and the linker is then linked with the N-terminus of the heavy chain variable region, thereby exposing the N-terminus of the light chain variable region and the C-terminus of the heavy chain variable region in the scFv, so that it can be linked to the light and/or heavy chain of the immunoglobulin through a linker. In the present disclosure, when it is linked to the light chain of the immunoglobulin, in some specific embodiments, preferably the C-terminus of the heavy chain variable region of the scFv is linked to the N-terminus of the heavy chain of the immunoglobulin through a linker; and when it is linked to the heavy chain of the immunoglobulin, in some specific embodiments, preferably the N-terminus of the light chain variable region of the scFv is linked to the C-terminus of the heavy chain of the immunoglobulin.

When the scFv is heavy chain variable region-linker-light chain variable region, the linking mode of it is that the N-terminus of the light chain variable region is linked with the linker, and the linker is then linked with the C-terminus of the heavy chain variable region, thereby exposing the C-terminus of the light chain variable region and the N-terminus of the heavy chain variable region in the scFv, so that it can be linked to the light and/or heavy chain of the immunoglobulin through a linker. In this case, when it is linked to the light chain of the immunoglobulin, in some specific embodiments, preferably the C-terminus of the light chain variable region of the scFv is linked to the N-terminus of the heavy chain of the immunoglobulin; and when it is linked to the heavy chain of the immunoglobulin, in some specific embodiments, preferably the N-terminus of the heavy chain variable region of the scFv is linked to the C-terminus of the heavy chain of the immunoglobulin.

The linker was preferably $(G_4S)_m$, and the m was preferably an integer between 0-10. Further preferably, the linker was (Gly-Gly-Gly-Gly-Ser)$_3$ (SEQ ID NO: 60), and/or the number of the scFvs was a pair of scFvs which were symmetrically linked to the C-terminus and/or N-terminus of the light and/or heavy chain of the immunoglobulin.

For the sequences against various targets involved in the aforementioned bispecific design, in addition to the anti-Sirpα antibody sequence of the present disclosure, other antibody sequences against the targets are derived from published antibody sequences. It included anti-PD-1 antibodies Nivolumab/Opidivo® (referred to as Nivo for short) and Pembrolizumab/Keytruda® (referred to as Pem for short).

Example 12 Antigen-Antibody Binding (ELISA) Assay

The self-expressed human PD-1, Sirpα and the like antigens of the present disclosure were diluted with a PBS buffer at pH7.4 to a concentration of 2 μg/mL according to different assays, and then added into a 96-well ELISA plate (Corning®, CLS3590-100EA) at a volume of 50 μL/well, and placed in an incubator at 37° C. for 2 hours. After the liquid was discarded, the wells were added with a blocking solution of 5% skimmed milk (Sangon Biotech (Shanghai) Co., Ltd., A600669-0250) diluted with PBS at 200 μL/well, and incubated in an incubator at 37° C. for 3 hours, or placed overnight at 4° C. (for 16-18 hours) for blocking. The blocking solution was discarded, and the plate was washed with a PBST buffer (pH7.4 PBS containing 0.05% tween-20) for 5 times, then added with 50 μL/well of 5-fold serial dilution of the antibody to be tested in 1% BSA, and incubated at 37° C. for 1 hour. The plated was washed with PBST for 5 times, added with 50 μL/well of a HRP-labeled secondary antibody (Jackson Immuno Research, 115-035-003) diluted at 1:2500, and incubated at 37° C. for 1 hour. The plated was washed with PBST for 5 times, then added with 50 μL/well of a TMB chromogenic substrate (KPL, 52-00-03), incubated at room temperature for 5-10 min, added with 50 μL/well of 1 M $H_2SO_4$ to stop the reaction, and read by a MULTISKAN Go microplate reader (ThermoFisher, 51119200) for the absorbance value at 450 nm, and then $EC_{50}$ was calculated according to the OD value.

Example 13 Assay of Blocking Antigen-Antibody Binding by Antibody

The antigens PD-1 and Sirpα expressed according to the method of Example 1 were diluted with a PBS buffer at pH7.4 to a concentration of 2 μg/mL, added into a 96-well ELISA plate (Corning®, CLS3590-100EA) at a volume of 50 μL/well, and incubated at 37° C. for 2 hours. After the liquid was discarded, the wells were added with a blocking solution of 5% skimmed milk (Sangon Biotech (Shanghai) Co., Ltd., A600669-0250) formulated with PBS at 200 μL/well, and incubated at 37° C. for 3 hours for blocking. The blocking solution was discarded, and the plate was washed with a PBST buffer (pH7.4 PBS containing 0.05% tween-20) for 5 times, then each well was added with 25 μL of 3-fold serial dilution of the antibody to be tested in 1% BSA and 25 μL of biotin-labeled ligands (CD47-his/CD47-hFc, PD-L1, etc., which were expressed and purified by the present disclosure) with a final concentration of 1 μg/mL or 12 μg/mL, and incubated at 37° C. for 1 hour. The plate was washed with PBST for 5 times, added with 50 µL/well of RP-labeled secondary antibody (GenScript Biotechnology Co., Ltd., M00091) diluted at 1:1000, and incubated at 37° C. for 1 hour. The plated was washed with PBST for 5 times, then added with 50 µl/well of a TMB chromogenic substrate (KPL, 52-00-03), incubated at room temperature for 5-10 min, added with 50 µl/well of 1 M $H_2SO_4$ to stop the reaction, and read by a MULTISKAN Go microplate reader (ThermoFisher, 51119200) for the absorbance value at 450 nm, and then $IC_{50}$ was calculated according to the OD value.

The Biotin-labeled kit was Biotin Labeling Kit-NH2, which was purchased from Dojindo Chemical Technology (Shanghai) Co., Ltd., with the Cat. No. LK03. The operation method was carried out according to the instructions, and the labeled antibody was used after the concentration of it was detected with a Multiskan GO (ThermoFisher, 51119200) microplate reader.

Example 14 Design of Bispecific Antibody Against Dual Targets Sirpα and PD-1, and Activity Evaluation In the present disclosure, bispecific antibodies with different sequence structures against two targets Sirpα and PD-1 had been designed, as shown in the table below.

TABLE 18

| Antibody number | Light chain sequence | Heavy chain sequence |
|---|---|---|
| | Bispecific antibodies designed against dual targets Sirpα and PD-1 | |
| LB501 | mab14-h16VL-(G4S)₃-mab14-h16VH-(G4S)₃-PemVL-LC (κ chain) | PemVH-HC (hIgG4) |
| LB502 | PemVL-LC (κ chain) | mab14-h16VL-(G4S)₃-mab14-h16VH-(G4S)₃-PemVH-HC (hIgG4) |
| LB503 | PemVL-LC-(G4S)₃-mab14-h16VH-(G4S)₃-mab14-h16VL(κ chain) | PemVH-HC (hIgG4) |
| LB504 | PemVL-LC (κ chain) | PemVH-HC(hIgG4)-(G4S)₃-mab14-h16VH-(G4S)₃-mab14-h16VL |
| LB505 | NivoVL-LC (κ chain) | mab14-h16VL-(G4S)₃-mab14-h16VH-(G4S)₃-NivoVH-HC (hIgG4) |
| LB506 | NivoVL-LC (κ chain) | NivoVH-HC(hIgG4)-(G4S)₃-mab14-h16VH-(G4S)₃-mab14-h16VL |
| LB507 | mab14-h16VL-LC (κ chain) | PemVL-(G4S)₃-PemVH-(G4S)₃-mab14-h16VH-HC (hIgG4) |
| LB508 | mab14-h16VL-LC (κ chain) | mab14-h16VH-HC(hIgG4)-(G4S)₃-PemVH-(G4S)₃-PemVL |

* κ chain indicated that the light chain was the κ type light chain constant region of human IgG.
: when a linker was linked to the C-terminus of IgG4, the last amino acid K of IgG4 was mutated to A. The design of introducing scFv at the C-terminus of the heavy chain all mutated the last amino acid K to A.

The aforementioned bispecific antibodies were cloned, expressed and purified according to the cloning, expression and purification methods of Example 1 of the present disclosure. The binding activities of these designed bispecific molecules to human Sirpα and PD-1 were detected by the methods of Examples 12 and 13, respectively, and it was found that LB501, LB502, LB503, LB504 and LB506 all could retain the binding activities to the two target antigens. The results were shown in the table below.

TABLE 19

| | Evaluation of binding activities of bispecific antibodies designed against dual targets Sirpα and PD-1 | | | |
|---|---|---|---|---|
| | Activity of binding to human Sirpα-V1 | | Activity of binding to human PD-1 | |
| Antibody number | $EC_{50}$, nM | multiple of change of $EC_{50}$* | $EC_{50}$, nM | multiple of change of $EC_{50}$* |
| LB501 | 0.059 (0.077) | 0.77 | 0.075 (0.15) | 0.50 |
| LB502 | 0.066 (0.077) | 0.86 | 0.074 (0.15) | 0.49 |
| LB503 | 0.075 (0.077) | 0.97 | 0.063 (0.15) | 0.42 |
| LB504 | 0.055 (0.077) | 0.71 | 0.061 (0.15) | 0.41 |
| LB506 | 0.064 (0.077) | 0.83 | 0.053 (0.043) | 1.23 |

: the value in parentheses was the binding activities $EC_{50}$ of the monoclonal antibodies corresponding to the same target under the same experimental conditions.
*the ratio of binding activities $EC_{50}$ of the bispecific antibody and the corresponding monoclonal antibody under the same experimental conditions. When the ratio was larger, it indicated that the decrease in the binding force of the designed bispecific antibody to a single target was larger. For example, if the ratio was 2, it indicated that the binding activity of the designed bispecific antibody to the target was reduced by one time compared with the corresponding monoclonal antibody. When the ratio was within 2 (experimental error range), it indicated that the binding activity was not affected.

In the above table were bispecific molecules designed by placing the scFv of the anti-Sirpα antibody mab14-h16 of the present disclosure at the N-terminus of the heavy chain, the C-terminus of the heavy chain; the N-terminus of the light chain and the C-terminus of the light chain of the PD-1 antibody Pem, or a bispecific molecule designed by placing the scFv of the anti-Sirpα antibody mab14-h16 of the present disclosure at the N-terminus of the heavy chain and the C-terminus of the heavy chain of the PD-1 antibody Nivo, or a bispecific molecule designed from the scFv of the PD-1 antibody Pem and the anti-Sirpα antibody mab14-h16 of the present disclosure.

The results showed that for bispecific antibodies designed from the same Sirpα antibody and scFv at different positions, the effect on the activity of Pem was much less than that on Nivo, such as LB501, LB502, LB503 and LB504 (the scFv linked on the Pem), the binding activities of them to the two targets were all close to those of the corresponding monoclonal antibodies, and compared with the bispecific antibody in which scFv was linked on the Nivo, only LB506 had similar binding activities to the two targets as those of the corresponding monoclonal antibody. It showed that linking the scFv of the Sirpα antibody at different positions had little effect on the activity of Pem, which was different for the effect on the activity of Nivo. Similarly, the binding activities of bispecific antibodies formed by linking the scFv of Pem to the N-terminus of the heavy chain (LB507) and C-terminus of the heavy chain (LB508) of the anti-Sirpα antibody mab14-h16 of the present disclosure were also different. LB507 had the binding activity to Sirpα which was 1-fold weaker than that of the corresponding monoclonal antibody and the binding activity to PD-1 which was close to that of Pem, while the binding activities of LB508 to both targets were significantly reduced.

The aforementioned data of these designed bispecific antibodies of the present disclosure showed that when the Sirpα antibody (the present disclosure) and scFv were the same, the designing manner was the same, but the PD-1 antibody sequence was different, the designed bispecific antibody molecules had huge differences in activity. When the scFv of the Sirpα antibody (the present disclosure) and the PD-1 antibody were the same, but the position of the scFv of the Sirpα antibody (the present disclosure) was different, the designed bispecific antibody molecules had huge differences in activity. When the scFv of the PD-1 antibody and the Sirpα antibody (the present disclosure)

were the same, but the position of the scFv of the PD-1 antibody was different, and the difference in the activity was also very huge.

These data showed that the bispecific antibodies designed based on the Sirpα antibody sequence of the present disclosure had different sequences, different positions of the scFv and antibodies, and thus different activities. With proper positions and proper sequence design, bispecific antibodies with good activity against dual targets could be obtained. These bispecific antibodies were similar in structure to conventional IgGs and had an entire Fc. In the present disclosure, it was called sequence-based IgG like bispecific antibody format (SBody). These bispecific antibody molecules have the same entire Fc as normal antibodies, so that their purification process can be carried out according to those of normal antibodies, and thus the process is simple and has the advantage of low production cost.

The aforementioned SBodies which retained the activity against the two targets, were evaluated for its functions against the two targets (by an assay of blocking the binding of an antigen to a corresponding ligand) respectively, and the results were shown in the table below.

TABLE 21

Evaluation of expression levels of bispecific antibodies designed against dual targets Sirpα and PD-1

| Antibody number | Expression level (mg/L) |
|---|---|
| LB501 | 2.24 |
| LB502 | 2.43 |
| LB503 | 3.83 |
| LB504 | 7.35 |
| LB506 | 44.29 |

The aforementioned result showed that that the design of the present disclosure had a great difference in the expression yield of the Sirpα and PD1 bispecific antibody (SBody). In conclusion of the aforementioned data analysis, for SBodies with the same design mode, the same scFv of the Sirpα antibody and different PD-1 antibody sequences,

TABLE 20

Evaluation of functional activities of bispecific antibodies designed against dual targets Sirpα and PD-1

| Antibody number | Activity of blocking the binding of Sirpα to CD47 (dimer) | | Activity of blocking the binding of Sirpα (dimer) to CD47 | | Activity of blocking the binding of PD-1/PD-L1 | |
|---|---|---|---|---|---|---|
| | IC$_{50}$, nM | multiple of change of IC$_{50}$* | IC$_{50}$, nM | multiple of change of IC$_{50}$* | IC$_{50}$, nM | multiple of change of IC$_{50}$* |
| LB501 | 5.42 (6.14) | 0.88 | 2.55 (3.88) | 0.66 | 1.30 (2.53) | 0.51 |
| LB502 | 5.37 (6.14) | 0.87 | 3.78 (3.88) | 0.97 | 2.00 (2.53) | 0.79 |
| LB503 | 7.63 (6.14) | 1.24 | 4.80 (3.88) | 1.24 | 1.45 (2.53) | 0.57 |
| LB504 | 6.63 (6.14) | 1.08 | 4.62 (3.88) | 1.19 | 1.09 (2.53) | 0.43 |
| LB506 | 6.51 (6.14) | 1.06 | 4.53 (3.88) | 1.17 | 1.39 (1.33) | 1.05 |

: the value in parentheses was the IC$_{50}$ of the activity of the monoclonal antibody corresponding to the same target to block the binding of an antigen to a ligand under the same experimental conditions.
*: the multiple of change of IC$_{50}$, that was, the IC$_{50}$ ratio of the bispecific antibody and the corresponding monoclonal antibody (control antibody). When the ratio was larger, it indicated that the decrease in the functional activity of the designed bispecific antibody to a single target was larger. For example, if the ratio was 2, it indicated that the functional activity of the designed bispecific antibody to the target was reduced by one time compared with the corresponding monoclonal antibody. When the ratio was within 2 as the experimental error range, that was the activity was not affected.
ND: No activity of the molecule of blocking the binding of Sirpα to Daudi cells was detected.

The aforementioned functional activity results showed that the change of the activity of the bispecific antibody (SBody) designed in the present disclosure in blocking the binding of an antigen with a corresponding ligand was consistent with the change of the binding activity thereof, such as LB507, of which the activities of binding to human Sirpα and human PD-1 were slightly weakened and the activities of blocking the binding of human Sirpα to human CD47 and blocking the binding of human PD-1 to human PD-L1 were slightly weakened (compared with the corresponding monoclonal antibodies, the multiples of change were 2.46, 2.59 and 2.20 respectively). Other designs LB501, LB502, LB503, LB504, and LB506 all retained the functional activity against the dual targets.

To evaluate the expression levels of the bispecific antibodies SBodies of the present disclosure, the SBodies were transiently transfected in the same expression system (293F cells) by the same method, and purified by conventional Protein A to obtain the respective expression levels. The results were shown in the table below.

the expression levels were different, and the expression level of the SBody corresponding to Nivo was 5 times or even 17 times higher than that of Pem. For example, the yield of LB506 was 17 times higher than that of LB502 (44.29/2.43); and the yield of LB506 was 5 times higher than that of LB504 (44.29/7.35). For SBodies with the same design mode, the same PD-1 sequence, the same scFv sequence of the Sirpα antibody and different scFv positions, the expression levels also differed by more than 2 times, such as LB504 (7.35 mg/L) vs LB501 (2.24 mg/L) vs LB502 (2.43 mg/L).

These data showed that the bispecific antibody SBody designed from the anti-Sirpα antibody mab14-h16 of the present disclosure and the PD1 antibody was sequence-specific not only in activity, function, but also in expression level.

Partial sequences of the bispecific antibody SBody designed from the anti-Sirpα antibody mab14-h16 of the present disclosure and the PD1 antibody were as follows:

Light chain sequence of LB501:
                                        (SEQ ID NO: 50)
DIQMTQSPSSLSASVGDRVTITCRASQDIRNYLNWYQQKPGKAPKLLIY

FTSTLHSGVPSRFSGSGSGTDFTLTISSLQPEDFATYYCQQGNTLPWTF

GGGTKVEIKGGGGSGGGGSGGGGSQVQLVQSGAEVKKPGASVKVSCKAS

GYNFNIYWINWVRQAPGQGLEWIGNIYPSSISTNYNEKFKTRATLTVDK

STSTVYMELSSLRSEDTAVYYCARSEGTYYGGRYEGDWFGYWGQGTLVT

VSSGGGGSGGGGSGGGGSEIVLTQSPATLSLSPGERATLSCRASKGVST

SGYSYLHWYQQKPGQAPRLLIYLASYLESGVPARFSGSGSGTDFTLTIS

SLEPEDFAVYYCQHSRDLPLTFGGGTKVEIKRTVAAPSVFIFPPSDEQL

KSGTASVVCLLNNFYPREAKVQWKVDNALQSGNSQESVTEQDSKDSTYS

LSSTLTLSKADYEKHKVYACEVTHQGLSSPVTKSFNRGEC

Heavy chain sequence (Pem heavy chain) of LB501:
                                        (SEQ ID NO: 51)
QVQLVQSGVEVKKPGASVKVSCKASGYTFTNYYMYWVRQAPGQGLEWM

GGINPSNGGTNFNEKFKNRVTLTTDSSTTTAYMELKSLQFDDTAVYYCA

RRDYRFDMGFDYWGQGTTVTVSSASTKGPSVFPLAPCSRSTSESTAALG

CLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGK

Light chain sequence (Pem light chain) of LB502:
                                        (SEQ ID NO: 52)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC

Heavy chain sequence of LB502:
                                        (SEQ ID NO: 53)
DIQMTQSPSSLSASVGDRVTITCRASQDIRNYLNWYQQKPGKAPKLLIY

FTSTLHSGVPSRFSGSGSGTDFTLTISSLQPEDFATYYCQQGNTLPWTF

GGGTKVEIKGGGGSGGGGSGGGGSQVQLVQSGAEVKKPGASVKVSCKAS

GYNFNIYWINWVRQAPGQGLEWIGNIYPSSISTNYNEKFKTRATLTVDK

STSTVYMELSSLRSEDTAVYYCARSEGTYYGGRYEGDWFGYWGQGTLVT

VSSGGGGSGGGGSGGGGSQVQLVQSGVEVKKPGASVKVSCKASGYTFTN

YYMYWVRQAPGQGLEWMGGINPSNGGTNFNEKFKNRVTLTTDSSTTTAY

MELKSLQFDDTAVYYCARRDYRFDMGFDYWGQGTTVTVSSASTKGPSVF

PLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCP

PCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSN

KGLPSSIEKTISKAKGQPREPQVYTLPPSQEEMTKNQVSLTCLVKGFYP

SDIAVEWESNGQPENNYKTTPPVLDSDGSFFLYSRLTVDKSRWQEGNVF

SCSVMHEALHNHYTQKSLSLSLGK

Light chain sequence of LB503:
                                        (SEQ ID NO: 54)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGECAGGGGSGGGGSGGGGSQVQLVQSGAEV

KKPGASVKVSCKASGYNFNIYWINWVRQAPGQGLEWIGNIYPSSISTNY

NEKFKTRATLTVDKSTSTVYMELSSLRSEDTAVYYCARSEGTYYGGRYE

GDWFGYWGQGTLVTVSSGGGGSGGGGSGGGGSDIQMTQSPSSLSASVGD

RVTITCRASQDIRNYLNWYQQKPGKAPKLLIYFTSTLHSGVPSRFSGSG

SGTDFTLTISSLQPEDFATYYCQQGNTLPWTFGGGTKVEIK

Heavy chain sequence (Pem heavy chain) of LB503: the same as SEQ ID NO: 51.

Light chain sequence (Pem light chain) of LB504: the same as SEQ ID NO: 52.

Heavy chain sequence of LB504:
                                        (SEQ ID NO: 55)
QVQLVQSGVEVKKPGASVKVSCKASGYTFTNYYMYWVRQAPGQGLEWM

GGINPSNGGTNFNEKFKNRVTLTTDSSTTTAYMELKSLQFDDTAVYYCA

RRDYRFDMGFDYWGQGTTVTVSSASTKGPSVFPLAPCSRSTSESTAALG

CLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGAGGGGSGGGGSGGGGSQVQLVQSGAEVKKPGASVKVSCKASGY

NFNIYWINWVRQAPGQGLEWIGNIYPSSISTNYNEKFKTRATLTVDKST

STVYMELSSLRSEDTAVYYCARSEGTYYGGRYEGDWFGYWGQGTLVTVS

SGGGGSGGGGSGGGGSDIQMTQSPSSLSASVGDRVTITCRASQDIRNYL

NWYQQKPGKAPKLLIYFTSTLHSGVPSRFSGSGSGTDFTLTISSLQPED

FATYYCQQGNTLPWTFGGGTKVEIK

Light chain sequence (Nivo light chain) of LB506:
                                        (SEQ ID NO: 56)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIKRTVAAPSVFIFPPSDEQLKSGTASVVCLLNNFYPREAKVQ

-continued

WKVDNALQSGNSQESVTEQDSKDSTYSLSSTLTLSKADYEKHKVYACEV

THQGLSSPVTKSFNRGEC

Heavy chain sequence of LB506:

(SEQ ID NO: 57)

QVQLVESGGGVVQPGRSLRLDCKASGITFSNSGMHWVRQAPGKGLEWVA

VIWYDGSKRYYADSVKGRFTISRDNSKNTLFLQMNSLRAEDTAVYYCAT

NDDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGAG

GGGSGGGGSGGGGSQVQLVQSGAEVKKPGASVKVSCKASGYNFNIYWIN

WVRQAPGQGLEWIGNIYPSSISTNYNEKFKTRATLTVDKSTSTVYMELS

SLRSEDTAVYYCARSEGTYYGGRYEGDWFGYWGQGTLVTVSSGGGGSGG

GGSGGGGSDIQMTQSPSSLSASVGDRVTITCRASQDIRNYLNWYQQKPG

KAPKLLIYFTSTLHSGVPSRFSGSGSGTDFTLTISSLQPEDFATYYCQQ

GNTLPWTFGGGTKVEIK

Example 15 Evaluation of Stability of Sirpα and PD-1 Bispecific Antibody of the Present Disclosure in Different Formulation Recipes The bispecific antibody LB504 of the aforementioned Example 14 was replaced by a desalting centrifugal column (Thermo, Cat #89890) into each formulation recipe, and the formulation recipe scheme was as shown in Table 22. The replacement process of each formulation buffer was as follows: the desalting centrifugal column was pretreated, wherein the desalting centrifugal column was centrifuged at 1,000 g for 2 min, the stock solution was removed, the desalting centrifugal column was added with 1 mL of each formulation buffer and centrifuged at 1,000 g for 2 min for 3 times, and the buffer in the collection tube was discarded; the desalting centrifugal column was placed in a new collection tube, slowly added with an appropriate amount of LB504, added with 20 μL of the formulation buffer for a hydraulic layer, and centrifuged at 1,000 g for 2 min to collect the centrifuged samples, and the samples were mixed evenly and filtered with a 0.2 μm filter membrane; the filtered LB504 formulation samples were subpackaged at 200 μL/tube, 3 of the tubes were placed in a 40° C. water bath kettle, and the samples were detected by SEC-HPLC and SDS-PAGE on days 9, 20 and 30 respectively, i.e., detection of the samples treated at 40° C. for 9 days, 20 days and 30 days; and another tube was taken and detected by SEC-HPLC and SDS-PAGE after sterile subpackaging, i.e., detection of the samples treated at 40° C. for 0 day. The SEC-HPLC results of different formulation recipes were as shown in Table 23.

TABLE 22

Formulation recipe scheme of bispecific antibody LB504 of the present disclosure

| Recipe number | Composition of formulation recipe formulation buffer | Experimental conditions and sampling time points |
|---|---|---|
| 1 | 20 mM citric acid-sodium citrate, 125 mM glycine, 125 mM trehalose, 0.02% ps80, pH 5.0 | Protein concentration of 5 ± 0.2 mg/mL, placed at 40 ± 2° C., |
| 2 | 20 mM acetic acid-sodium acetate, 125 mM glycine, 125 mM trehalose, 0.02% ps80, pH 5.0 | under accelerated conditions, sampled on days 0, 9, 20, and 30 |
| 3 | 20 mM His-HCl, 125 mM glycine, 125 mM trehalose, 0.02% ps80, pH 5.5 | respectively |
| 4 | 20 mM citric acid-sodium citrate, 125 mM glycine, 125 mM trehalose, 0.02% ps80, pH 5.5 | |
| 5 | 20 mM His-HCl, 125 mM glycine, 125 mM trehalose, 0.02% ps80, pH 6.0 | |
| 6 | 20 mM citric acid-sodium citrate, 125 mM glycine, 125 mM trehalose, 0.02% ps80, pH 6.0 | |
| 7 | 20 mM His-HCl, 125 mM glycine, 125 mM trehalose, 0.02% ps80, pH 6.5 | |
| 8 | 20 mM PB (phosphate buffer), 125 mM glycine, 125 mM trehalose, 0.02% ps80, pH 7.0 | |

TABLE 23

Detection results of formulation recipe samples of the bispecific antibody LB504 of the present disclosure by SEC-HPLC

| Recipe number | Condition | Treatment days | % aggregation | % monomer | % fragment |
|---|---|---|---|---|---|
| 1 | 40° C. | 0 | 4.74 | 95.26 | 0 |
| | | 9 | 7.89 | 92.11 | 0 |
| | | 20 | 12.3 | 87.3 | 0.4 |
| | | 30 | 24.56 | 74.89 | 0.55 |
| 2 | 40° C. | 0 | 0.69 | 99.31 | 0 |
| | | 9 | 0.73 | 99.27 | 0 |
| | | 20 | 2.34 | 97.37 | 0.3 |
| | | 30 | 3.59 | 96.05 | 0.36 |
| 3 | 40° C. | 0 | 0.14 | 99.86 | 0 |
| | | 9 | 0.16 | 99.78 | 0.06 |
| | | 20 | 2.16 | 97.63 | 0.2 |
| | | 30 | 4.9 | 94.77 | 0.33 |
| 4 | 40° C. | 0 | 6.05 | 93.95 | 0 |
| | | 9 | 10.1 | 89.9 | 0 |
| | | 20 | 11.93 | 87.75 | 0.33 |
| | | 30 | 18.75 | 80.85 | 0.4 |
| 5 | 40° C. | 0 | 0.13 | 99.87 | 0 |
| | | 9 | 0.2 | 99.8 | 0 |
| | | 20 | 3.62 | 96.14 | 0.24 |
| | | 30 | 5.03 | 94.54 | 0.44 |
| 6 | 40° C. | 0 | 6.77 | 93.23 | 0 |
| | | 9 | 9.45 | 90.55 | 0 |
| | | 20 | 11.12 | 88.68 | 0.2 |
| | | 30 | 16.23 | 83.39 | 0.37 |
| 7 | 40° C. | 0 | 0.15 | 99.85 | 0 |
| | | 9 | 0 | 100 | 0 |
| | | 20 | 0.83 | 98.6 | 0.57 |
| | | 30 | 2.1 | 97.1 | 0.8 |

TABLE 23-continued

Detection results of formulation recipe samples of the bispecific
antibody LB504 of the present disclosure by SEC-HPLC

| Recipe number | Condition | Treatment days | % aggregation | % monomer | % fragment |
|---|---|---|---|---|---|
| 8 | 40° C. | 0 | 5.57 | 94.43 | 0 |
| | | 9 | 8.73 | 91.05 | 0.22 |
| | | 20 | 12.91 | 86.22 | 0.86 |
| | | 30 | 19.09 | 79.85 | 1.07 |

The aforementioned results showed that when the bispecific antibody LB504 of the present disclosure was in a citric acid buffer system (pH5.0, pH5.5, pH6.0) and a phosphate buffer system at a medium concentration (5 mg/mL), the polymer was increased after buffer replacement, and with the increase of the treatment time at 40° C., the increase of the polymer was obvious and meanwhile a few fragments were produced, and the purity detected by SEC-HPLC was decreased to about 80%. LB504 exhibited as relatively stable in a acetic acid buffer system (pH5.0), and after 30 days of treatment at 40° C., the polymer was increased by 3.59%, the fragments were increased by 0.36%, and the decrease of the total purity detected by SEC-HPLC was within 5%. In a histidine buffer system (including pH5.5, pH6.0, pH6.5), LB504 had a high purity after buffer replacement, and after 30 days of treatment at 40° C., it exhibited as relatively stable with little increase of polymers, and with the increase of the pH of the buffer, the generation of the polymer was decreased. When LB504 was treated in recipe 7 (20 mM His-HCl, 125 mM glycine, 125 mM trehalose, 0.02% ps80, pH6.5) at 40° C. for 30 days, the purity detected by SEC-HPLC was decreased by 2.1%, the fragments were increased by 0.8%, and the change trend of the purity was small. More preferably, when LB504 was treated in recipe 7 at 40° C. for 20 days, almost no polymer and fragment were produced, and the purity was decreased to 1.4% (0.83% of the polymer and 0.57% of the fragments were produced respectively). The results of SDS-PAGE also showed that LB504 treated at 40° C. for 20 days in recipe 7 had almost no generation of polymers and degraded fragments.

The aforementioned results showed that the bispecific antibody LB504 of the present disclosure had the best stability in the formulation buffer (20 mM His-HCl, 125 mM glycine, 125 mM trehalose, 0.02% ps80, pH6.5) at a high concentration (5 mg/mL), and it could remain stable after being treated at 40° C. for 30 days, and the purity detected by SEC-HPLC was decreased only by 2.9%, which indicated that LB504 had good stability.

Example 16 Evaluation of In Vivo Pharmaceutical Effect of the Optimally Designed Molecule of Sirpα and PD-1 Bispecific Antibody of the Present Disclosure in an Animal An animal pharmacodynamic model was established with human PD-1/Sirpα double transgenic Balb/cJGPt strain mice Balb/cJGPt-hPD-1/hSirpα to conduct in vivo pharmaceutical effect evaluation of the bispecific antibody LB504 of the present disclosure. The mice were purchased from Jiangsu GemPharmatech Co., Ltd., with the production license number: SCXK (Su) 2018-0008.

Using the method of Example 2, the full-length sequence of human CD47 (see Example 1) was overexpressed on the surfaces of CT26 cells (purchased from the cell bank of National Collection of Authenticated Cell Cultures of Chinese Academy of Sciences) to obtain mouse colon cancer cell line CT26-920 overexpressing human CD47. The constructed CT26-920 cells were cultured in a RPMI1640 medium (Hyclone, Cat #SH3080901) containing 10% fetal bovine serum (Gibco, Cat #10270-106), and continuously cultured in a 37° C. cell incubator containing 5% $CO_2$. Balb/cJGPt-hPD-1/hSirpα female mice were raised at 5 mice/cage in a SPF-level environment, at a temperature of 20-25° C. and humidity of 40%-60%, the mice had access to food and water ad libitum, and the litter was changed regularly. When the CT26-920 cells were cultured to the logarithmic growth phase (with the confluence of 80%-90%), they were digested with 0.25% pancreatin, and the cells were collected, washed twice with a RPMI1640 medium, and resuspended with the RPMI1640 medium and counted. After that, the RPMI1640 medium and Matrigel were mixed at a ratio of 2:1 to finally adjust the cell density to $6\times10^6$ cells/mL with the mixture. 100 μL of CT26 cell suspension was inoculated subcutaneously in the left flank of the mice ($0.6\times10^6$ cells/mouse), and the mice with a tumor volume of about 100-120 $mm^3$ were selected for random grouping, with 8 mice in each group.

In a sterile environment, the samples to be tested and the control samples were formulated with PBS. PBS was the Blank group, the PD-1 antibody (a-PD1, i.e. anti-PD1 antibody Pembrolizumab/Keytruda® (referred to as Pem for short), cloned and expressed by the method of Example 1 of the present disclosure) and Ref1 were respectively control groups of individual medications. LB504 was the group of the drug to be tested. The mode of administration was intraperitoneal injection, the administrated dosage of the groups of individual medications was 10 mg/kg, the administrated dosage of LB504 was 13.3 mg/kg, and the injection volume of each group was 200 μL/mouse (LB504 and each control antibody were equimolar). The dosing frequency was 2 time/week, and the dose was administered continuously for 2 weeks.

The day of the first administration of each dose group was Day 0. The body weight and tumor size were measured before each administration, and the data was recorded. The actual administration period of this experiment was 2 weeks, and the measurement period was 16 days. After completion of tumor measurement, the tumor volume, the relative tumor volume and the tumor inhibition rate were calculated. The results were as shown in FIG. 4 and Table 24.

Calculation formula of tumor size: The tumor volume TV ($mm^3$)=0.5×(tumor long diameter×tumor short diameter$^2$); the relative tumor volume (RTV)=T/T0 or C/C0. The relative tumor growth rate (T/C %)=100%×(T−T0)/(C−C0); the tumor inhibition rate (TGI)=(1−T/C)×100%; wherein T0 and T were the tumor volumes at the beginning and end of the experiment in each administration group, respectively; and C0 and C were the tumor volumes of the control group at the beginning and end of the experiment, respectively.

Figure 4:
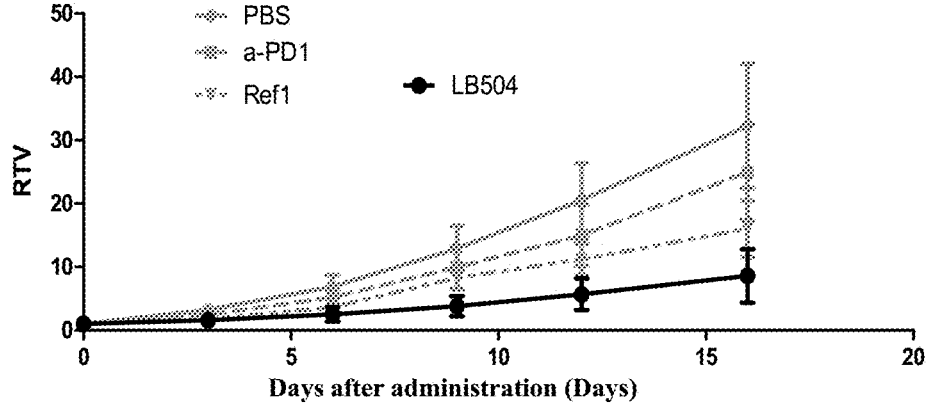
FIG. 4 shows the in vivo pharmacodynamic activity of the Sirpα and PD-1 bispecific antibody of the present disclosure.

The results in FIG. 4 and Table 24 showed that in a Balb/cJGPt-hPD-1/hSirpα double knock-in mouse CT26 colon cancer animal model, the bispecific antibody molecule LB504 of the present disclosure showed obvious inhibition effect on tumor growth, and the in vivo pharmaceutical effect in the mice was significantly better than that of equal molar doses of Ref1 and a-PD1, and even better, the tumor inhibition rate of the group administrated with LB504 could reach 71%.

TABLE 24

| | | | | | | | |
|---|---|---|---|---|---|---|---|
| | Mean tumor volume (mm³) | | Mean tumor volume (mm³) | | TGI % | | Number mice |
| Group | D0 | SD | D16 | SD | D16 | P | of dead |
| PBS | 108.46 | 33.21 | 3316.05 | 2816.48 | — | | 0 |
| a-PD1-10 | 109.05 | 28.56 | 2813.69 | 2737.19 | 16% | 0.3659 | 0 |
| Ref1-10 | 107.20 | 25.54 | 1711.72 | 1435.57 | 50% | 0.0866 | 0 |
| LB504-13.3 | 106.72 | 24.98 | 1044.75 | 1536.81 | 71% | 0.0325* | 0 |

Results of relative tumor volume analysis and TGI calculation after 16 days of administration

*represents $p < 0.05$

Meanwhile, on day 19 after administration, 5 mice were taken from each group for TILs analysis. Specifically, the tumor of each mouse was taken out and put into a dish, cut into small tissue pieces of 2-4 mm, then transferred into a centrifuge tube containing an enzyme digestion buffer (collagenase IV+DNase I), digested at 37° C., then filtered with a filter screen, and centrifuged (400 g, 5 min). The supernatant was discarded, and the pellet was added with red blood cell lysis buffer for lysis of red blood cells, and centrifuged. The pellet was added with PBS to resuspend the cells and cell counting was conducted, and then $1 \times 10^6$ cells/sample were taken for subsequent staining and labeling. The cells were taken, added with Fc Block antibodies, incubated for 10-15 min, then added into each mixed solution of fluorescent antibodies respectively, incubated at 4° C. for 30 min, and washed with 200 μL of a FACS buffer twice. The supernatant was discarded, and the pellet was added with 100 μL of the FACS buffer to resuspend cells, and then the resuspended cells were detected on a machine. The results were as shown in Table 25.

TABLE 25

| | % of lives | % of CD45+ M2 | % of CD3+ | | % of CD3+ |
|---|---|---|---|---|---|
| Group | CD45+ | (CD206+) | CD4+ | CD8+ | CD25+CD4+ |
| G1: PBS | 38.09 | 11.10 | 22.27 | 56.12 | 13.87 |
| G2: Ref1 | 23.96 | 12.17 | 22.18 | 54.63 | 12.34 |
| G3: a-PD1 | 36.61 | 10.52 | 19.24 | 60.42 | 10.02 |
| G4: LB504 | 44.93 | 4.25 | 16.83 | 59.95 | 8.83 |

Analysis results of tumor TILs in mice of each administration group (mean)

The results of TILs analysis showed that the proportion of total lymphocytes and CD8+ T lymphocytes in the tumor microenvironment of mice in each administration group had little change, but the proportion of CD4+ T lymphocytes was decreased, and was decreased significantly in the group administrated with LB504, which was mainly caused by the decrease of CD4+CD25+ cells (Treg). The proportion of CD206+ cells (M2-type macrophages) in the dosage group administrated with LB504 was also decreased significantly by 61.7% (compared with the PBS group, 4.25% vs 11.1%). The proportions of CD11+/F4-80+ cells and CD206– cells in each administration group were basically the same as those in the PBS group. The results indicated that the bispecific antibody LB504 of the present disclosure exerted an antitumor pharmaceutical effect by reducing the proportions of suppressor T cells (Treg) and M2 macrophages.

Example 17 PK Evaluation of the Sirpα and PD-1 Bispecific Antibody of the Present Disclosure PK evaluation of the bispecific antibody of the present disclosure was carried out under the same feeding conditions with the same human Sirpα and PD-1 double transgenic mice as in Example 16. 3 mice were randomly selected to form a group. The mice were injected with LB504 via tail vein, with an injection dose being 13.3 mg/kg and an injection volume being 200 μL/mice. Blood samples were drawn from the orbit at 0 hours before the injection and 0.25, 0.5, 1, 5, 24, 48, 72, 101, 120, 144, 168, 192, 216, and 288 hours after injection, respectively. The blood samples were centrifuged, and the supernatant was taken and stored at –20° C. After blood samples at all time points were collected, the PK characteristics of LB504 were evaluated by double-antigen sandwich ELISA detection of the binding of LB504 to PD-1 and Sirpα (the bispecific antibody could bind to PD-1 and Sirpα simultaneously). PK data was analyzed with EXCEL software, and the $T_{1/2}$ of LB504 was calculated. The results were shown in Table 26.

TABLE 26

| | | | | |
|---|---|---|---|---|
| | Antibody LB504 Antigen PD-1/Sirpα Serial number of mouse | | | |
| | 1 | 2 | 3 | Mean |
| $T_{max}$ (h) | 0.25 | 0.25 | 0.25 | 0.25 |
| $C_{max}$ (g/mL) | 224.6 | 187.86 | 161.1 | 191.19 |
| $T_{1/2}$ (101 h) | 35.36 | 20.38 | 38.2 | 31.31 |
| $AUC_{0-101\ h}$ (μg/mL*h) | 3874 | 1671 | 1978 | 2507.67 |

PK evaluation of the PD-1 and Sirpα bispecific antibody of the present disclosure The aforementioned results showed that after a single tail injection of the bispecific antibody LB504 of the present disclosure into the mice, the concentration reached the highest value at 0.25 h, and the Cmax and $AUC_{0-101\ h}$ were 191.19 g/mL and 2507.67 μg/mL*h, respectively. $T_{1/2}$ was 31.31 hours. The results showed that the in vivo PK parameters of the bispecific antibody LB504 of the present disclosure in the mice are in a normal range, and thus the bispecific antibody was exploitable.

In conclusion of the aforementioned data of the present disclosure, it indicated that through innovative screening, the inventor had accidentally discovered an anti-human Sirpα antibody, which had good binding activity to Sirpα and could bind to human Sirpα-V1 and human SIRPα-V2 simultaneously; and had very good binding activities to all of various polymorphic proteins of Sirpα of the non-human primate *cynomolgus* monkey. It could effectively block the binding of human Sirpα to human CD47. It had better activity than the currently clinical antibodies (control antibodies Ref1 and Ref2); and did not bind to human Sirpβ and human Sirpγ, and also did not bind to human T cells, so that it had very good selectivity, could avoid the off-target effect caused by clinical off-target, and could avoid side effects more effectively. Furthermore, the sequence of the molecule itself had a low PTM risk. The humanized antibody had a high expression level, which provided convenience and cost savings for downstream production and processes. Furthermore, the bispecific antibody designed based on the Sirpα antibody sequence of the present disclosure could retain the functional activity of the antibody against dual targets, the activity of it of binding to the two targets was close to that of its corresponding monoclonal antibody, and the activity of it in blocking the binding of the antigen to a corresponding ligand was also consistent with that of the corresponding monoclonal antibody; and it could effectively inhibit tumor growth; had good stability, and was relatively stable in both a acetic acid buffer system and a histidine buffer system. These bispecific antibodies (called SBodies in the present disclosure), which are similar in structure to conventional IgGs, have the same entire Fc as normal antibodies, so that their purification process can be carried out according to those of normal antibodies, and thus the process is simple and has the advantage of low production cost. The unique characteristics of the antibody of the present disclosure made it more suitable for the development of antibody drugs against the human Sirpα target, and as a candidate drug, it could be administered alone or in combination, especially providing a new and even better option for the treatment of tumors in combination with the PD-1 antibody, and the preferred bispecific antibody of the present disclosure provided another option for multi-target therapy of tumors.

---

What is claimed is:

1. An Sirpα-targeting antibody or an antigen-binding fragment thereof, comprising a light chain variable region and a heavy chain variable region, wherein the antibody or the antigen-binding fragment thereof binds to human Sirpα-V1 and human Sirpα-V2, but faintly binds to or does not bind to human Sirpβ and Sirpγ, and does not bind to human T cells, and has the function of blocking the binding of Sirpα to CD47; wherein faintly bind means that the EC50 in the binding experiment is 10 nM≤EC50<50 nM; does not bind means that the EC50 in the binding experiment is 50 nM≤EC50 or that the binding signal is undetectable;

the antibody or the antigen-binding fragment thereof also binds to one or more of Cyno Sirpα L932, L933, L936 and L937, but does not bind to Cyno Sirpα L938 and L939; wherein the amino acid sequence of the L932 has a NCBI sequence number of NP_001271679.1 and as shown in SEQ ID NO: 62, the amino acid sequence of the L933 has a NCBI sequence number of NP_001271679.2 and as shown in SEQ ID NO: 63, the amino acid sequence of the L936 is as shown in SEQ ID NO: 3, the amino acid sequence of the L937 is as shown in SEQ ID NO: 4, the amino acid sequence of the L938 is as shown in SEQ ID NO: 5, and the amino acid sequence of the L939 is as shown in SEQ ID NO: 6;

the light chain variable region comprises the following CDRs: VL CDR1 as shown in the amino acid sequence of SEQ ID NO: 11; VL CDR2 as shown in the amino acid sequence of SEQ ID NO: 12; and VL CDR3 as shown in the amino acid sequence of SEQ ID NO: 13; and the heavy chain variable region comprises the following CDRs: VH CDR1 as shown in the amino acid sequence of SEQ ID NO: 14; VH CDR2 as shown in the amino acid sequence of SEQ ID NO: 15; and VH CDR3 as shown in the amino acid sequence of SEQ ID NO: 16.

2. The Sirpα-targeting antibody or the antigen-binding fragment thereof of claim 1, the amino acid sequence of the light chain variable region is as shown in SEQ ID NO: 9; or the amino acid sequence of the heavy chain variable region is as shown in SEQ ID NO: 10.

3. The Sirpα-targeting antibody or the antigen-binding fragment thereof of claim 1, wherein the Sirpα-targeting antibody is a humanized antibody;

a framework region of the humanized antibody comprises a heavy chain framework region of a human antibody and a light chain framework region of a human antibody;

the light chain variable region comprises the amino acid sequence as shown in SEQ ID NO: 29, and the heavy chain variable region comprises the amino acid sequence as shown in SEQ ID NO: 35; or alternatively, the light chain variable region comprises the amino acid sequence as shown in SEQ ID NO: 30, and the heavy chain variable region comprises the amino acid sequence as shown in any one of SEQ ID NOs: 36-41; or alternatively, the light chain variable region comprises the amino acid sequence as shown in any one of SEQ ID NOs: 31-34, and the heavy chain variable region comprises the amino acid sequence as shown in SEQ ID NO: 36; or alternatively, the light chain variable region comprises the amino acid sequence as shown in any one of SEQ ID NO: 29 or 31-34, and the heavy chain variable region comprises the amino acid sequence as shown in SEQ ID NO: 39.

4. The Sirpα-targeting antibody or the antigen-binding fragment thereof of claim 3, wherein the light chain of the antibody or the antigen-binding fragment thereof comprises a κ or λ type light chain constant region of a human antibody or a mutation thereof; or the heavy chain of the antibody or the antigen-binding fragment thereof comprises a heavy chain constant region of human IgG1, IgG2, IgG3 or IgG4 or a mutation thereof;

the Sirpα-targeting antibody or the antigen-binding fragment thereof comprising the following light and heavy chains: the light chain shown in any one of the amino acid sequences of SEQ ID NO: 42 or 44-48, and the heavy chain shown in the amino acid sequence of SEQ ID NO: 43.

5. The Sirpα-targeting antibody or the antigen-binding fragment thereof of claim 1, wherein the Sirpα-targeting antibody or the antigen-binding fragment thereof comprises immunoglobulin, Fab, Fab', F(ab')$_2$, Fv or scFv, a bispecific antibody or a multispecific antibody.

6. An isolated nucleic acid, wherein the isolated nucleic acid encodes the Sirpα-targeting antibody or the antigen-binding fragment thereof of claim 1.

7. A recombinant expression vector comprising the isolated nucleic acid of claim 6.

8. A transformant comprising the recombinant expression vector of claim 7 in a host cell.

9. A method for preparing a Sirpα-targeting antibody or an antigen-binding fragment thereof, comprising culturing the transformant of claim 8, and obtaining the Sirpα-targeting antibody or the antigen-binding fragment thereof from a culture.

10. A pharmaceutical composition comprising the Sirpα-targeting antibody or the antigen-binding fragment thereof of claim 1, and a pharmaceutically acceptable carrier.

11. A method for treating a tumor in a subject in need thereof, comprising: administering an effective amount of the Sirpα-targeting antibody or the antigen-binding fragment thereof of claim 1 to the subject.

12. A method for treating a tumor in a subject in need thereof, comprising: administering an effective amount of the pharmaceutical composition of claim 10 to the subject.

13. A bispecific antibody comprising a first protein functional region and a second protein functional region, wherein the first protein functional region is the Sirpα-targeting antibody or the antigen-binding fragment thereof of claim 1; and the second protein functional region is an antibody targeting a non-Sirpα antigen or an antigen-binding fragment thereof;

the second protein functional region is an anti-PD-1 antibody, the anti-PD-1 antibody is Nivolumab or Pembrolizumab.

14. The bispecific antibody of claim 13, wherein the second protein functional region is immunoglobulin, and the first protein functional region is two scFvs; wherein, the scFv comprises a heavy chain variable region and a light chain variable region that are linked by a linker; the scFv is linked to the immunoglobulin through a linker, the linker is as shown in SEQ ID NO: 58, 59, 60 or 61.

15. The bispecific antibody of claim 14, the first protein functional region is scFv, and the second protein functional region is immunoglobulin; wherein, the scFv of the first protein functional region comprises the light chain variable region and heavy chain variable region; the amino acid sequence of the light chain variable region is as shown in SEQ ID NO: 9, and the amino acid sequence of the heavy chain variable region is as shown in SEQ ID NO: 10;

wherein, the immunoglobulin comprises the light chain variable region of Pembrolizumab (Pem), the κ type chain as the light chain constant region, the heavy chain variable region of Pembrolizumab (Pem), and the amino acid sequence of hIgG4 as the heavy chain constant region; or alternatively, the immunoglobulin comprises the light chain variable region of Nivolumab (Nivo), the κ type chain as the light chain constant region, the heavy chain variable region of Nivolumab (Nivo), and the amino acid sequence of hIgG4 as the heavy chain constant region;

the C-terminuses of the heavy chain variable regions of the two scFvs are symmetrically linked to the N-terminuses of the two heavy chains of the immunoglobulin through the linker; and, the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39; or alternatively, the C-terminuses of the heavy chain variable regions of the two scFvs are symmetrically linked to the N-terminuses of the two light chain variable regions of the immunoglobulin through the linker; and, the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39; or alternatively, the N-terminuses of the heavy chain variable regions of the two scFvs are symmetrically linked to the C-terminuses of the two heavy chains of the immunoglobulin through the linker; and, the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39; or alternatively, the N-terminuses of the heavy chain variable regions of the two scFvs are symmetrically linked to the C-terminuses of the two light chains of the immunoglobulin through the linker; and, the light chain variable region of the scFv is a light chain variable region having the amino acid sequence as shown in SEQ ID NO: 29, and the heavy chain variable region of the scFv is a heavy chain variable region having the amino acid sequence as shown in SEQ ID NO: 39.

16. The bispecific antibody of claim 13, wherein the bispecific antibody comprises the following light chain amino acid sequence and heavy chain amino acid sequence: wherein the light chain amino acid sequence as shown in SEQ ID NO: 50, and the heavy chain amino acid sequence as shown in SEQ ID NO: 51; or alternatively, the light chain amino acid sequence as shown in SEQ ID NO: 52, and the heavy chain amino acid sequence as shown in SEQ ID NO: 53; or alternatively, the light chain amino acid sequence as shown in SEQ ID NO: 54, and the heavy chain amino acid sequence as shown in SEQ ID NO: 51; or alternatively, the light chain amino acid sequence as shown in SEQ ID NO: 52, and the heavy chain amino acid sequence as shown in SEQ ID NO: 55; or alternatively, the light chain amino acid sequence as shown in SEQ ID NO: 56, and the heavy chain amino acid sequence as shown in SEQ ID NO: 57.

17. A pharmaceutical composition comprising the bispecific antibody of claim 13, and a pharmaceutically acceptable carrier.

18. A method for treating a tumor in a subject in need thereof, comprising: administering an effective amount of the bispecific antibody of claim 13 to the subject.

19. An Sirpα-targeting antibody comprising a light chain variable region and a heavy chain variable region, wherein the light chain variable region comprises the following CDRs: VL CDR1 as shown in the amino acid sequence of SEQ ID NO: 11; VL CDR2 as shown in the amino acid sequence of SEQ ID NO: 12; and VL CDR3 as shown in the amino acid sequence of SEQ ID NO: 13; and the heavy chain variable region comprises the following CDRs: VH CDR1 as shown in the amino acid sequence of SEQ ID NO: 14; VH CDR2 as shown in the amino acid sequence of SEQ ID NO: 15; and VH CDR3 as shown in the amino acid sequence of SEQ ID NO: 16.

\* \* \* \* \*